United States Patent
Shapiro et al.

(10) Patent No.: US 10,766,955 B2
(45) Date of Patent: Sep. 8, 2020

(54) ANTI-TGF-β ANTIBODIES AND THEIR USE

(71) Applicant: SANOFI, Paris (FR)

(72) Inventors: Gary Shapiro, Arlington, MA (US); Kevin Brower, Holliston, MA (US); Patrick Finn, Franklin, MA (US); Richard C. Gregory, Framingham, MA (US); Rao Koduri, Shrewsbury, MA (US); Feng Liu, San Diego, CA (US); Natalia Malkova, Needham, MA (US); Parminder Mankoo, Foster City, CA (US); Jack R. Pollard, Acton, MA (US); Huawei Qiu, Westborough, MA (US); Joachim Theilhaber, Cambridge, MA (US); Christopher Winter, Swampscott, MA (US); Marcella Yu, Fremont, CA (US)

(73) Assignee: SANOFI, Paris (FR)

(*) Notice: Subject to any disclaimer, the term of this patent is extended or adjusted under 35 U.S.C. 154(b) by 196 days.

(21) Appl. No.: 15/875,532

(22) Filed: Jan. 19, 2018

(65) Prior Publication Data

US 2018/0244763 A1 Aug. 30, 2018

Related U.S. Application Data

(60) Provisional application No. 62/448,800, filed on Jan. 20, 2017.

(30) Foreign Application Priority Data

Jan. 20, 2017 (EP) .................................... 17305061

(51) Int. Cl.
| | | |
|---|---|---|
| *A61K 39/00* | (2006.01) | |
| *A61P 35/00* | (2006.01) | |
| *C07K 16/22* | (2006.01) | |
| *C07K 16/30* | (2006.01) | |
| *C07K 16/32* | (2006.01) | |
| *C07K 16/28* | (2006.01) | |

(52) U.S. Cl.
CPC ............. *C07K 16/22* (2013.01); *A61P 35/00* (2018.01); *C07K 16/2818* (2013.01); *C07K 16/30* (2013.01); *C07K 16/32* (2013.01); *A61K 2039/505* (2013.01); *A61K 2039/507* (2013.01); *C07K 2317/52* (2013.01); *C07K 2317/56* (2013.01); *C07K 2317/565* (2013.01); *C07K 2317/76* (2013.01); *C07K 2317/92* (2013.01)

(58) Field of Classification Search
CPC ...... A61K 39/00113; A61K 39/001134; A61K 2039/505; A61K 2039/507; C07K 16/22; C07K 16/32; C07K 16/30; C07K 2317/52; C07K 2317/56; C07K 2317/565; C07K 2317/76; C07K 2317/92; A61P 35/00
See application file for complete search history.

(56) References Cited

U.S. PATENT DOCUMENTS

| | | | |
|---|---|---|---|
| 5,571,714 | A | 11/1996 | Dasch et al. |
| 5,824,655 | A | 10/1998 | Border |
| 6,419,928 | B1 | 7/2002 | Dasch et al. |
| 7,527,791 | B2 | 5/2009 | Adams et al. |
| 7,723,486 | B2 | 5/2010 | Ledbetter et al. |
| 8,114,845 | B2 | 2/2012 | Langermann et al. |
| 8,383,780 | B2 | 2/2013 | Ledbetter et al. |
| 8,591,901 | B2 | 11/2013 | Ledbetter et al. |
| 8,609,089 | B2 | 12/2013 | Langermann et al. |
| 9,090,685 | B2 | 7/2015 | Ledbetter et al. |
| 9,205,148 | B2 | 12/2015 | Langermann et al. |
| 9,481,726 | B2 | 11/2016 | Ledbetter et al. |
| 2003/0224501 | A1 | 12/2003 | Young et al. |
| 2012/0114648 | A1 | 5/2012 | Langermann et al. |
| 2012/0114649 | A1 | 5/2012 | Langermann et al. |
| 2013/0039911 | A1 | 2/2013 | Atul et al. |
| 2014/0099254 | A1 | 4/2014 | Chang et al. |
| 2015/0203579 | A1 | 7/2015 | Papadopoulos et al. |
| 2015/0322530 | A1* | 11/2015 | Orsulic ................ C12Q 1/6886 424/133.1 |
| 2016/0289315 | A1 | 10/2016 | Mirza et al. |
| 2016/0304607 | A1 | 10/2016 | Sadineni et al. |
| 2017/0066821 | A1 | 3/2017 | Ledbetter et al. |

FOREIGN PATENT DOCUMENTS

| | | |
|---|---|---|
| EP | 2350129 B1 | 6/2015 |
| EP | 2927240 A1 | 10/2015 |
| WO | WO 94/13804 A1 | 6/1994 |
| WO | WO 97/13844 A1 | 4/1997 |
| WO | WO 97/29131 A1 | 8/1997 |
| WO | WO 2005/010049 A2 | 2/2005 |
| WO | WO 2005/097832 A2 | 10/2005 |
| WO | WO 2006/086469 A2 | 8/2006 |
| WO | WO2011/109789 A2 | 9/2011 |
| WO | WO 2012/145493 A1 | 10/2012 |
| WO | WO 2014/153435 A1 | 9/2014 |
| WO | WO 2015/035606 A1 | 3/2015 |

(Continued)

OTHER PUBLICATIONS

MacCallum, R.M., et al. Antibody-antigen interations: Contact analysis and binding site topography. J. Mol. Biol., 1998, 262:732-745.*

(Continued)

*Primary Examiner* — Joanne Hama
*Assistant Examiner* — Bruce D. Hissong
(74) *Attorney, Agent, or Firm* — Steptoe & Johnson LLP; Z. Ying Li; Mauricio Alvarez

(57) ABSTRACT

The invention provides an improved pan-TGF-β antibody for treatment of conditions that are mediated by TGF-β, including autoimmune diseases, fibrotic conditions, and cancers. Also provided are methods and uses of the antibody in conjunction with other immunomodulatory agents such as an anti-PD-1 antibody.

33 Claims, 29 Drawing Sheets

Specification includes a Sequence Listing.

(56) References Cited

FOREIGN PATENT DOCUMENTS

| WO | WO 2015/112800 A1 | 7/2015 |
|---|---|---|
| WO | WO 2015/112900 A1 | 7/2015 |
| WO | WO2015/140150 A1 | 9/2015 |
| WO | WO2016/057933 A1 | 4/2016 |
| WO | WO 2016/061142 A1 | 4/2016 |
| WO | WO 2016/092419 A1 | 6/2016 |
| WO | WO2016/123573 A1 | 8/2016 |
| WO | WO2016/161410 A2 | 10/2016 |
| WO | WO 2017/011773 A2 | 1/2017 |
| WO | WO 2017/037634 A1 | 3/2017 |

OTHER PUBLICATIONS

Vajdos, F.F. et al. Comprehensive functional maps of the antigen-binding site of anti-ErbB2 antibody obtained with shotgun scanning mutagenesis. J. Mol. Biol., 2002, 320:415-428.*
Wu, H., et al. Humanization of a murine monoclonal antibody by simultaneous optimization of framework and CDR residues. J. Mol. Biol., 1999, 294:151-162.*
Thomson Pharma literature and new report, 2010. https://media.nature.com/original/nature-assets/nbt/journal/v28/n2/extref/nbt0210-123-S1.pdf, 4 pages.*
Yang, J., et al. The role of mesenchymal stem/progenitor cells in sarcoma: update and dispute. Stem Cell Investigation, 2104, 1:18.*
Lewis, K.B., et al. Comparision of the ability of wild-type and stabilized human IgG4 to undergo Fab arm exchange with endogenous IgG4 in vitro and in vivo. Molecular Immunology, 2009, 46:3488-3494.*
Aalberse et al., "IgG4 breaking the rules," Immunology, 105:9-19 (2002).
Akhurst et al., "Targeting the TGFβ signalling pathway in disease," Nat Rev Drug Discov 11(10):790-811 (2012).
Angal el al., "A single amino acid substitution abolishes the heterogeneity of chimeric mouse/human (IgG4) antibody," Mol Immunol 30(1):105-8 (1993).
Arteaga et al., "Anti-transforming growth factor (TGF)-β antibodies inhibit breast cancer cell tumorigenicity and increase mouse spleen natural killer cell activity. Implications for a possible role of tumor cell/host TGF-beta interactions in human breast cancer progression," J Clin Invest 92:2569-2576 (1993).
Becht et al., "Cancer immune contexture and immunotherapy," Curr Opin Immunol 39:7-13 (2016).
Becht et al., "Estimating the population abundance of tissue-infiltrating immune and stromal cell populations using gene expression," Genome Biol 17:218 (2016).
Bedinger et al., "Development and characterization of human monoclonal antibodies that neutralize multiple TGFβ isoforms," MAbs. 8(2):389-404 (2016).
Bloom et al., "Intrachain disulfide bond in the core hinge region of human IgG4," Protein Science 6:407-415 (1997).
Bonewald, "Regulation and regulatory activities of transforming growth factor β," Crit Rev Eukaryot Gene Expr. 9(1):33-44 (1999).
Border et al., "Fibrosis linked to TGF-β in yet another disease," J Clin Invest 96:655-656 (1995).
Border et al., "Suppression of experimental glomerulonephritis by antiserum against transforming growth factor β1," Nature 346:371-374 (1990).
Border et al., "Transforming growth factor β in tissue fibrosis," New Eng. J Med. 331(19):1286-1292 (1994).
Border et al., "Targeting TGF-β for treatment of disease," Nat. Med. 1(10):1000-1001 (1995).
Border et al., "TGF-β," Scientific American—Science & Medicine 68-77 (Jan./Feb. 1995).
Connolly et al., "Complexities of TGF-β targeted cancer therapy," Int J Biol Sci 8(7):964-78 (2012).
Cuende et al., "Monoclonal antibodies against GARP/TGF-β1 complexes inhibit the immunosuppressive activity of human regulatory T cells in vivo," Sci Transl Med. 7:284ra56 (2015).

Dalal et al., "Immunocytochemical localization of secreted transforming growth factor-$β_1$ to the advancing edges of primary tumors and to lymph node metastases of human mammary carcinoma", American Journal of Pathology 143:381-389 (1993).
Danielpour et al., "Immunodetection and quantitation of the two forms of transforming growth factor-beta (TGF-β1 and TGF-β2) secreted by cells in culture," J Cell. Physiol. 138:79-86 (1989).
Danielpour et al., "Sandwich enzyme-linked immunosorbent assays (SELISAs) quantitate and distinguish two forms of transforming growth factor-beta (TGF-β1 and TGF-β2) in complex biological fluids," Growth Factors 2:61-71 (1989).
Dasch et al., "Monoclonal antibodies recognizing transforming growth factor-β. Bioactivity neutralization and transforming growth factor β2 affinity purification," The Journal of Immunology 142(5):1536-1541 (1989).
Davies et al., "Human IgG4: a structural perspective," Immunological Reviews 268:139-159 (2015).
Feyler et al., "Tumour cell generation of inducible regulatory T-cells in multiple myeloma is contact-dependent and antigen-presenting cell-independent," PLoS One 7(5):e35981, 11 pages (2012).
Flanders et al., "Antibodies to peptide determinants in transforming growth factor β and their applications," Biochemistry 27:739-746 (1988).
Flavell et al., "The polarization of immune cells in the tumour environment by TGFβ," Nature Reviews Immunology 10:554-567 (2010).
Fridman et al., "The immune contexture in human tumours: impact on clinical outcome," Nat Rev Cancer 12(4):298-306 (2012).
Friedman et al., "high levels of transforming growth factor β1 correlate with disease progression in human colon cancer," Cancer Epidemiology, Biomarkers & Prevention 4: 549-554 (1995).
Galon et al., "The continuum of cancer immunosurveillance: prognostic, predictive, and mechanistic signatures," Immunity 39(1):11-26 (2013).
Girt et al., "Effect of antibody to transforming growth factor β on bleomycin induced accumulation of lung collagen in mice," Thorax 48:959-966 (1993).
Griffith et al., "Three-dimensional structure of recombinant human osteogenic protein 1: structural paradigm for the transforming growth factor B superfamily," Proc. Natl. Acad. Sci. USA, 93:878-883 (1996).
Hirashima et al., "Transforming growth factor-β1 produced by ovarian cancer cell line HRA stimulates attachment and invasion through an up-regulation of plasminogen activator inhibitor Type-1 in human peritoneal mesothelial cells," Journal of Biological Chemistry 278: 26793-26802 (2003).
Hocevar et al., "TGF-β induces fibronectin synthesis through a c-Jun N-terminal kinase-dependent, Smad4-independent pathway," The EMBO Journal 18(5): 1345-1356 (1999).
Hoefer et al., "Anti-(transforming growth factor β) antibodies with predefined specificity inhibit metastasis of highly tumorigenic human xenotransplants in nu/nu mice," Cancer Immunol Immunother 41:302-308 (1995).
Hugo et al., "Genomic and transcriptomic features of response to anti-PD-1 therapy in metastatic melanoma," Cell 165:35-44 (2016).
Ignotz et al., "Transforming growth factor-β stimulates the expression of fibronectin and collagen and their incorporation into the extracellular matrix," J Biol. Chem. 261(9):4337-4345 (1986).
Ikeda et al., "The roles of IFN gamma in protection against tumor development and cancer immunoediting," Cytokine Growth Factor Rev 13:95-109 (2002).
Jackson, "Modulation of the activity of transforming growth factor beta," Expert Opinion on Therapeutic Patents 8(11):1479-1486 (1998).
Kadam et al., "A canonical transforming growth factor β-dependent signaling pathway is present in peripheral blood cells of cancer patients with skeletal metastasis," Journal of Molecular Biomarkers & Diagnosis 4:153 (2013).
Khanna et al., "Transforming growth factor (TGF)-β mimics and anti-TGF-β antibody abrogates the in vivo effects of cyclosporine," Transplantation 67(6):882-889 (1999).

(56) References Cited

OTHER PUBLICATIONS

Kim et al., "Multi-cellular natural killer (NK) cell clusters enhance NK cell activation through localizing IL-2 within the cluster," Scientific Reports 7:40623 (2017).
Kjellman et al., "Expression of TGF-β isoforms, TGF-β receptors, and SMAD molecules at different stages of human glioma," Int. J. Cancer (Pred. Oncol.) 89: 251-258 (2000).
Labrijn et al., "Therapeutic IgG4 antibodies engage in Fab-arm exchange with endogenous human IgG4 in vivo," Nature Biotechnology 27: 767-773 (2009).
Lan et al., "Enhanced preclinical antitumor activity of M7824, a bifunctional fusion protein simultaneously targeting PD-L1 and TGF-β," Sci Transl Med. 10(424) (2018).
Larkin et al, "Combined Nivolumab and Ipilimumab or Monotherapy in Untreated Melanoma," N Engl J Med 373:23-34 (2015).
Leask et al., "TGF-β signaling and the fibrotic response," FASEB J 18:816-827 (2004).
Lee et al., "Transforming growth factor β induces vascular endothelial growth factor elaboration from pleural mesothelial cells in vivo and in vitro," Am J Respir Crit Care Med 165:88-94 (2002).
Lei et al., "Autocrine TGFβ supports growth and survival of human breast cancer MDA-MB-231 cells," Oncogene 21:7514-7523 (2002).
Lewis et al., "Tumour-derived TGF-β1 modulates myofibroblast differentiation and promotes HGF/SF-dependent invasion of squamous carcinoma cells," British Journal of Cancer 90:822-832 (2004).
Lin et al., "Regulation of fibronectin by thyroid hormone receptors," J Mol Endocrinol 33:445-458 (2004).
Ling et al., "Therapeutic role of TGF-β-neutralizing antibody in mouse cyclosporin A nephropathy: Morphologic improvement associated with functional preservation," J Am. Soc. Nephrol. 14:377-388 (2003).
Liu et al., "Neutralizing TGF-β1 antibody infusion in neonatal rat delays in vivo glomerular capillary formation," Kidney Int 56:1334-1348 (1999).
Logan et al., "Effects of transforming growth factor $β_1$ on scar production in the injured central nervous system of the rat," Eur. J Neurosci. 6:355-363 (1994).
Lucas et al., "The autocrine production of transforming growth factor-β1 during lymphocyte activation—A study with a monoclonal antibody-based Elisa," The Journal of Immunology 145(5):1415-1422 (1990).
Lyons et al., "Transforming growth factors and the regulation of cell proliferation," Eur J Biochem 187:467-473 (1990).
Ma et al., "Progress of immunotherapy for hepatocellular carcinoma", Immuno-Gastroenterology 2(3):167-172 (2013).
Malaspina et al., "Enhanced programmed death 1 (PD-1) and PD-1 ligand (PD-L1) expression in patients with actinic cheilitis and oral squamous cell carcinoma," Cancer Immunol Immunother 60:965-974 (2011).
Mariathasan et al., "TGF-B Signalling Attenuates Tumour Response to PD-L1 Checkpoint Blockade by Contributing to Retention of T Cells in the Peritumoural Stroma," Abstract 8O_PR, ESMO Immuno Oncology Congress, European Society for Medical Oncology, 16-17 (2017).
Massagué, "TGFβ in cancer," Cell 134(2): 215-230 (2008).
Mittl et al., "The crystal structure of TGF-β3 and comparison to TGF-β2: Implications for receptor binding," Protein Science 5:1261-1271 (1996).
Miyajima et al., "Antibody to transforming growth factor-β ameliorates tubular apoptosis in unilateral ureteral obstruction," Kidney Int. 58:2301-2313 (2000).
Mookerjee et al., "Immunosuppression in hamsters with progressive visceral leishmaniasis is associated with an impairment of protein kinase C activity in their lymphocytes that can be partially reversed by okadaic acid or anti-transforming growth factor B antibody," Infection and Immunity 71:2439-2446 (2003).
Morris et al., "Phase I study of GC1008 (Fresolimumab): A human anti-transforming growth factor-beta (TGFβ) monoclonal antibody in patients with advanced malignant melanoma or renal cell carcinoma," PLoS One 9:e90353 (2014).
Newman et al., "Modification of the Fc region of a primatized IgG antibody to human CD4 retains its ability to modulate cd4 receptors but does not deplete CD4+ T cells in chimpanzees," Clinical Immunology 98:164-174(2001).
Pardoll, "Cancer immunotherapy through checkpoint blockade: the future of cancer treatment," Medicographia 36:274-284 (2014).
Peters et al., "Targeting TGFβ overexpression in renal disease: maximizing the antifibrotic action of angiotensin II blockade," Kidney Int 54:1570-1580 (1998).
Pintavorn et al., "TGF-β and the endothelium during immune injury," Kidney Int 51:1401-1412 (1997).
Redman et al., "Advances in immunotherapy for melanoma," BMC Med 14:20-30 (2016).
Rispens et al., "Mechanism of Immunoglobulin G4 Fab-arm Exchange," J. Am. Chem. Soc. 133:10302-10311 (2011).
Salas-Solano et al., "Optimization and validation of a quantitative capillary electrophoresis sodium dodecyl sulfate method for quality control and stability monitoring of monoclonal antibodies," Anal Chem 78:6583-94 (2006).
Santarpia et al., "Programmed cell death protein-1/programmed cell death ligand-1 pathway inhibition and predictive biomarkers: understanding transforming growth factor-beta role," Transl Lung Cancer Res 4(6):728-742 (2015).
Schneider et al., "Monocyte chemoattractant protein-1 mediates collagen deposition in experimental glomerulonephritis by transforming growth factor-β," Kidney Int. 56:135-144 (1999).
Schuurman et al., "The inter-heavy chain disulfide bonds of IgG4 are in equilibrium with intra-chain disulfide bonds," Mol Immunol. 38(1):1-8 (2001).
Schuurman, "IgG4 Fab-arm exchange," 28 pages, Copenhagen Oct. 27, 2010.
Shah et al., "Neutralising antibody to TGF-$β_{1,2}$ reduces cutaneous scarring in adult rodents," J Cell. Sci. 107:1137-1157 (1994).
Shenkar et al., "Anti-transforming growth factor-β monoclonal antibodies prevent lung injury in hemorrhaged mice," Am. J Respir. Cell. Mol. Biol. 11:351-357 (1994).
Silva et al., "The S228P mutation prevents in vivo and in vitro IgG4 Fab-arm exchange as demonstrated using a combination of novel quantitative immunoassays and physiological matrix preparation," J Biol Chem. 290:5462-9 (2015).
Sinha et al., "Transforming growth factor-β1 signaling contributes to development of smooth muscle cells from embryonic stem cells," Am J Physiol Cell Physiol 287:C1560-C1568 (2004).
Tahara et al., "Synthetic peptide-generated monoclonal antibodies to transforming growth factor-β1," Hybridoma 12(4):441-453 (1993).
Tauriello et al., "TGFβ drives immune evasion in genetically reconstituted colon cancer metastasis," Nature 554(7693):538-543 (2018).
Tempest et al., "Human antibodies specific for human TGF-β derived from phage display libraries," Immunotechnology 2:306 (1996).
Terabe et al., "Blockade of only TGF-β 1 and 2 is sufficient to enhance the efficacy of vaccine and PD-1 checkpoint blockade immunotherapy," Oncoimmunology 6:e1308616 (2017).
Thompson et al., "A fully human antibody neutralising biologically active human TGFB2 for use in therapy," Journal of Immunological Methods 227:17-29 (1999).
Trotta et al., "TGF-beta utilizes SMAD3 to inhibit CD16-mediated IFN-gamma production and antibody-dependent cellular cytotoxicity in human NK cells," Journal of immunology 181:3784-3792 (2008).
Vanpouille-Box et al., "TGFβ is a master regulator of radiation therapy-induced antitumor immunity," Cancer Res 75(11):2232-2242 (2015).
Wang et al., "Transforming growth factor-β1 stimulates vascular endothelial growth factor 164 via mitogen-activated protein kinase kinase 3-p38α and p38δ mitogen-activated protein kinase-dependent pathway in murine mesangial cells," J Biol Chem 279:33213-33219 (2004).
Weeks et al., "Inducible expression of transforming growth factor β1 in papillomas causes rapid metastasis," Cancer Research 61:7435-7443 (2001).

(56) References Cited

OTHER PUBLICATIONS

Yang et al., "Comprehensive analysis of the therapeutic IgG4 antibody pembrolizumab: hinge modification blocks half molecule exchange in vitro and in vivo," Journal of Pharmaceutical Sciences 104:4002-4014 (2015).
Yingling et al., "Development of TGF-β signaling inhibitors for cancer therapy," Nature Review/Drug Discovery 3:1011-1022 (2004).
Jiang et al., "Signatures of T cell dysfunction and exclusion predict cancer immunotherapy response," Nature Medicine (2018).
Labrijn et al., "Species-Specific Determinants in the IgG CH3 Domain Enable Fab-Arm Exchange by Affecting the Noncovalent CH3—CH3 Interaction Strength," J Immunol. 187(6):3238-46 (2011).

\* cited by examiner

Effect of Ab1 on human inducible regulatory T cell differentiation in cultures treated with 2 ng/ml TGF-β1

ANTI-TGF-β ANTIBODIES AND THEIR USE

CROSS REFERENCE TO RELATED APPLICATIONS

This application claims priority from U.S. Provisional Application 62/448,800 and European Application No. 17305061.8, both filed on Jan. 20, 2017. The disclosures of the two priority applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 11, 2018, is named 022548_US011_SL.txt and is 30,237 bytes in size.

BACKGROUND OF THE INVENTION

Transforming growth factor beta (TGF-β) is a cytokine that controls many key cellular functions including proliferation, differentiation, survival, migration, and epithelial mesenchymal transition. It regulates diverse biologic processes, such as extracellular matrix formation, wound healing, embryonic development, bone development, hematopoiesis, immune and inflammatory responses, and malignant transformation. Deregulation of TGF-β leads to pathological conditions, e.g., birth defects, cancer, chronic inflammation, and autoimmune and fibrotic diseases.

TGF-β has three known isoforms—TGF-β1, 2, and 3. All three isoforms are initially translated as a pro-peptide. After cleavage, the mature C-terminal end remains associated with the N-terminus (called the latency associated peptide or LAP), forming the small latent complex (SLC), which is secreted from the cell. The inability of the SLC to bind to TGF-β receptor II (TGFβRII) prevents receptor engagement. Activation by dissociation of the N- and C-termini occurs by one of several mechanisms, including proteolytic cleavage, acidic pH, or integrin structural alterations (Connolly et al., Int J Biol Sci (2012) 8(7):964-78).

TGF-β1, 2, and 3 are pleiotropic in their function and expressed in different patterns across cell and tissue types. They have similar in vitro activities, but individual knockouts in specific cell types suggest non-identical roles in vivo despite their shared ability to bind to the same receptor (Akhurst et al., Nat Rev Drug Discov (2012) 11(10):790-811). Upon TGF-β binding to TGFβRII, the constitutive kinase activity of the receptor phosphorylates and activates TGFβRI, which phosphorylates SMAD2/3, allowing for association to SMAD4, localization to the nucleus, and transcription of TGF-β-responsive genes. Id. In addition to this canonical signaling cascade, a non-canonical pathway transmits signals through other factors including p38 MAPK, PI3K, AKT, JUN, JNK, and NF-κB. TGF-β signaling is also modulated by other pathways, including WNT, Hedgehog, Notch, INF, TNF, and RAS. Thus the end result of TGF-β signaling is a crosstalk of all of these signaling pathways that integrates the state and environment of the cell. Id.

Given the diverse functions of TGF-β, there is a need for pan-TGF-β-specific therapeutic antibodies safe for human patients (Bedinger et al., mAbs. (2016) 8(2):389-404). However, TGF-β is highly conserved among species. As a result, production of antibodies to human TGF-βs in animals such as mice is a challenging task.

There is also a medical need for patients for whom there is currently no effective treatment. For example, more than 50% of advanced melanoma patients in Phase III Checkmate-067 study treated with the anti-PD1 antibody nivolumab monotherapy did not have complete or partial response to the therapy (Larkin et al., N Engl J Med (2015) 373:23-34; Redman et al., BMC Med (2016) 14:20-30).

SUMMARY OF THE INVENTION

The present invention provides improved monoclonal antibodies that bind specifically to human TGF-β1, TGF-β2, and TGF-β3 (i.e., pan-TGF-β-specific). These antibodies are less prone to form half antibody (i.e., a dimeric complex having one heavy chain and one light chain) during manufacturing. They also have superior pharmacokinetic profiles such as an increased half-life and thus may confer improved clinical benefits to patients. The inventors have also discovered that TGF-β inhibition, such as that effected by the antibodies and antigen-binding fragments of the present invention, alleviates the immunosuppressive microenvironment in tumors and potentiates the efficacy of immunotherapy such as therapy targeting programmed cell death protein 1 (PD-1), PD-1 ligands 1 (PD-L1) and 2 (PD-L2).

In one aspect, the present invention provides an isolated monoclonal antibody that binds specifically to human TGF-β1, TGF-β2, and TGF-β3, comprising the heavy chain complementarity-determining regions (CDR) 1-3 in SEQ ID NO:1 and the light chain CDR1-3 in SEQ ID NO:2, wherein the antibody comprises a human IgG$_4$ constant region having a mutation at position 228 (EU numbering). In some embodiments, the mutation is a serine-to-proline mutation (S228P). In some embodiments, the antibody comprises a heavy chain variable domain ($V_H$) amino acid sequence corresponding to residues 1-120 of SEQ ID NO:1 and a light chain variable domain ($V_L$) amino acid sequence corresponding to residues 1-108 of SEQ ID NO:2. In further embodiments, the antibody comprises a heavy chain amino acid sequence set forth in SEQ ID NO:1 (with or without the C-terminal lysine) and a light chain amino acid sequence set forth in SEQ ID NO:2. The invention also features an F(ab')$_2$ antigen-binding fragment of the above antibody.

In preferred embodiments, the antibody or fragment of the present invention has an increased half-life, an increased exposure, or both, as compared to fresolimumab. For example, the increase is a 10%, 20%, 30%, 40%, 50%, 60%, 70%, 80%, 90%, or 100% or more increase. The exposure of a drug such as an antibody or fragment of the present invention is a function of the concentration of the drug in the body with respect to time. The concentration of the drug in the body often is indicated by the level of the drug in the blood, plasma, or serum. Half-life and exposure (bio-exposure) of a drug can be measured by well-known methods, as illustrated in Example 7 below.

The invention further provides a composition comprising the antibody of the present invention, wherein the composition comprises less than 1% of half antibody. The half antibody formation may be determined through purity analysis of monoclonal antibody preparations by using, for example, SDS-capillary electrophoresis under non-reducing conditions or non-reducing SDS-PAGE analysis, followed by densitometry, or RP-HPLC (Angal et al., Mol Immunol (1993) 30(1):105-8; Bloom et al., Protein Science (1997) 6:407-415; Schuurman et al., (2001) 38(1):1-8; and Solanos et al., Anal Chem (2006) 78:6583-94). In some embodiments, this composition is a pharmaceutical composition comprising also a pharmaceutically acceptable excipient.

In another aspect, the invention provides a method of inhibiting TGF-β signal transduction in a patient (human) in need thereof, comprising administering to the patient a therapeutic amount of the antibody or fragment of the present invention. In some embodiments, the patient has an immune-mediated disease (e.g., scleroderma), a fibrotic condition (e.g., a renal fibrotic condition such as focal segmental glomerulosclerosis (FSGS), or a lung fibrotic condition such as idiopathic pulmonary fibrosis), or a birth or bone defect (e.g., osteogenesis imperfecta). In some embodiments, the patient has cancer. In some embodiments, the antibody or fragment used in the method inhibits the differentiation of CD4+ T cells into inducible regulatory T cells (iTreg). The antibody or fragment may alleviate the immunosuppressive tumor microenvironment. This action of the antibody or fragment helps activate the immune system and potentiates the efficacy of immunotherapy. Efficacy of the treatment methods described herein may be indicated by, for example, one or more of the following in the patient (e.g., in the tumor tissue of the patient): (1) an increase in MIP2 and/or KC/GRO levels, (2) activation or infiltration to the tumor tissue of CD8+ T cells such as INF-γ-positive CD8+ T cells, and (3) an increase in clustering of natural killer (NK) cells.

The present invention further provides a method of treating cancer in a patient (human), comprising administering to the patient (1) a therapeutic effective amount of the antibody or fragment of the present invention, and (2) a therapeutic effective amount of an inhibitor of an immune checkpoint protein. These two agents can be administered concurrently (e.g., in a single composition or in separate compositions), or sequentially in either order. The two agents can, for example, be administered on the same day. In some embodiments, therapeutic agent (1) is administered to the patient before (e.g., one or more days before) therapeutic agent (2).

In some embodiments, the immune checkpoint protein is PD-1, PD-L1, or PD-L2. In further embodiments, the inhibitor of the immune checkpoint protein is an anti-PD-1 antibody. In further embodiments, the anti-PD-1 antibody comprises (1) the heavy chain CDR1-3 in SEQ ID NO:5 and the light chain CDR1-3 in SEQ ID NO:6, (2) a $V_H$ amino acid sequence corresponding to residues 1-117 of SEQ ID NO:5 and a $V_L$ amino acid sequence corresponding to residues 1-107 of SEQ ID NO:6, or (3) a heavy chain amino acid sequence set forth in SEQ ID NO:5 (with or without the C-terminal lysine) and a light chain amino acid sequence set forth in SEQ ID NO:6. In one particular embodiment, the method comprises administering to the cancer patient an anti-TGF-β antibody comprising a heavy chain amino acid sequence set forth in SEQ ID NO:1 (with or without the C-terminal lysine) and a light chain amino acid sequence set forth in SEQ ID NO:2, and an anti-PD-1 antibody comprising a heavy chain amino acid sequence set forth in SEQ ID NO:5 (with or without the C-terminal lysine) and a light chain amino acid sequence set forth in SEQ ID NO:6. In some embodiments, the patient is refractory to anti-PD-1 antibody monotherapy. The patient may have advanced or metastatic melanoma, or cutaneous squamous cell carcinoma.

In some regimens, the anti-TGF-β antibody and the anti-PD-1 antibody are administered every 2 weeks or every 3 weeks to the patient. In some regimens, the two agents are administered respectively at a dose of 0.01-40 (e.g., 0.02-20, 0.05-15, or 0.05-20) mg/kg body weight.

The present invention also provides a method of increasing an immune response in a patient in need thereof, comprising administering to the patient an immune checkpoint inhibitor and the antibody or fragment of the present invention. In some embodiments, the immune checkpoint inhibitor is an anti-PD-1 antibody, such as one comprising (1) the HCDR1-3 in SEQ ID NO:5 and the LCDR1-3 in SEQ ID NO:6; (2) a VH and a VL corresponding to residues 1-117 in SEQ ID NO:5 and residues 1-107 in SEQ ID NO:6, respectively; or (3) a heavy chain having the amino acid sequence of SEQ ID NO:5 (with or without the C-terminal lysine) and a light chain having the amino acid sequence of SEQ ID NO:6.

The methods of the present invention can be used to treat a variety of cancers, including, without limitation, melanoma (e.g., metastatic or advanced), lung cancer (e.g., non-small cell lung cancer), cutaneous squamous cell carcinoma, colorectal cancer, breast cancer, ovarian cancer, fallopian cancer, uterine cancer, head and neck cancer (e.g., head and neck squamous cell carcinoma), liver cancer (e.g., hepatocarcinoma), urothelial cancer, and kidney cancer (e.g., renal cell carcinoma). In some embodiments, the patient has a mesenchymal tumor or a mesenchymal subtype of a solid tumor. Examples of such a solid tumor include those in the colon (e.g., colorectal cancer), ovary, head and neck (e.g., head and neck squamous cell carcinoma), liver (e.g., hepatocellular carcinoma), and the urothelial system.

In some embodiments, the cancer, including a mesenchymal tumor, may be characterized by overexpression of one or more of ACTA2 (smooth muscle α2 actin), VIM (vimentin), MGP (Matrix Gla Protein), ZWINT (ZW10 Interacting Kinetochore Protein), and ZEB2 (Zinc finger E-box-binding homeobox 2). The expression levels of such biomarkers may be determined, for example, at the mRNA level or protein level in a biological sample from the patient, such as a tumor biopsy or circulating tumor cells.

The present invention also provides the aforementioned antibodies, fragments, or compositions for use in treating the conditions described herein, as well as the use of the aforementioned antibodies, fragments, or compositions in the manufacture of medicaments for treatment of the conditions described herein.

Also included in the invention are nucleic acid expression vectors encoding the heavy or light chain, or both, of an antibody of the invention; host cells comprising the heavy chain and light chain coding sequences for the antibody; and methods of making the antibody using the host cells comprising the steps of culturing the host cells in appropriate culture medium to allow expression of the antibody genes and then harvesting the antibody.

DETAILED DESCRIPTION OF THE INVENTION

Figure 1A:
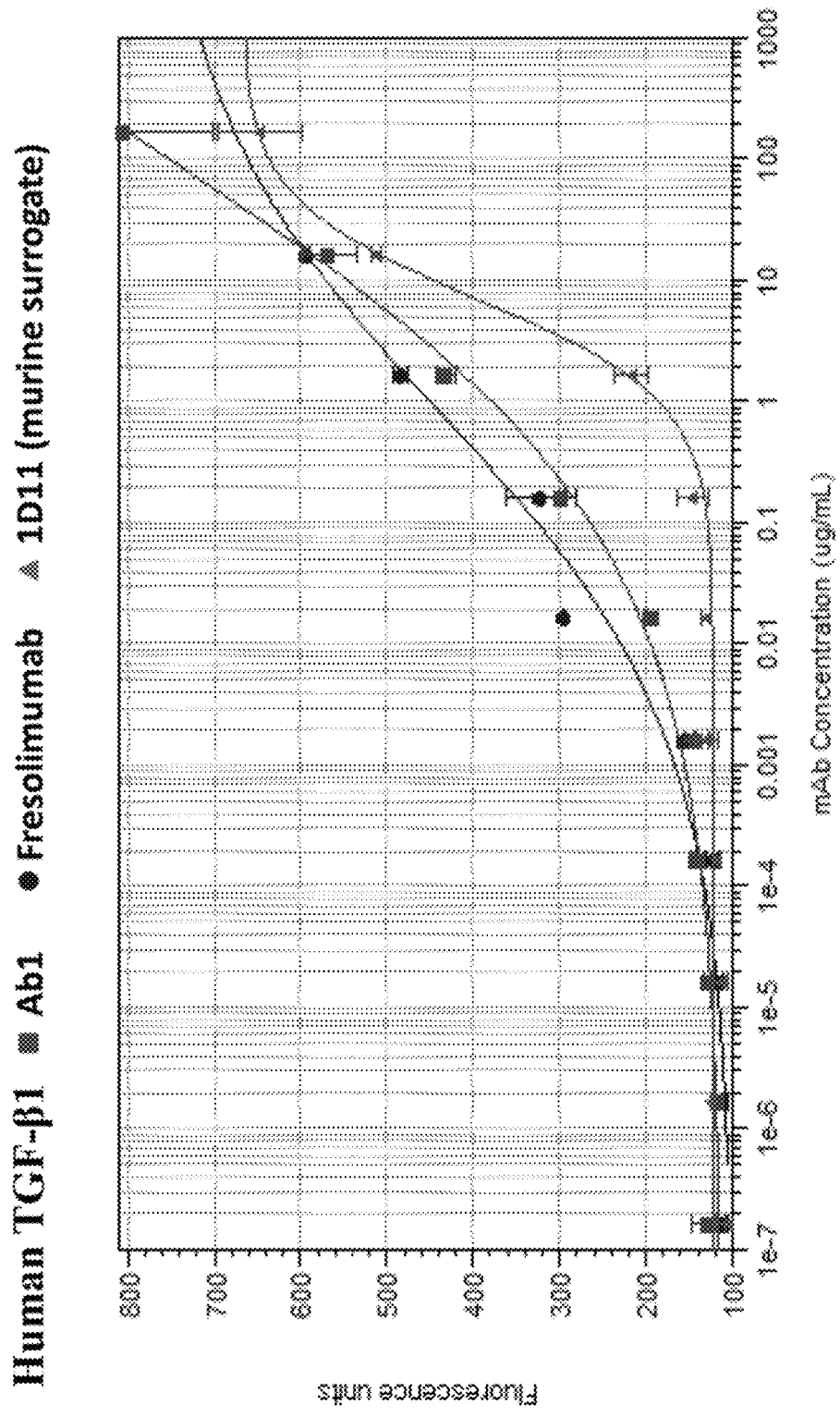
FIGS. 1A-E are graphs showing the effects of Ab1, fresolimumab, and 1D11 on the proliferation of mink lung (Mv 1 Lu) cells treated with 1 ng/ml of human TGF-β1 (A), human TGF-β2 (B), human TGF-β3 (C), murine TGF-β1 (D), or murine TGF-β2 (E). The antibody concentration is in μg/ml.
Figure 1B:
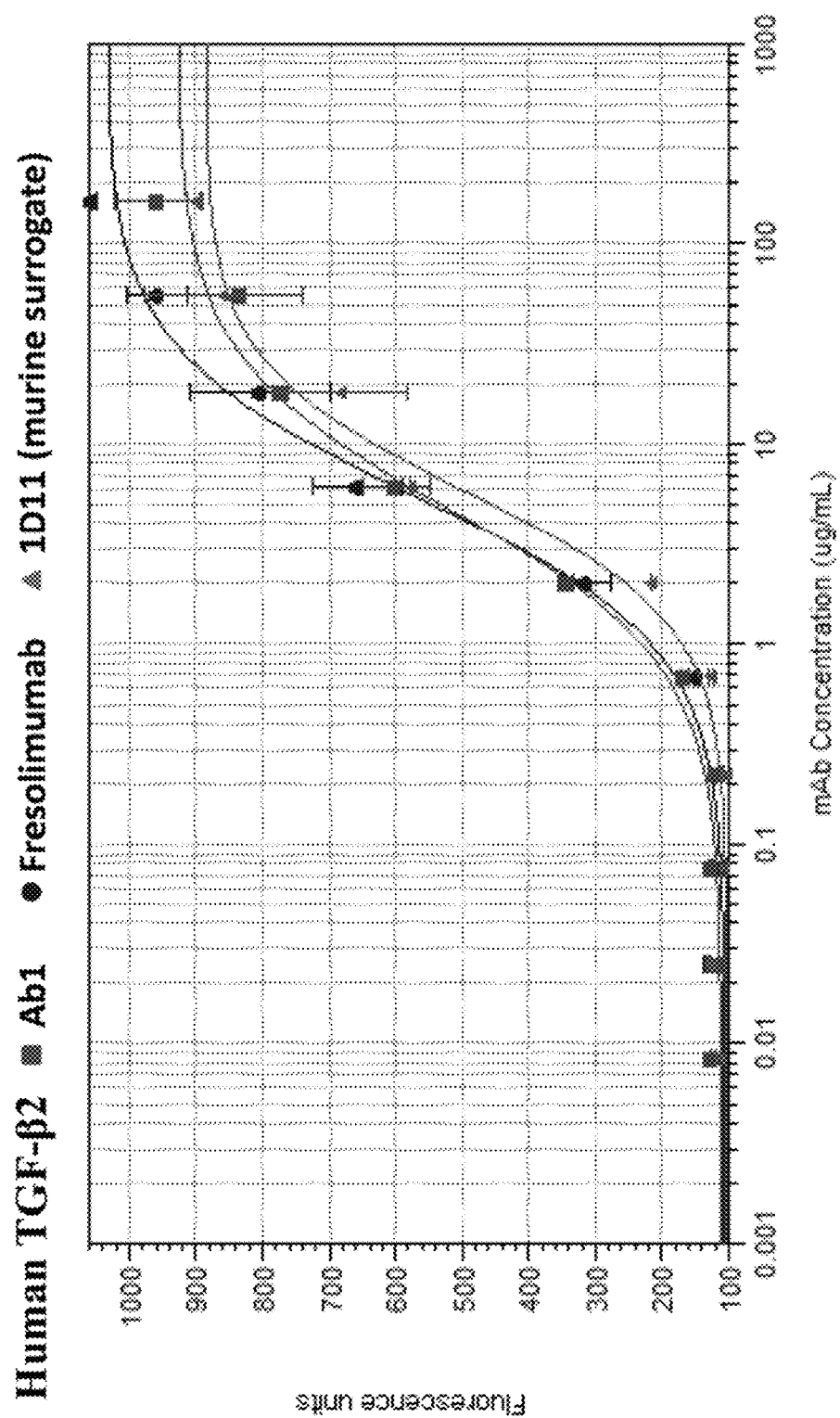
Figure 1C:
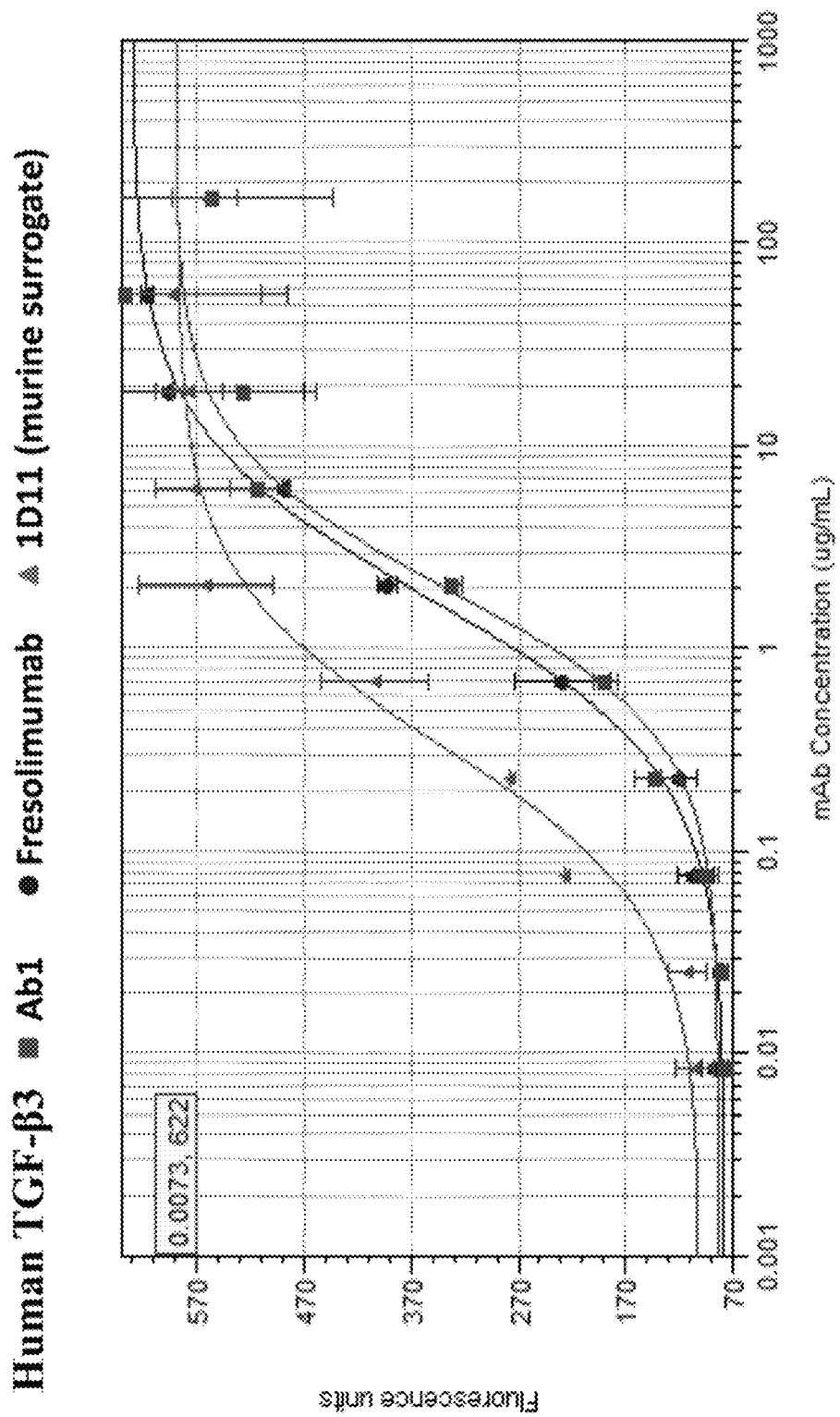
Figure 1D:
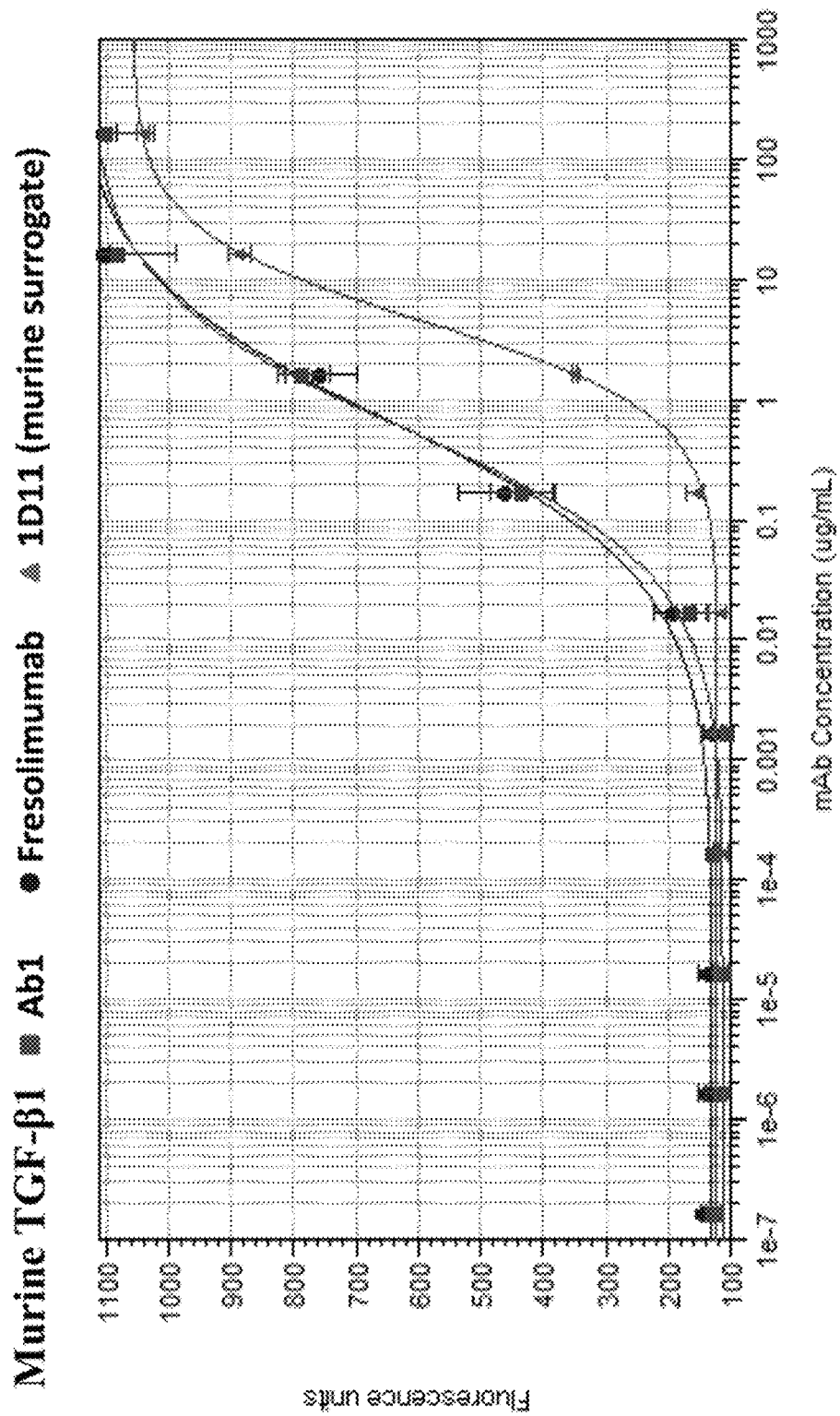
Figure 1E:
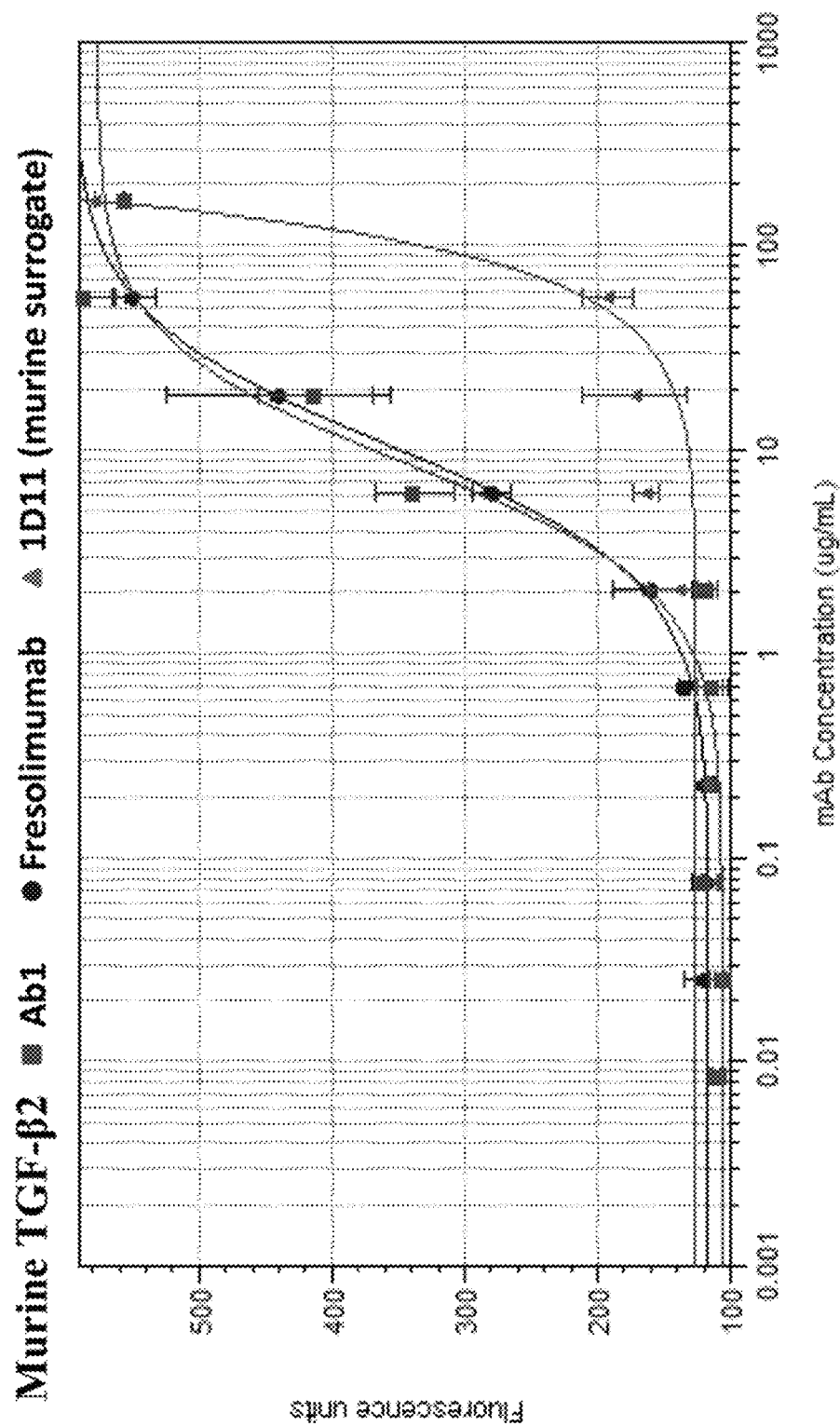

The present invention features improved pan-TGF-β-specific monoclonal antibodies that are less prone to form half antibody while also having superior pharmacokinetic profiles such as higher exposure in the body than prior known antibodies. The present antibodies are collectively called "Ab1 and related antibodies" and share the common structure characteristics that they have the heavy chain CDR (HCDR) 1-3 in SEQ ID NO:1 and the light chain CDR (LCDR) 1-3 in SEQ ID NO:2, and have a human IgG$_4$ constant region where residue 228 (EU numbering) in the hinge region has been mutated from serine to proline. P228 is in box and boldface in the sequence of SEQ ID NO: 1 shown below.

Antibody Ab1 has an estimated molecular weight of 144 KD when un-glycosylated. Its heavy and light amino acid sequences are SEQ ID NOs:1 and 2, respectively. These two sequences are shown below. Variable domains are italicized. CDRs are shown in boxes. The glycosylation site in the constant domain of the heavy chain is in boldface (N297).

(SEQ ID NO: 1)

*QVQLVQSGAE VKKPGSSVKV SCKASGYTFS* SNVIS *WVRQA PGQGLEWMG* G VIPIVDIANY
AQRFKG *RVTI TADESTSTTY MELSSLRSED TAVYYCAS* TL GLVLDAMDY *W GQGTLVTVSS*
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK (SEQ ID NO: 2)

*ETVLTQSPGT LSLSPGERAT LS* RASQSLG SSYLA *WYQQK PGQAPRLLIY* GASSRAP *GIP*
*DRFSGSGSGT DFTLTISRLE PEDFAVYYC* Q QYADSPIT *FG QGTRLEIK*RT VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC

In some embodiments, the antibodies of the present invention, such as the anti-TGF-β antibodies, do not have the C-terminal lysine in the heavy chain. The C-terminal lysine may be removed during manufacture or by recombinant technology (i.e., the coding sequence of the heavy chain does not include a codon for the C-terminal terminal lysine). Thus contemplated within the invention also are antibodies comprising the heavy chain amino acid sequence of SEQ ID NO: 1 without the C-terminal lysine.

Ab1 and related antibodies bind specifically to human TGF-β1, -β2, and -β3. By "specifically," we mean that the binding has a $K_D$ less than $10^{-7}$ M, such as less than $10^{-8}$ M (e.g., 1-5 nM), as determined by, e.g., surface plasmon resonance (see, e.g., Example 1 below), or Bio-Layer Interferometry. Ab1 and related antibodies also may have a strong TGF-β neutralizing potency when assayed in a mink lung epithelial cell assay (see, e.g., Example 2 below), or an EC50 of about 0.05 to 1 μg/ml as determined in an A549 cell IL-11 induction assay (see, e.g., Example 6 in PCT Publication WO 2006/086469, whose disclosure is incorporated by reference herein in its entirety).

These antigen-binding and neutralizing properties of Ab1 and related antibodies are comparable to prior anti-TGF-β antibody fresolimumab (a germlined IgG$_4$ PET1073G12 antibody described in WO 2006/086469). Fresolimumab's heavy and light chain sequences, including the leader sequences, are shown in SEQ ID NOs:3 and 4, respectively. As seen in SEQ ID NO:3, fresolimumab does not have a proline at position 228 (EU numbering, which corresponds to actual position 247 in SEQ ID NO:3). Ab1 and related antibodies have several improved features over fresolimumab.

During manufacturing, fresolimumab may form as much as 6-18% half antibody (i.e., a dimer having a heavy chain and a light chain, rather than a tetramer having two heavy chains complexed with two light chains) under non-reducing denaturing conditions. By contrast, Ab1 yields substantially less half antibody (<1%). Thus, Ab1 and related antibodies give rise to purer drug product during manufacturing.

Further, Ab1 and related antibodies may have improved pharmacokinetic (PK) profiles over fresolimumab. They may have linear PK behavior with a much longer half-life and a lower elimination rate than fresolimumab, leading to about 1.7-folder higher exposure in vivo than fresolimumab. For example, in rats, Ab1 have been shown to have an average half-life of 7.1 days, compared to fresolimumab's 4.3 days, and an elimination rate (CL) of 0.30 ml/hr/kg, compared to fresolimumab's 0.51 ml/hr/kg (Example 7, infra). In cynomolgus monkeys, Ab1 has been shown to have an average half-life of 13 days, compared to fresolimumab's 4.5 days, and an elimination rate (CL) of 0.40 ml/hr/kg, compared to fresolimumab's 0.66 ml/hr/kg. Id. These improved PK properties suggest that Ab1 and related antibodies may be given to patients at a lower dosage and/or less frequency than fresolimumab to achieve the same or better clinical efficacy while causing fewer adverse side effects and less anti-drug antibody reaction, thus allowing a longer duration of treatment where necessary.

Moreover, during toxicological studies of fresolimumab in nonhuman primates, a correlation between drug exposure and adverse events such as anemia was observed. However, no such event was observed in similar studies done with Ab1 at an equivalent or even higher exposure.

Without being bound by theory, we postulate that the residue 228 mutation in the heavy chain of Ab1 and related antibodies leads to the increased stability as well as improved PK and toxicological profiles.

The constant domain of Ab1 and related antibodies can be further modified as needed, for example, at Kabat residue L248 (e.g., by introducing the mutation L248E), to reduce any undesired effector function of the molecule.

As used herein, the term "antibody" (Ab) or "immunoglobulin" (Ig) refers to a tetrameric protein comprising two heavy (H) chains (about 50-70 kDa) and two light (L) chains (about 25 kDa) inter-connected by disulfide bonds. Each heavy chain is comprised of a heavy chain variable domain ($V_H$) and a heavy chain constant region ($C_H$). Each light chain is composed of a light chain variable domain ($V_L$) and a light chain constant region ($C_L$). The $V_H$ and $V_L$ domains can be subdivided further into regions of hypervariability, called "complementarity determining regions" (CDRs), interspersed with regions that are more conserved, called "framework regions" (FRs). Each $V_H$ or $V_L$ is composed of three CDRs and four FRs, arranged from amino-terminus to carboxyl-terminus in the following order: FR1, CDR1, FR2, CDR2, FR3, CDR3, and FR4. The assignment of amino acids to each region may be in accordance with IMGT® definitions (Lefranc et al., Dev Comp Immunol 27(1):55-77 (2003); or the definitions of Kabat, Sequences of Proteins of Immunological Interest (National Institutes of Health, Bethesda, M D (1987 and 1991)); Chothia & Lesk, J. Mol. Biol. 196:901-917 (1987); or Chothia et al., Nature 342: 878-883 (1989).

The term "human antibody" refers to an antibody in which the variable domain and constant region sequences are derived from human sequences. The term encompasses antibodies with sequences derived from human genes, but those sequences have been modified, e.g., to decrease immunogenicity, increase affinity, and increase stability. The term encompasses antibodies produced recombinantly in nonhuman cells, which may impart glycosylation not typical of human cells.

The term "chimeric antibody" refers to an antibody that comprises sequences from two different animal species. For example, a chimeric antibody may contain $V_H$ and $V_L$ of a murine antibody (i.e., an antibody encoded by murine antibody genes such as an antibody obtained from an immunized mouse using the hybridoma technology) linked to the constant regions of an antibody from another species (e.g., human, rabbit, or rat).

The term "antigen-binding fragment" of an antibody refers to a fragment of an antibody that retains the ability to specifically bind to an antigen. In some embodiments, an antigen-binding fragment of the present invention is an F(ab')$_2$ fragment, which is a bivalent fragment comprising two Fab fragments linked by a disulfide bridge at the hinge region (Fab is a monovalent antibody fragment consisting of the $V_L$, $V_H$, $C_L$ and $C_{H1}$ domains). In some embodiments, an antigen-binding fragment of the present invention may also comprise a $C_{H2}$ or $C_{H3}$ domain.

The antibodies and antigen-binding fragments described herein may be isolated. The term "isolated protein", "isolated polypeptide" or "isolated antibody" refers to a protein, polypeptide or antibody that by virtue of its origin or source of derivation (1) is not associated with naturally associated components that accompany it in its native state, (2) is substantially free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

I. Use of Ab1 and Related Antibodies

The TGF-β receptor is widely expressed on immune cells, leading to broad effects of TGF-β in both the innate and adaptive immune system. TGF-β has been linked to many diseased conditions, for example, birth defects, cancer, chronic inflammation, autoimmunity, and fibrotic diseases. A therapeutic amount of Ab1 or a related antibody may be used to treat these conditions. A "therapeutically effective" amount refers to the amount of Ab1, a related antibody, or another therapeutic agent referred to herein, that relieves one or more symptoms of the treated condition. This amount may vary based on the condition or patient being treated, and can be determined by a healthcare professional using well established principles.

In some embodiments, the Ab1 or related antibody may be administered at 40, 20, or 15 mg/kg or less (such as 14, 13, 12, 11, 10, 9, 8, 7, 6, 5, 4, 3, 2, or 1 mg/kg). In some further embodiments, the doses may be 0.01, 0.02, 0.03, 0.04, 0.05, 0.1, 0.2, 0.3, 0.4, or 0.5 mg/kg. The dosing frequency may be, for example, daily, every two, three, four, or five days, weekly, biweekly, or triweekly, monthly, or bimonthly. The antibody may be administered intravenously (e.g., intravenous infusion over 0.5-8 hours), subcutaneously, topically, or any other route of administration that is appropriate for the condition and the drug formulation.

Ab1 and related antibodies are derived from human antibody genes and thus have low immunogenicity in humans. Toxicology studies of Ab1 are detailed in Example 8 below. Certain cardiac and pulmonary side effects were observed in rats. Thus, patients may be monitored for adverse events when treating patients with Ab1 or a related antibody.

In some embodiments, efficacy of the antibodies of the invention can be indicated by one or more of the following in the patient (e.g., in an affected tissue such as tumor tissue in the patient): (1) a decrease in the level or activity of TGF-β, (2) an increase in MIP2 and/or KC/GRO levels, (3) activation or infiltration to the tumor tissue of $CD8^+$ T cells such as INF-γ-positive $CD8^+$ T cells, and (4) an increase in clustering of natural killer (NK) cells.

A. Non-Oncological Diseased Conditions

Conditions that can be treated by Ab1 and related antibodies may include, without limitation, bone defects (e.g., osteogenesis imperfecta), glomerulonephritis, neural or dermal scarring, lung or pulmonary fibrosis (e.g., idiopathic pulmonary fibrosis), radiation-induced fibrosis, hepatic fibrosis, myelofibrosis, scleroderma, immune-mediated diseases (including rheumatoid arthritis, multiple sclerosis, systemic lupus erythematosus, Sjogren's syndrome, Berger's disease, and transplant rejection), and Dupuytren's contracture.

They may also be useful for treating, preventing and reducing the risk of occurrence of renal insufficiencies, including but not limited to, focal segmental glomerulosclerosis (FSGS), diabetic (type I and type II) nephropathy, radiational nephropathy, obstructive nephropathy, diffuse systemic sclerosis, hereditary renal disease (e.g., polycystic kidney disease, medullary sponge kidney, horseshoe kidney), glomerulonephritis, nephrosclerosis, nephrocalcinosis, systemic or glomerular hypertension, tubulointerstitial nephropathy, renal tubular acidosis, renal tuberculosis, and renal infarction. In particular, they are useful when combined with antagonists of the renin-angiotensin-aldosterone system including but not limited to: renin inhibitors, angiotensin-converting enzyme (ACE) inhibitors, Ang II receptor antagonists (also known as "Ang II receptor blockers"), and aldosterone antagonists. See, e.g., WO 2004/098637, whose disclosure is incorporated by reference herein in its entirety.

Ab1 and related antibodies are useful to treat diseases and conditions associated with the deposition of ECM, such as systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid hemorrhage, fibrosis after laminectomy, fibrosis after tendon and other repairs, biliary cirrhosis (including sclerosing cholangitis), pericarditis, pleurisy, tracheostomy, penetrating CNS injury, eosinophilic myalgic syndrome, vascular restenosis, veno-occlusive disease, pancreatitis and psoriatic arthropathy.

Ab1 and related antibodies further are useful in conditions where promotion of re-epithelialization is beneficial. Such conditions include but are not limited to diseases of the skin, such as venous ulcers, ischemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, esophageal ulcers (reflex disease), gastro-esophageal reflux disease, stomach ulcers, small intestinal and large intestinal lesions (inflammatory bowel disease).

Still further uses of Ab1 and related antibodies are in conditions in which endothelial cell proliferation is desirable, for example, in stabilizing atherosclerotic plaques, promoting healing of vascular anastomoses, or in conditions in which inhibition of smooth muscle cell proliferation is desirable, such as in arterial disease, restenosis and asthma.

Ab1 and related antibodies also are useful to enhance the immune response to macrophage-mediated infections such as those caused by *Leishmania* spp., *Trypanosoma cruzi, Mycobacterium tuberculosis* and *Mycobacterium leprae*, as well as the protozoan *Toxoplasma gondii*, the fungi *Histoplasma capsulatum, Candida albicans, Candida parapsilosis,* and *Cryptococcus neoformans*. They are also useful to reduce immunosuppression caused, for example, by tumors, AIDS or granulomatous diseases.

Ab1 and related antibodies also are useful for the prevention and/or treatment of ophthalmological conditions such as glaucoma and scarring after trabeculectomy.

B. Oncological Diseased Conditions

TGF-β regulates several biological processes, including cell proliferation, epithelial-mesenchymal transition (EMT), matrix remodeling, angiogenesis, and immune functions. Each of these processes contributes to tumor progression. The widespread detrimental role of TGF-β in cancer patients across indications also is suggested by its elevation within the tumor microenvironment as well as systemically. See, e.g., Kadam et al., Mol. Biomark. Diagn. (2013) 4(3). Studies have shown that in the malignant state, TGF-β can induce EMT and the resulting mesenchymal phenotype leads to increased cellular migration and invasion.

Ab1 and related antibodies are useful in the treatment of hyperproliferative diseases, such as cancers including but not limited to skin cancer (e.g., melanoma, including unresectable or metastatic melanoma, cutaneous squamous cell carcinoma, and keratoacanthoma), lung cancer (e.g., non-small cell lung cancer), esophageal cancer, stomach cancer, colorectal cancer, pancreatic cancer, liver cancer (e.g., hepatocellular carcinoma), primary peritoneal cancer, bladder cancer, renal cancer or kidney cancer (e.g., renal cell carcinoma), urothelial carcinoma, breast cancer, ovarian cancer, fallopian cancer, cervical cancer, uterine cancer, prostate cancer, testicular cancer, head and neck cancer (e.g., head and neck squamous cell carcinoma), brain cancer, glioblastoma, glioma, mesothelioma, leukemia, and lymphoma.

In some embodiments, Ab1 and related antibodies are useful in treating cancers in patients for whom a prior therapy based on an anti-PD-1, anti-PD-L1 or anti-PD-L2 therapeutic agent has failed or is expected to fail, i.e., patients who are or expected to be non-responders to an anti-PD-1, anti-PD-L1, or anti-PD-L2 therapy. In some embodiments, Ab1 and related antibodies are useful in the treatment of cancers in patients who have relapsed from a prior anti-PD-1, anti-PD-L1, or anti-PD-L2 therapy. As used herein, the term "expected" means that a skilled person in the medical art may anticipate, without administering a therapy, whether a patient will be a responder or a non-responder and whether the therapy will fail or will not be effective, based on his/her general medical knowledge and the specific conditions of the patient.

In some embodiments, the cancers are mesenchymal subtypes of solid tumors, including, without limitation, mesenchymal colorectal cancer, mesenchymal ovarian cancer, mesenchymal lung cancer, mesenchymal head cancer and mesenchymal neck cancer. Epithelial mesenchymal transition (EMT) promotes cellular migration and invasive properties by down regulating epithelium cell gene and enhancing mesenchymal gene expression. EMT is a hall mark of tumor progression and invasion. Up to a quarter of colorectal and ovarian cancers are mesenchymal. Thus, by inhibiting TGF-$\beta$ and its induction of EMT, Ab1 or a related antibody can be used to treat mesenchymal solid tumors. Mesenchymal subtypes of solid tumors can be identified by a number of genetic markers and pathological tests. Markers include ACTA2, VIM, MGP, ZEB2, and ZWINT, which can be detected by qRT-PCR or immunohistochemistry. Such markers may be used to select patients for anti-TGF-$\beta$ monotherapy or combination therapy of the invention.

In some embodiments, Ab1 and related antibodies are useful in treating patients with advanced solid tumors.

Ab1 and related antibodies can also be used in the treatment of hematopoietic disorders or malignancies such as multiple myeloma, myelodysplastic syndrome (MDS), Hodgkin lymphoma, non-Hodgkin lymphoma, and leukemia, as well as various sarcomas such as Kaposi's Sarcoma.

Ab1 and related antibodies can also be useful to inhibit cyclosporine-mediated malignancy or cancer progression (e.g., metastases).

It will of course be appreciated that in the context of cancer therapy, "treatment" includes any medical intervention resulting in the slowing of cancer growth, delay in cancer progression or recurrence, or reduction in cancer metastases, as well as partial remission of the cancer in order to prolong life expectancy of a patient.

C. Combination Therapy in Oncology

It has been observed that the level of cytotoxic T cell infiltration in cancer correlates with a favorable clinical outcome (Fridman et al., Nat Rev Cancer (2012) 12(4):298-306; and Galon et al., Immunity (2013) 39(1):11-26). In addition, T helper cells that assist cytotoxic T cells (CD4$^+$ T$_{H1}$) and the cytokines they produce (e.g., IFN-$\gamma$) often correlate with positive patient outcomes as well. In contrast, the presence of Treg cells has been shown to correlate with a poor patient prognosis (Fridman, supra).

TGF-$\beta$ suppresses almost all aspects of the anti-tumor immune response. The cytokine promotes iTreg differentiation and reduces cytotoxic (CD8$^+$) cell proliferation and infiltration. Inhibition of TGF-$\beta$ by Ab1 or a related antibody will alleviate the immunosuppressive tumor microenvironment, as described above, to bring positive outcomes to cancer patients.

Further, the inventors have discovered that by alleviating the immunosuppressive tumor microenvironment, Ab1 and related antibodies can allow checkpoint modulators, such as anti-PD-1 antibody, to better induce immune responses. As a result, more patients can benefit from immunotherapy such as anti-PD-1, anti-PD-L1, or anti-PD-L2 treatment.

With or without therapeutic agents targeting the immune checkpoint molecules, Ab1 and related antibodies can also be used in conjunction with other cancer therapies such as chemotherapy (e.g., platinum- or taxoid-based therapy), radiation therapy, and therapies that target cancer antigens or oncogenic drivers.

Cancers that can be treated by a combination involving Ab1 or a related antibody and an immune checkpoint inhibitor such as an anti-PD-1 antibody include the cancers listed in the above subsection.

In some embodiments, the cancers are refractory to a prior anti-PD-1, anti-PD-L1, or anti-PD-L2 therapy, such as advanced or metastatic melanoma, non-small cell lung cancer, renal cell carcinoma, head and neck squamous cell carcinoma, and Hodgkin Lymphoma. Refractory patients are patients whose disease progresses as confirmed, e.g., radiologically within 12 weeks of commencing treatment without any evidence of a response.

In some embodiments, Ab1 or a related antibody can be used in conjunction with another cancer therapy such as anti-PD-1 therapy to treat mesenchymal cancers such as colorectal cancer, non-small cell lung cancer, ovarian cancer, bladder cancer, head and neck squamous cell carcinoma, renal cell carcinoma, hepatocellular carcinoma, and cutaneous squamous cell carcinoma. See also discussions above.

Examples of anti-PD-1 antibodies are nivolumab, pembrolizumab, pidilizumab, MEDI0608 (formerly AMP-514; see, e.g., WO 2012/145493 and U.S. Pat. No. 9,205,148), PDR001 (see, e.g., WO 2015/112900), PF-06801591 (see, e.g., WO 2016/092419) and BGB-A317 (see, e.g., WO 2015/035606). In some embodiments, the anti-PD-1 antibodies include those disclosed in WO 2015/112800 (such as those referred to as H1M7789N, H1M7799N, H1M7800N, H2M7780N, H2M7788N, H2M7790N, H2M7791N, H2M7794N, H2M7795N, H2M7796N, H2M7798N, H4H9019P, H4xH9034P2, H4xH9035P2, H4xH9037P2, H4xH9045P2, H4xH9048P2, H4H9057P2, H4H9068P2, H4xH9119P2, H4xH9120P2, H4xH9128P2, H4xH9135P2, H4xH9145P2, H4xH8992P, H4xH8999P and H4xH9008P in Table 1 of the PCT publication, and those referred to as H4H7798N, H4H7795N2, H4H9008P and H4H9048P2 in Table 3 of the PCT publication). The disclosure of WO 2015/112800 is incorporated by reference herein in its entirety.

For example, the antibodies disclosed in WO 2015/112800 and related antibodies, including antibodies and antigen-binding fragments having the CDRs, V$_H$ and V$_L$ sequences, or heavy and light chain sequences disclosed in that PCT publication, as well as antibodies and antigen-binding fragments binding to the same PD-1 epitope as the antibodies disclosed in that PCT publication, can be used in conjunction with Ab1 or a related antibody of the present invention to treat cancer. In related embodiments, a useful anti-PD-1 antibody may comprise the heavy and light chain amino acid sequences shown below as SEQ ID NOs:5 and 6, respectively; the V$_H$ and V$_L$ sequences in SEQ ID NOs:5 and 6 (shown in italics); or one or more (e.g., all six) CDRs in SEQ ID NOs:5 and 6 (shown in boxes).

(SEQ ID NO: 5)

*EVQLLESGGV LVQPGGSLRL SCAAS* GFTFS NFG *MTWVRQA PGKGLEWVSG* ISGGGRDT *YF*

*ADSVKGRFTI SRDNSKNTLY LQMNSLKGED TAVYYC* VKWG NIYFDY *WGQG TLVTVSS*AST

KGPSVFPLAP CSRSTSESTA ALGCLVKDYF PEPVTVSWNS GALTSGVHTF PAVLQSSGLY

SLSSVVTVPS SSLGTKTYTC NVDHKPSNTK VDKRVESKYG PPCPPCPAPE FLGGPSVFLF

PPKPKDTLMI SRTPEVTCVV VDVSQEDPEV QFNWYVDGVE VHNAKTKPRE EQFNSTYRVV

SVLTVLHQDW LNGKEYKCKV SNKGLPSSIE KTISKAKGQP REPQVYTLPP SQEEMTKNQV

SLTCLVKGFY PSDIAVEWES NGQPENNYKT TPPVLDSDGS FFLYSRLTVD KSRWQEGNVF

SCSVMHEALH NHYTQKSLSL SLGK (SEQ ID NO: 6)

*DIQMTQSPSS LSASVGDSIT ITCRASL* LSIN TF *LNWYQQKP GKAPNLLIY* A AS *SLHGGVPS*

*RFSGSGSGTD FTLTIRTLQP EDFATYYC* QQ SSNTPFT *FGP GTVVDFRR*TV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC

In some embodiments, the antibodies of the present invention, such as the anti-PD-1 antibodies, do not have the C-terminal lysine in the heavy chain. The C-terminal lysine may be removed during manufacture or by recombinant technology (i.e., the coding sequence of the heavy chain does not include a codon for the C-terminal terminal lysine). Thus contemplated within the invention also are antibodies comprising the heavy chain amino acid sequence of SEQ ID NO: 5 without the C-terminal lysine.

In some embodiments, an anti-TGF-β antibody or fragment of the present invention can also be used in conjunction with an antibody against an immunomodulatory antigen, such as PD-L1 and CTLA-4. Exemplary anti-PD-L1 antibodies are atezolizumab, avelumab, durvalumab, LY3300054 and BMS-936559. Exemplary anti-CTLA-4 antibodies are ipilimumab or tremelimumab.

D. Biomarkers of Treatment Efficacy

Efficacy of Ab1 and related antibodies can be determined by biomarkers or target occupancy. For example, in tumor tissues, target occupancy can be assayed by evaluating levels of active TGF-β in biopsies using a Meso Scale Discovery (MSD) assay. In the blood, target engagement can be assayed by evaluating the effect of decreased circulating TGF-β on peripheral blood mononuclear cells such as lymphocytes (T cells, B cells, NK cells) and monocytes. For example, increased proliferation of circulating CD8$^+$ T cells can be evaluated using CD45$^+$RO$^+$CCR7$^+$CD28$^+$Ki67$^+$ as markers in flow cytometry. Activation of circulating NK cells can be evaluated using CD3$^-$CD56$^{high/dim}$ CD16$^+$ or CD137$^+$ as markers in flow cytometry. Additionally, Ki-67, PD-1, and ICOS can be used as PD markers associated with T cell activation.

Immune modulation upon treatment by Ab1 or a related antibody can be assayed by evaluating changes of infiltrating immune cells and immune markers by multiplex immunohistochemistry (IHC) assays using, e.g., the NeoGenomics platform. Specifically, NeoGenomic's MultiOmyx TIL Panel stains for a panel of immune markers, allowing for quantitative determination of density and localization of various immune cells. The immune markers may indicate differentiation of iTreg; infiltration and proliferation of CD8$^+$ T cells; and generation of IFN γ by CD8$^+$ T cells. Ab1 has been shown to inhibit CD4$^+$ T cells' differentiation into iTreg (see, e.g., Example 3, infra), and to increase CD8$^+$ T cell proliferation and their generation of IFN γ (as shown in a mixed lymphocyte reaction assay; data not shown). Thus, efficacy of treatment by Ab1 or a related antibody can be indicated by inhibition of iTreg, induction of CD8$^+$ T cell proliferation and infiltration to tumor or other diseased tissues, increased IFN γ production, and/or an increased ratio of CD8$^+$ T cells to Treg cells. Immune modulation upon treatment by Ab1 or a related antibody also can be assayed in peripheral blood by methylation-PCR based quantitative immune cell counting of CD8$^+$ T cells, Treg cells, NK cells, and other immune cells. The treatment efficacy may manifest clinically as a delay or reversal in disease progression such as tumor progression.

II. Methods of Making Antibodies

The Ab1 and related antibodies, as well as antibodies targeting other co-targets such as PD-1, PD-L1 or PD-L2, can be made by methods well established in the art. DNA sequences encoding the heavy and light chains of the antibodies can be inserted into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

In addition to the antibody chain genes, the recombinant expression vectors may carry regulatory sequences that control the expression of the antibody chain genes in a host cell. Examples of regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters.

In addition to the antibody chain genes and regulatory sequences, the recombinant expression vectors of the invention may carry additional sequences, such as sequences that regulate replication of the vector in host cells (e.g., origins of replication) and selectable marker genes. For example, the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification), the neo gene (for G418 selection), and the glutamate synthetase gene.

The expression vectors encoding the antibodies of the present invention are introduced to host cells for expression. The host cells are cultured under conditions suitable for expression of the antibody, which is then harvested and isolated. Host cells include mammalian, plant, bacterial or yeast host cell. Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines may be selected based on their expression levels. Other cell lines that may be used are insect cell lines, such as Sf9 or Sf21 cells.

Further, expression of antibodies can be enhanced using a number of known techniques. For example, the glutamine synthetase gene expression system (the GS system) is a common approach for enhancing expression under certain conditions.

Tissue culture media for the host cells may include, or be free of, animal-derived components (ADC), such as bovine serum albumin. In some embodiments, ADC-free culture media is preferred for human safety. Tissue culture can be performed using the fed-batch method, a continuous perfusion method, or any other method appropriate for the host cells and the desired yield.

III. Pharmaceutical Compositions

The antibody of the invention can be formulated for suitable storage stability. For example, the antibody can be lyophilized or stored or reconstituted for use using pharmaceutically acceptable excipients. For a combination therapy, the two or more therapeutic agents such as antibodies can be co-formulated, e.g., mixed and provided in a single composition.

The term "excipient" or "carrier" is used herein to describe any ingredient other than the compound(s) of the invention. The choice of excipient(s) will to a large extent depend on factors such as the particular mode of administration, the effect of the excipient on solubility and stability, and the nature of the dosage form. "Pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some cases, isotonic agents, for example, sugars, polyalcohols such as mannitol, sorbitol, or sodium chloride will be included in the composition. Additional examples of pharmaceutically acceptable substances are wetting agents or minor amounts of auxiliary substances such as wetting or emulsifying agents, preservatives or buffers, which enhance the shelf life or effectiveness of the antibody.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Preferred embodiments may include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition. Parenteral formulations also include aqueous solutions which may contain excipients such as salts, carbohydrates and buffering agents (e.g., with a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted-, and programmed-release.

IV. Exemplary Embodiments

Further particular embodiments of the present invention are described as follows.

1. An isolated monoclonal antibody that binds specifically to human TGF-β1, TGF-β2, and TGF-β3, comprising the heavy chain complementarity-determining regions (CDR) 1-3 in SEQ ID NO:1 and the light chain CDR1-3 in SEQ ID NO:2, wherein the antibody comprises a human IgG$_4$ constant region having a proline at position 228 (EU numbering).

2. The antibody of embodiment 1, wherein the antibody comprises a heavy chain variable domain (V$_H$) amino acid sequence corresponding to residues 1-120 of SEQ ID NO:1 and a light chain variable domain (V$_L$) amino acid sequence corresponding to residues 1-108 of SEQ ID NO:2.

3. The antibody of embodiment 2, wherein the antibody comprises a heavy chain amino acid sequence set forth in SEQ ID NO:1 (with or without the C-terminal lysine) and a light chain amino acid sequence set forth in SEQ ID NO:2.

4. An antigen-binding fragment of the antibody of embodiment 3, wherein the fragment is an F(ab')$_2$.

5. The antibody or fragment of any one of embodiments 1-4, wherein the antibody or fragment has an increased half-life or increased exposure as compared to fresolimumab.

6. The antibody or fragment of any one of embodiments 1-5, wherein the antibody or fragment has one or more of the following properties:
   a) inhibits the differentiation of CD4$^+$ T cells into inducible regulatory T cells (iTreg);
   b) increases CD8$^+$ T cell proliferation;
   c) increases clustering of natural killer (NK) cells;
   d) increases the level of MIP-2; and
   e) increases the level of KC/GRO.

7. A composition comprising the antibody or fragment of any one of embodiments 1-6, wherein the composition comprises less than 1% of half antibody.

8. The antibody or fragment of any one of embodiments 1-6 as a medicament.

9. A method of inhibiting TGF-β signal transduction in a patient in need thereof, comprising administering to the patient a therapeutic amount of the antibody or fragment of any one of embodiments 1-6.

10. The method of embodiment 9, wherein the patient has cancer.

11. The method of embodiment 10, wherein the cancer is selected from the group consisting of melanoma, lung cancer, cutaneous squamous cell carcinoma, colorectal cancer, breast cancer, ovarian cancer, head and neck cancer, hepatocellular carcinoma, urothelial cancer, and renal cell carcinoma.

12. The method of embodiment 10 or 11, wherein the cancer is characterized by overexpression of one or more of ACTA2, VIM, MGP, and ZWINT.

13. The method of any one of embodiments 10-12, wherein the cancer is a mesenchymal tumor.

14. The method of any one of embodiments 10-13, wherein the antibody or fragment alleviates the immunosuppressive tumor microenvironment.

15. A method of treating cancer in a patient, comprising administering to the patient (1) the antibody or fragment of any one of embodiments 1-6, and (2) an inhibitor of an immune checkpoint protein.

16. The method of embodiment 15, wherein the immune checkpoint protein is PD-1, PD-L1, or PD-L2.

17. The method of embodiment 16, wherein the inhibitor of the immune checkpoint protein is an anti-PD-1 antibody.

18. The method of embodiment 17, wherein the anti-PD-1 antibody comprises the heavy chain CDR1-3 in SEQ ID NO:5 and the light chain CDR1-3 in SEQ ID NO:6.

19. The method of embodiment 17, wherein the anti-PD-1 antibody comprises a V$_H$ amino acid sequence corresponding to residues 1-117 of SEQ ID NO:5 and a V$_L$ amino acid sequence corresponding to residues 1-107 of SEQ ID NO:6.

20. The method of embodiment 17, wherein the anti-PD-1 antibody comprises a heavy chain amino acid sequence set forth in SEQ ID NO:5 (with or without the C-terminal lysine) and a light chain amino acid sequence set forth in SEQ ID NO:6.

21. The method of any one of embodiments 15-20, wherein the anti-TGF-β antibody comprises a heavy chain amino acid sequence set forth in SEQ ID NO:1 (with or without the C-terminal lysine) and a light chain amino acid sequence set forth in SEQ ID NO:2.

22. The method of any one of embodiments 15-21, wherein the cancer is refractory to anti-PD-1 antibody treatment.

23. The method of any one of embodiments 15-22, wherein the cancer is advanced or metastatic melanoma, or cutaneous squamous cell carcinoma.

24. The method of any one of embodiments 15-23, wherein the cancer is a mesenchymal subtype of a solid tumor.

25. The method of any one of embodiments 15-24, wherein the cancer is characterized by overexpression of one or more of ACTA2, VIM, MGP, and ZWINT.

26. The method of any one of embodiments 15-25, wherein the cancer is selected from the group consisting of melanoma, lung cancer, cutaneous squamous cell carcinoma, colorectal cancer, breast cancer, ovarian cancer, head and neck cancer, hepatocellular carcinoma, urothelial cancer, and renal cell carcinoma.

27. The method of any one of embodiments 15-26, wherein the antibody or fragment alleviates the immunosuppressive tumor microenvironment.

28. The method of any one of embodiments 15-27, wherein the anti-TGF-β antibody and the anti-PD-1 antibody are administered on the same day to the patient.

29. The method of any one of embodiments 15-28, wherein the anti-TGF-β antibody and the anti-PD-1 antibody are administered biweekly to the patient.

30. The method of any one of embodiments 15-29, wherein the anti-TGF-β antibody and the anti-PD-1 antibody are administered respectively at a dose of 0.05-20 mg/kg body weight.

31. A method of increasing an immune response in a patient in need thereof, comprising administering to the patient an immune checkpoint inhibitor and the antibody or fragment of any one of embodiments 1-6.

32. The method of embodiment 31, wherein the checkpoint inhibitor is an anti-PD-1 antibody.

33. The method of embodiment 32, wherein the anti-PD-1 antibody comprises:
 a) the HCDR1-3 in SEQ ID NO:5 and the LCDR1-3 in SEQ ID NO:6;
 b) a $V_H$ and a $V_L$ corresponding to residues 1-117 in SEQ ID NO:5 and residues 1-107 in SEQ ID NO:6, respectively; or
 c) a heavy chain having the amino acid sequence set forth in SEQ ID NO:5 (with or without the C-terminal lysine) and a light chain having the amino acid sequence set forth in SEQ ID NO:6.

34. The method of any one of embodiments 31-33, wherein the anti-TGF-β antibody comprises a heavy chain amino acid sequence set forth in SEQ ID NO:1 (with or without the C-terminal lysine) and a light chain amino acid sequence set forth in SEQ ID NO:2.

35. The method of any one of embodiments 31-34, wherein the patient has cancer.

36. The method of embodiment 35, wherein the patient is refractory to a prior treatment with the immune checkpoint inhibitor, and/or has a mesenchymal subtype of a solid tumor.

37. The method of embodiment 35 or 36, wherein the cancer is selected from the group consisting of melanoma, lung cancer, cutaneous squamous cell carcinoma, colorectal cancer, breast cancer, ovarian cancer, head and neck cancer, hepatocellular carcinoma, urothelial cancer, and renal cell carcinoma.

38. The method of any one of embodiments 35-37, wherein the cancer is characterized by overexpression of one or more of ACTA2, VIM, MGP, and ZWINT.

39. The method of any one of embodiments 35-38, wherein the antibody or fragment alleviates the immunosuppressive tumor microenvironment.

40. An antibody or fragment of any one of embodiments 1-6 for use in treating a patient in any of the above methods.

41. Use of an antibody or fragment of any one of embodiments 1-6 for the manufacture of a medicament for treating a patient in any of the above methods.

42. An isolated nucleic acid molecule, comprising a nucleotide sequence encoding the heavy chain, the light chain, or both, of the antibody or fragment of any one of embodiments 1-6.

43. An expression vector comprising the isolated nucleic acid molecule of embodiment 42.

44. A host cell comprising the expression vector of embodiment 43.

45. A method of producing an antibody or antigen-binding fragment of any one of embodiments 1-6, the method comprising:
 providing a host cell comprising first and second nucleotide sequences encoding the heavy chain and light chain, respectively, of the antibody or antigen-binding fragment,
 growing the host cell under conditions permitting production of the antibody or antigen-binding fragment, and
 recovering the antibody or antigen-binding fragment.

46. A method of producing a pharmaceutical composition, comprising:
 providing an antibody or antigen-binding fragment of any one of embodiments 1-6, and
 admixing the antibody or antigen-binding fragment with a pharmaceutically acceptable excipient.

47. An article of manufacture or kit comprising an antibody or antigen-binding fragment of any one of embodiments 1-6 and another therapeutic agent.

48. The article of manufacture or kit of embodiment 47, wherein the other therapeutic agent is an immune checkpoint inhibitor described herein.

The invention will be further described in the following examples, which do not limit the scope of the invention described in the claims.

EXAMPLES

In order for this invention to be better understood, the following examples are set forth. These examples are for illustration only and are not to be construed as limiting the scope of the invention in any manner.

Example 1: TGF-β-Binding Properties of Ab1

The affinity of Ab1 for all human and murine TGF-β isoforms was determined by surface plasmon resonance on a Biacore T200 Biosensor instrument (GE Healthcare) using a dextran-coated carboxy-methylated (CM5) series S chip. Ab1 at a series of concentrations (1.11, 3.33, 10, and 30 nM) was injected onto immobilized recombinant TGF-β to measure the binding interaction in real time. The TGF-β homodimers were immobilized at a low density to reduce avidity effects. Injections were performed in triplicate and the binding assay was repeated three times. The data from the kinetic experiments were processed using the Biacore T200 Biaevaluation v2.0 software. Resulting sensorgrams were zeroed, aligned, double referenced, and cropped for curve fitting analysis using a 1:1 binding model to determine association rate constant ($k_a$), dissociation rate constant ($k_d$), and equilibrium dissociation constant ($K_D$).

The recombinant proteins were either produced internally (human TGF-β1, 2 and 3) or acquired from R&D Systems (murine TGF-β1 and 2). Table 1 below shows the amino acid sequence homology of the three active TGF-β isoforms between rhesus monkeys, mice, or rats and humans (homology is reported as the percentage of conserved amino acids over total amino acids).

TABLE 1

Homology of TGF-β Active Isoforms to Humans

| | Percent Homology | | |
| --- | --- | --- | --- |
| | TGF-β1 | TGF-β2 | TGF-β3 |
| Rh. Monkey | 100% (112/112) | 100% (112/112) | 100% (112/112) |
| Mouse | 99.1% (111/112)* | 97% (109/112)* | 100% (112/112) |
| Rat | 99.1% (111/112)* | 97% (109/112)* | 99.1% (111/112) |

*Rat and mouse TGFβ1 are 100% homologous to each other, and rat and mouse TGFβ2 are 100% homologous to each other Since human TGF-β3 and murine TGF-β3 are identical in amino acid sequence, separate affinity measurements were not calculated for these two proteins. Likewise, murine and rat TGF-β1 and 2 are identical in amino acid sequence and separate affinity measurements also were not calculated.

The $k_a$, $k_d$, and $K_D$ values of Ab1 as determined by the above method are presented in Table 2 below. The $K_D$ values of Ab1 for human TGF-β1, 2, and 3 were determined to be 1.48, 3.00, and 1.65 nM, respectively. The $K_D$ values of Ab1 for murine/rat TGF-β1 and 2 were determined to be 2.80 and 1.88 nM, respectively. These binding properties are similar to those of fresolimumab.

TABLE 2

Equilibrium Constants and Affinity of Ab1 for TGF-β

| | Human | | Murine and Rat | | Human and Murine |
|---|---|---|---|---|---|
| | TGF-β1 | TGF-β2 | TGF-β1 | TGF-β2 | TGF-β3 |
| $k_a$ (×10⁵ M⁻¹s⁻¹) | 3.11 ± 0.3 | 2.86 ± 0.3 | 2.98 ± 0.07 | 3.48 ± 0.24 | 2.23 ± 0.6 |
| $k_d$ (×10⁻⁴ s⁻¹) | 3.43 ± 2.9 | 8.23 ± 5.0 | 8.35 ± 0.38 | 6.45 ± 1.44 | 3.72 ± 2.3 |
| $K_D$ (nM) | 1.48 ± 1.1 | 3.00 ± 2.0 | 2.80 ± 0.08 | 1.88 ± 0.56 | 1.65 ± 1.1 |

The above data demonstrate that Ab1 is a potent and selective pan-TGF-β inhibitor. Measurements using surface plasmon resonance demonstrate that Ab1 has affinities between 1 and 5 nM for all human and murine TGF-β isoforms. The high level of specificity was confirmed by GLP immunohistochemistry (IHC) tissue cross-reactivity studies using normal rat, cynomolgus monkey and human tissues.

Example 2: TGF-β-Neutralizing Potency of Ab1

The in vitro potency of Ab1 in neutralizing TGF-β activity was measured in a cell-based assay. This assay measured the ability of TGF-β to inhibit the proliferation of untransformed mink lung epithelial cells (Mv 1 Lu cells). See, e.g., WO 2006/086469 and Mazzieri, et al., Eds, "Methods in Molecular Biology," Vol. 142, "Transforming Growth Factor-β Protocols." The ability of Ab1, fresolimumab, and 1D11 (a murine anti-TGF-β antibody, whose heavy and light chain sequences are disclosed herein as SEQ ID NOs:9 and 10) to neutralize human TGF-β1, 2, 3 and murine TGF-β1 and 2 was assessed. The recombinant TGF-β proteins were either produced internally (human TGF-β1, 2 and 3) or acquired from R&D Systems (murine TGF-β1 and 2).

All human and murine TGF-β isoforms inhibited the proliferation of the mink lung cells in a dose-dependent manner in the range of 0.02 μg/ml to 10 ng/ml. To quantify the potency of Ab1, fresolimumab, and 1D11, 1 ng/ml of the designated TGF-β and serially-diluted antibody were incubated with the mink lung cells. Following three days of incubation, proliferation of the cells was quantified by CyQUANT dye which fluoresces upon binding to DNA (FIGS. 1A-E). The data show that Ab1, fresolimumab, and their murine surrogate 1D11 inhibited all human and murine TGF-β isoforms to a similar extent.

Example 3: Inhibition of Inducible T Regulatory Cell Differentiation by Ab1

Regulatory T cells (Treg) are immunosuppressive and have been correlated with negative outcomes in cancer patients. In the study described below, we investigated whether Ab1 could inhibit TGF-β-induced differentiation of human CD4⁺ T cells into inducible regulatory T cells (iTreg). Primary human CD4⁺ T cells were isolated from healthy normal donors. Human TGF-β1 was purchased from R&D Systems.

Figure 2:
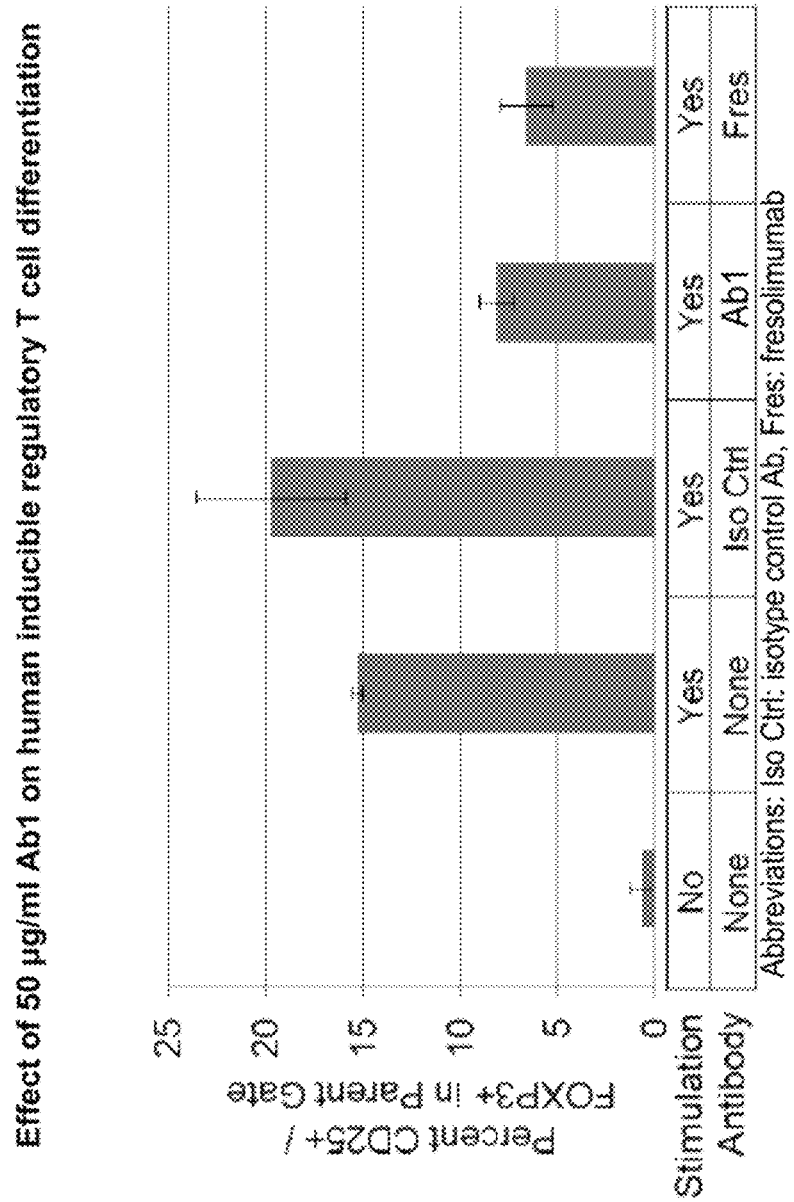
FIG. 2 is a bar graph showing the effect of 50 μg/ml Ab1 on human inducible regulatory T cell (iTreg) differentiation. Stimulation provided to the T cells was anti-CD3 and anti-CD28 antibodies plus IL-2.

To investigate the antagonist activity of Ab1 for TGF-β generated endogenously by the cultured cells, total CD4⁺ T cells without the addition of exogenous TGF-β were treated with 50 μg/ml of isotype control (human IgG4, kappa anti-hen egg lysozyme (HEL) antibody, Crown Biosience), Ab1 or fresolimumab in the presence or absence of stimulation (anti-CD3, anti-CD28, and IL-2) for 6 days followed by flow cytometric analysis. Mean percent and standard deviation of the CD25⁺FOXP3⁺ population was calculated from the parent population (lymphocytes/live/single cells/CD4⁺CD127⁻) in triplicate. Stimulation of total human CD4⁺ T cells with anti-CD3, anti-CD28, and IL-2 increased the percentage of FOXP3⁺CD25⁺ (iTreg) in the culture from 0% to 15%. Treatment with 50 μg/ml Ab1 or 50 μg/ml fresolimumab decreased the percentage of iTreg to a similar extent (8% and 7% respectively; FIG. 2). By contrast, treatment with an isotype human IgG₄ (hIgG₄) control had minimal effect on iTreg differentiation (20% iTreg) (FIG. 2). CD4⁺ T cells isolated from a second healthy normal volunteer generated similar results.

Figure 3:
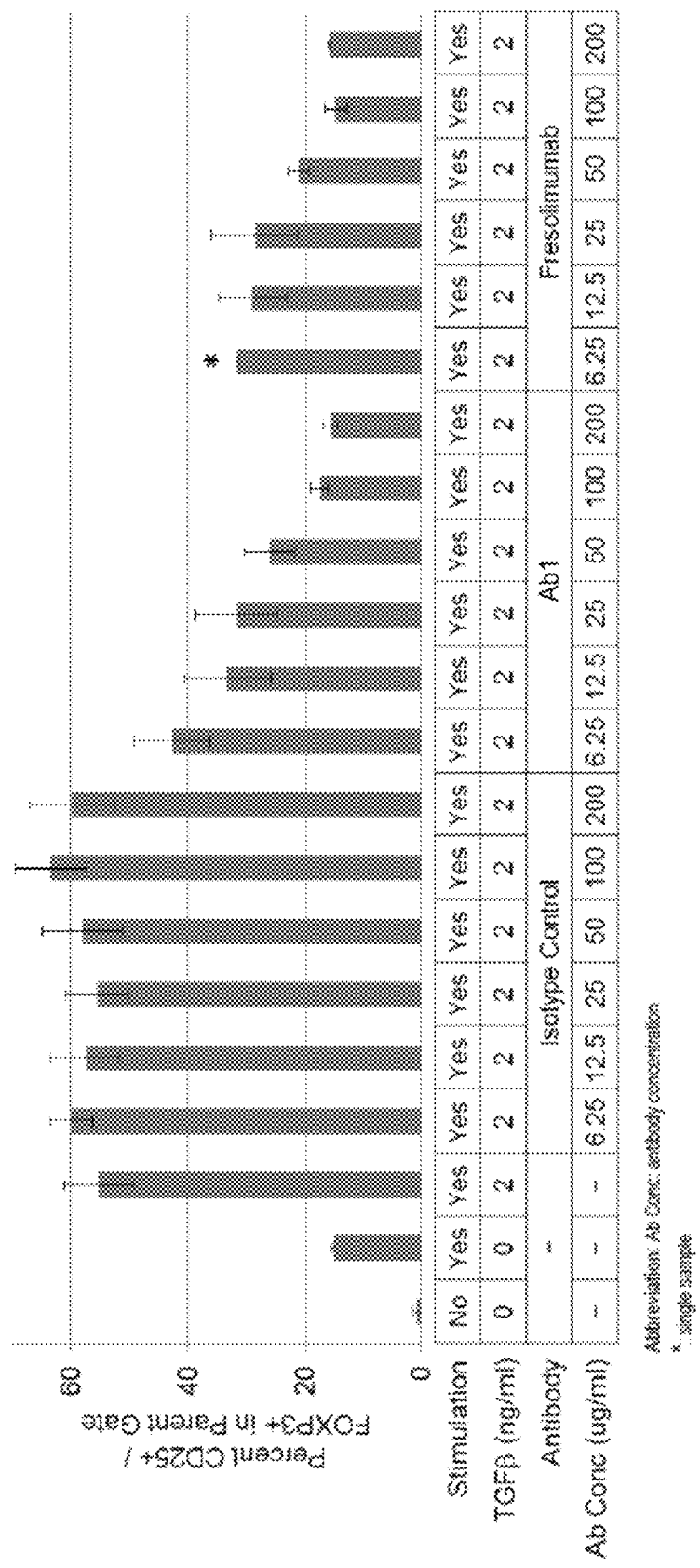
FIG. 3 is a bar graph showing the effect of Ab1 on human inducible regulatory T cell (iTreg) differentiation in human CD4+ T cell cultures treated with 2 ng/ml human TGF-β1. Stimulation provided to the T cells was anti-CD3 and anti-CD28 antibodies plus IL-2.

To investigate the antagonist activity of Ab1 for exogenous TGF-β, total CD4⁺ T cells incubated with 2 ng/ml human TGF-β1 were treated with isotype control, Ab1, or fresolimumab at various antibody concentrations in the presence or absence of stimulation (anti-CD3, anti-CD28, and IL-2) for 6 days followed by flow cytometric analysis. Mean percent and standard deviation of the CD25⁺FOXP3⁺ population was calculated from the parent population (lymphocytes/live/single cells/CD4⁺CD127⁻) in triplicate except where noted. The addition of exogenous TGF-β1 (2 ng/ml) to stimulated total human CD4⁺ T cells increased the percentage of iTreg in the culture from 15% to 55%. Treatment with increasing concentrations of Ab1 decreased the percentage of iTreg in a concomitant fashion from 55% to 15% at 200 μg/ml and 43% at 6.25 μg/ml. Treatment with fresolimumab decreased the percentage of iTreg to a similar extent as Ab1 (from 55% to 16% at 200 μg/ml and 32% at 6.25 μg/ml). Treatment with varying concentrations of the isotype control antibody had no effect on the percentage of iTreg with 60% at 200 μg/ml and 6.25 μg/ml. See FIG. 3. CD4⁺ T cells isolated from a second healthy normal volunteer generated similar results.

This study demonstrates that Ab1 inhibits iTreg differentiation induced by TGF-β and thus may bring clinical benefit by alleviating the immunosuppressive tumor microenvironment.

Example 4: Effects of Ab1 and Anti-PD-1 Antibody Combination In Vitro

In this study, we investigated whether TGF-β would prevent maximal stimulation of T cells in vitro following anti-PD-1 treatment, and if so, whether Ab1 could counteract this prevention. Luciferase expression from an expression construct under the transcriptional control of an NFATc (nuclear factor of activated T cells, cytoplasmic 1) regulatory sequences was used to measure the level of T cell activation.

We used a cell assay system purchased from Promega for this study. This system comprises two cell types: 1) Jurkat T cells expressing human PD-1 and a luciferase reporter driven by an NFAT response element, and 2) CHO-K1 cells expressing human PD-L1 and an engineered cell surface protein designed to activate cognate T cell receptor in an antigen-independent manner. Upon co-culture the Jurkat T cells interact with the CHO-K1 cells, causing T cell receptor stimulation and NFATc translocation into the nucleus where it drives luciferase expression. However, engagement of PD-1/PD-L1 recruits tyrosine-protein phosphatase non-receptor 11 (SHP2) to the T cell receptor complex, inhibiting NFATc nuclear translocation and subsequent luciferase expression. Blockade of PD-1 signaling relieves the SHP2-dependent suppression and thus allows for maximal luciferase expression. The system thus provides a functional method for determining the effect of TGF-β on T cell signaling and the impact of Ab1 on anti-PD-1 treatment of the T cells.

Due to the slow kinetics associated with TGF-β-dependent effects, the Jurkat T cells were pre-treated with TGF-β prior to T cell receptor stimulation. Human TGF-β1 was purchased from R&D Systems. Isotype control antibody for Ab1 (anti-HEL hIgG$_4$) was purchased from Crown Bioscience (Cat # C0004-5). Mouse anti-hPD-1 IgG and its isotype control antibody were purchased from BioLegend (Cat #329912). Fourteen replicates were analyzed for each sample.

Figure 4:
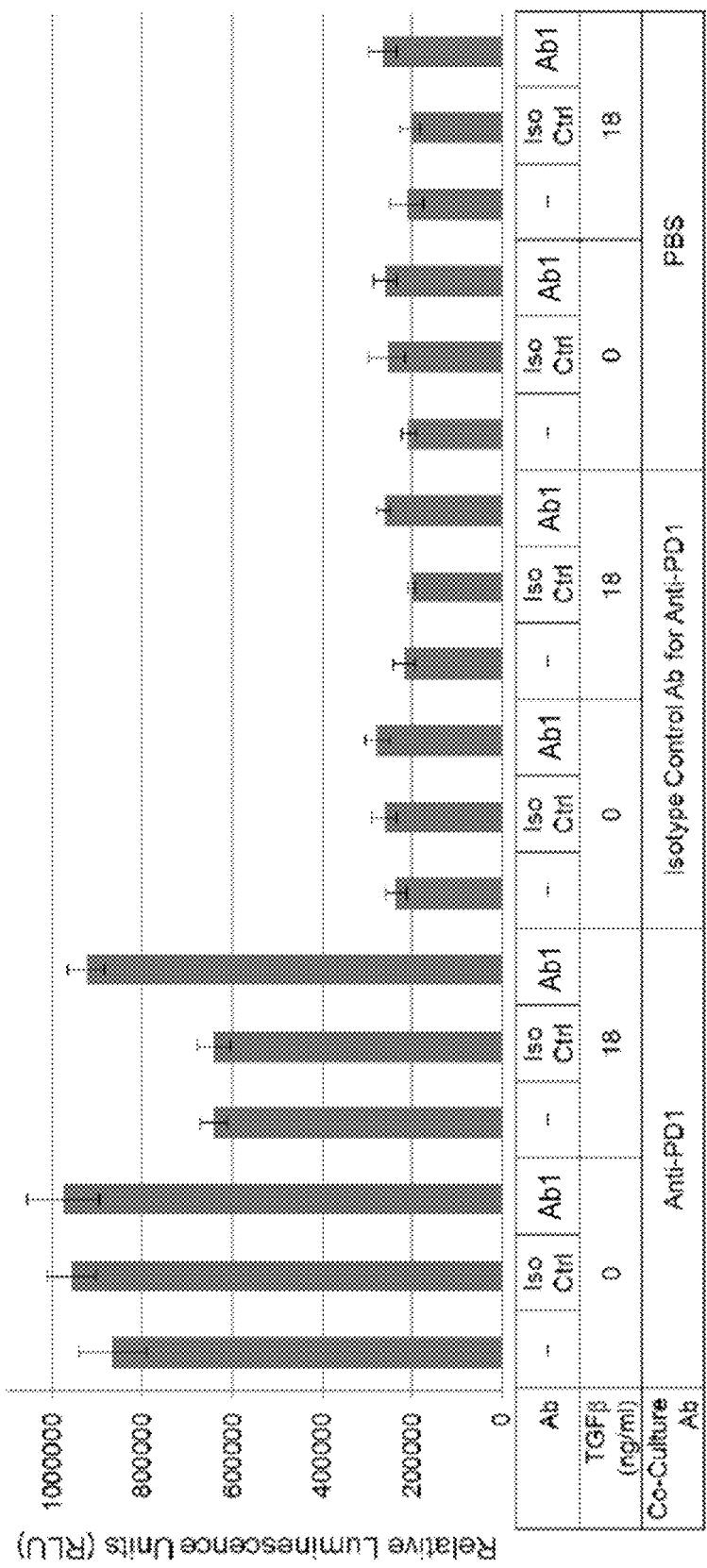
FIG. 4 is a bar graph showing the effect of Ab1 (30 μg/ml) and human TGF-β1 (18 ng/ml) on NFATc-driven luciferase expression on Jurkat T cells following T cell stimulation and anti-PD-1 treatment.

The results showed that addition of the anti-hPD-1 antibody to Jurkat T cells co-cultured with CHO-K1 cells for 24 hours induced luciferase activity (865794 relative luminescence units [RLU]) to a greater extent than the addition of the isotype control (234963 RLU, fold change=3.685, p-value<0.0001) or just the absence of antibody (206043 RLU, fold change=4.202, p-value<0.0001). Pre-treatment of Jurkat T cells with 18 ng/ml TGF-β1 for 12 days induced less luciferase activity (638866 RLU) in CHO-K1 cell co-culture in the presence of the anti-hPD-1 antibody, as compared to Jurkat T cells not treated with TGF-β1 (865794 RLU, fold change=−1.355, p-value<0.0001) (FIG. 4).

To evaluate the antagonistic potency of Ab1, Jurkat T cells were pre-treated with 18 ng/ml TGF-β1 in the presence of Ab1, isotype control Ab, or no Ab for 12 days and then co-cultured with CHO-K1 cells in the presence of anti-PD-1 for 24 hours. The presence of Ab1 (924186 RLU) relieved the TGF-β-dependent suppression of luciferase activity as compared to isotype control Ab (639440 RLU, fold change=1.445, p-value<0.0001) and no Ab control (638866 RLU, fold change=1.447, p-value<0.0001). Control groups with Ab1 (975654 RLU) or isotype control (955717 RLU) added to Jurkat T cells not pre-treated with TGF-β1 and co-cultured with CHO-K1 cell co-culture in the presence of anti-PD-1 Ab had statistically-elevated luciferase activity compared to no Ab control, but with minimal fold change (865794 RLU, fold-change=1.127 and 1.104, p-value=0.0023 and 0.001284, respectively) (FIG. 4). The RLU values are also presented in Table 3 below.

TABLE 3

Relative Luminescence Units in T Cell Activation Assay

| | Anti-PD-1 Ab | | | |
|---|---|---|---|---|
| | No TGF-β1 pre-treat | TGF-β1 pre-treat | Anti-PD-1 Ab Isotype Control | Vehicle (PBS) |
| No Ab1 | 865794 | 638866 | 234963 | 206043 |
| Ab1 | 975654 | 924186 | — | — |
| anti-HEL hIgG$_4$ | 955717 | 639440 | — | — |

To exclude the possibility that TGF-β1 pre-treatment of the Jurkat T cells might have led to decreased proliferation or viability and hence resulted in decreased luciferase activity during the 24 hour co-culture with CHO-K1 cells, we incubated Jurkat T cells with 18 ng/ml TGF-β1 or PBS in the presence of Ab1, anti-HEL hIgG$_4$, or no antibody (vehicle) for 7 days. Every 2 to 3 days an equal volume of each group was used to seed a new flask at which time both TGF-β1 and antibody were refreshed (a total of two re-seeding events occurred). Assessment of the final culture demonstrated that the viability of all treatment groups was unchanged (ranging from 94% to 96%). In addition, the total number of Jurkat T cells in the final culture of each treatment group was very similar (ranging from 25 to 29 million).

The above study demonstrate that the increase in signaling downstream of the T cell receptor following anti-PD-1 treatment is suppressed by TGF-β, leading to sub-optimal T cell stimulation. Our data suggest that the inhibition of TGF-β alleviates the immunosuppressive tumor microenvironment and allows checkpoint modulators, such as anti-PD-1 agents, to better induce immune responses and thus increase the proportion of patients benefitting from immune oncology treatment.

Example 5: Effects of Ab1 and Anti-PD1 Antibody Combination In Vivo

We next studied the effects of combined anti-TGF-β and anti-PD-1 treatment in a C57BL/6 mouse cancer model.

Tolerability/Preliminary Safety

Materials and Methods

The tolerability of Ab1 and an anti-mouse PD-1 (mPD-1) monoclonal antibody (mAb) as single agents and in combination were evaluated in C57BL/6 female mice. Ab1 (10, 20, and 50 mg/kg) or an isotype control Ab (anti-HEL hIgG$_4$ purchased from Crown Bioscience; used at 10 and 20 mg/kg) were administered IV every three days (Q3D) as single agents or in combination with the anti-PD1 Mab at 5 mg/kg IV twice weekly. The anti-PD1 Ab used in this study was, designated as "antim_PD1_hyb_RMP114_m IgG1LCfullrat" (or x-anti-m PD-1 Mab). It was a chimeric rat anti-mPD-1 antibody generated by replacing the rat Fc region of rat IgG$_{2a}$ clone RMP1-14 (BioXcell, Cat. # BE0146) with a mouse IgG$_1$ Fc region. The heavy and light amino sequences of this chimeric antibody are shown in SEQ ID NOs:7 and 8. Tolerability was assessed by measuring animal body weights and clinical observations. At the end of the three week treatment, four hours after the last treatment, terminal sampling was performed and tissues (heart, kidney, liver, lung, and spleen) were fixed in formaldehyde and sent for histopathological analyses.

A dosage was considered excessively toxic if it produced 15% body weight loss during three consecutive days in an individual mouse, 20% body weight loss during one day, or 10% or more drug-related deaths, unless tumor-induced cachexia leading to body weight loss was observed in the control vehicle-treated group. Animal body weight included the tumor weight.

Toxicity/Safety Results

The tolerability study in C57BL/6 mice showed that all tested dose levels of single agents and combinations of Ab1 and x-anti-mPD-1 Mab were well tolerated. No major changes in body weight were observed in any of the treatment groups at all doses tested. No severe or major clinical observations were observed during the study. Histopathological analyses identified increased numbers of lymphocytes in the spleen (white pulp) of all treated groups including isotype control antibody treated groups, whatever the combination and without any dose-relationship. No other significant microscopic findings were observed. Two mice from the combination group, the isotype control Ab (10 mg/kg) and the anti-PD-1 Mab (5 mg/kg), were found dead after final administration on the last day of study. Histopathological analyses did not find any drug related causes of death.

Efficacy Study

The effects of combining anti-TGF-β and anti-PD-1 treatment in C57BL/6 mice bearing subcutaneous MC38 syngeneic colon tumors were evaluated. Mice were given Ab1 at 25 mg/kg, the x-anti-mPD-1 Mab at 5 mg/kg, or both, Q3D for three weeks. This study demonstrates that Ab1 and anti-mPD-1 Mab combination had significantly greater anti-tumor activity than single agents alone. The materials and methods and the data of this study are described in detail below.

Materials and Methods

Animals

Female C57BL/6 mice were obtained from Charles River Labs (Wilmington, Mass., USA). Animals were allowed to acclimate for at least three days before the study enrollment. Mice were 11 weeks-old and weighted between 17.0 and 20.9 g at the beginning of the study. They had free access to food (Harlan 2916 rodent diet, Mass., USA) and sterile water, and were housed on 12 hours light/dark cycle.

Tumor Cells

MC38 is a colon adenocarcinoma cell line. The cells were obtained from the National Cancer Institute (Bethesda, Md., USA) and cultured in 5% $CO_2$ at 37° C. in complete medium (CM), which included Roswell Park Memorial Institute medium (RPMI)-1640 with L-glutamine (Gibco, Cat #11875), supplemented with 10% heat-inactivated fetal bovine serum (HI FBS) (Gibco, Cat #10438026). The cells were harvested and re-suspended in Dulbecco's phosphate-buffered saline (DPBS) (Gibco, Cat #14190), and $1 \times 10^6$ cells/200 µl per mouse were subcutaneously (SC) implanted into the right flank of female C57BL/6 mice.

Compounds

Ab1 was administered to the animals in an aqueous solution. It was 0.22 µm-filtered through PES and stored in sterile aliquots at 2 to 10° C. The antibody was given to the animals at 10 ml/kg intraperitoneally (IP), 25 mg/kg.

Anti-HEL hIgG$_4$ (Crown Bioscience) was used as an isotype control for Ab1. This antibody was given to control animals by IP at 10 ml/kg by IP, 25 mg/kg.

The x-anti-mPD-1 Mab (supra) was provided in DPBS (Gibco, Cat #14190-094) and was given to the animals by IP at 10 ml/kg, 5 mg/kg.

Study Design

On day 0, 60 animals were implanted with MC38 tumor cells. On day 8 post implantation, the mice, which had an average tumor size of 50-75 mm³, were pooled and randomly distributed to control and treatment groups (ten mice per group). Treatments with vehicle (PBS, pH 7.2), anti-HEL hIgG$_4$, Ab1, and the anti-mPD-1 Mab at the doses described above were initiated on day 9 and were repeated on days 12, 15, 18, 21, and 27. Vehicle- and anti-HEL hIgG$_4$-treated animals were used as controls. The mice were checked daily and adverse clinical reactions noted. Individual mice were weighed three to four times a week until the end of the experiment.

Mice were euthanized when morbidity or weight loss ≥20% was observed. Tumors were measured with a caliper twice weekly until final sacrifice. When a tumor size reached approximately 2000 mm³ or there were animal health issues (20% area of a tumor ulcerated), the animals would be euthanized and date of death recorded. Solid tumor volumes were estimated from two dimensional tumor measurements and calculated according to the following equation:

$$\text{Tumor volume (mm}^3\text{)} = [\text{length (mm)} \times \text{width}^2 \text{ (mm}^2\text{)}]/2$$

The percent median regression for a group at a given day was then obtained by taking the median of the individual percent regression calculated for each animal of the group at this day. The day of calculation was determined on the day when $\Delta T/\Delta C$ (i.e., the ratio of medians of tumor volume changes from baseline between the treated and control groups) was calculated, except when median percent regression was not representative of the activity of the group. In that case, the day was determined on the first day when the median percent regression was maximal. Regressions were defined as partial (PR) if the tumor volume decreased to 50% of the tumor volume at the start of treatment. Complete regression (CR) was considered to have been achieved when tumor volume was below 14 mm³ or could not be recorded.

Efficacy

The primary efficacy end points were tumor volume changes from baseline as indicated by $\Delta T/\Delta C$, median percent regression, partial regression, and complete regression. Changes in tumor volume for each treated (T) and control (C) group were calculated for each animal every day by subtracting the tumor volume on the day of first treatment (staging day) from the tumor volume on the specified observation day. The median $\Delta T$ was calculated for the treated group and the median $\Delta C$ was calculated for the control group. The ratio $\Delta T/\Delta C$ is calculated and expressed as percentage:

$$\Delta T/\Delta C = (\text{median delta}T/\text{median delta}C) \times 100$$

A $\Delta T/\Delta C$ ratio 40% was considered therapeutically active. A $\Delta T/\Delta C$ ratio of 0% was considered as tumor stasis. A $\Delta T/\Delta C$ ratio <0% was considered as tumor regression.

Percent tumor regression was defined as percentage of tumor volume decrease in the treated group on a specified observation day compared to the tumor volume at the beginning of the study ($t_0$). At a specific time point (t) and for each animal, percent regression was calculated using the following formula:

$$\% \text{ regression (at } t) = [(\text{volume}_{t_0} - \text{volume}_t)/\text{volume}_{t_0}] \times 100$$

The median percent regression for a group on a given day was then calculated by taking the median of individual % regression values calculated for each animal in the group. The day of calculation was determined by the day when $\Delta T/\Delta C$ was calculated, except when the median percent regression was not representative of the activity of the group. In that case, the day was determined by the first day when the median percent regression was maximal.

Statistical Analysis

A two-way ANOVA type with factors treatment and day (repeated) was performed on tumor volume changes from baseline. In case of significant treatment*day interaction or treatment effects, it was followed by a contrast analysis with Bonferroni-Holm correction for multiplicity to compare all treated groups to the control group at each day from day 8 to 27. Tumor volume changes from baseline were calculated for each animal and each day by subtracting the tumor volume on the day of first treatment (day 8) from the tumor volume on the specified observation day.

Figure 5:
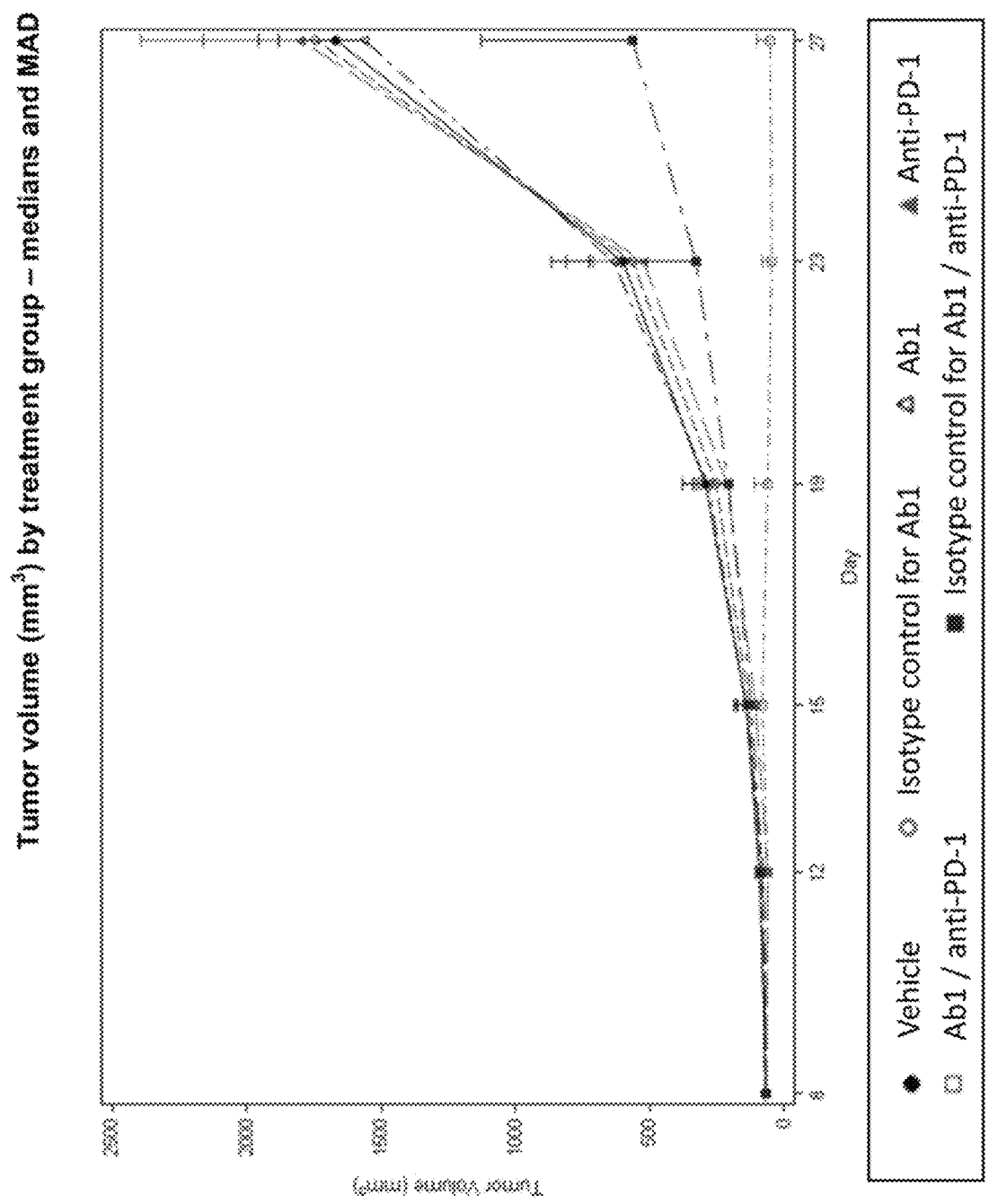
FIG. 5 is a graph showing the median tumor volumes with the median absolute deviation (MAD) in the indicated treatment groups using the C57BL/6 MC38 colon mouse model. Vehicle: PBS. "Anti-PD-1": x-anti-mPD-1 Mab (see Detailed Description below). "Isotype control of Ab1": anti-HEL hIgG4.
Figure 6:
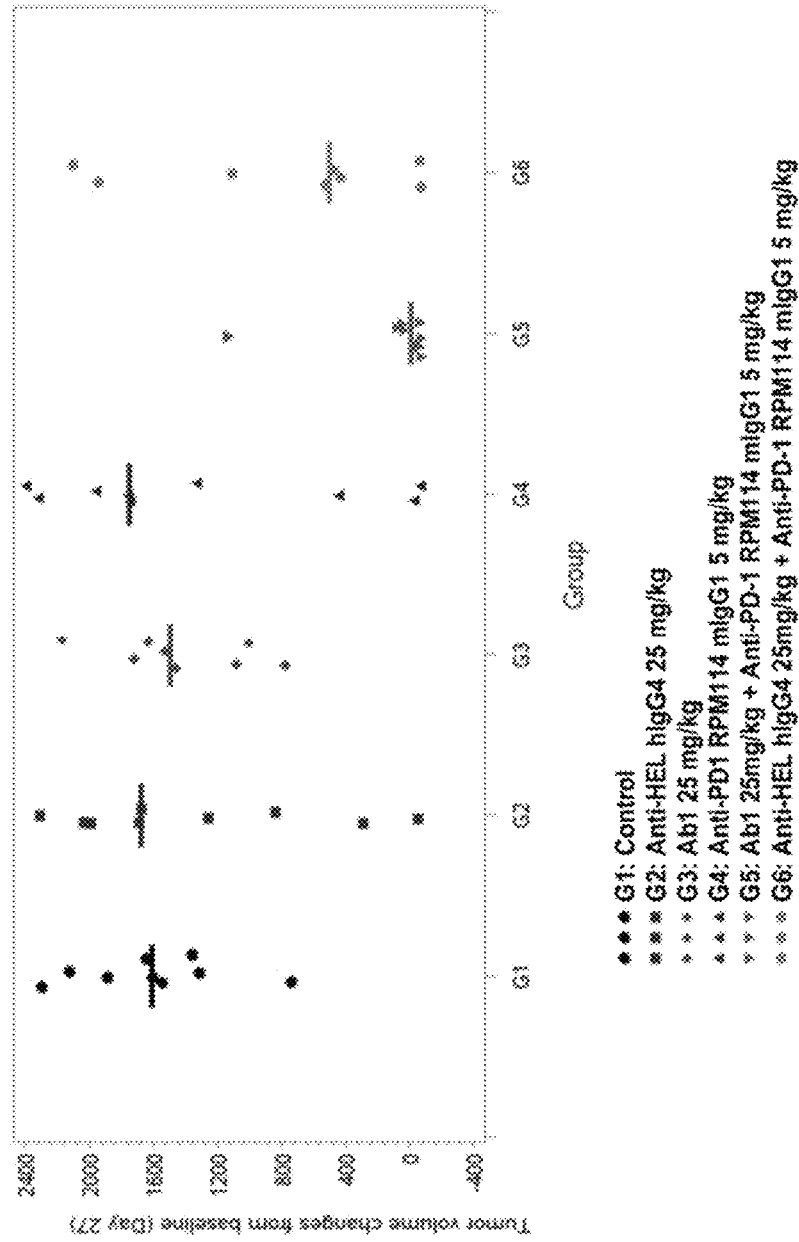
FIG. 6 is a scatter dot graph showing tumor volume changes from baseline on day 27 of indicated treatments using the C57BL/6 MC38 colon mouse model. Control: PBS. "Anti-PD-1 RPM114 mIgG1": x-anti-mPD-1 Mab.
Figure 7A:
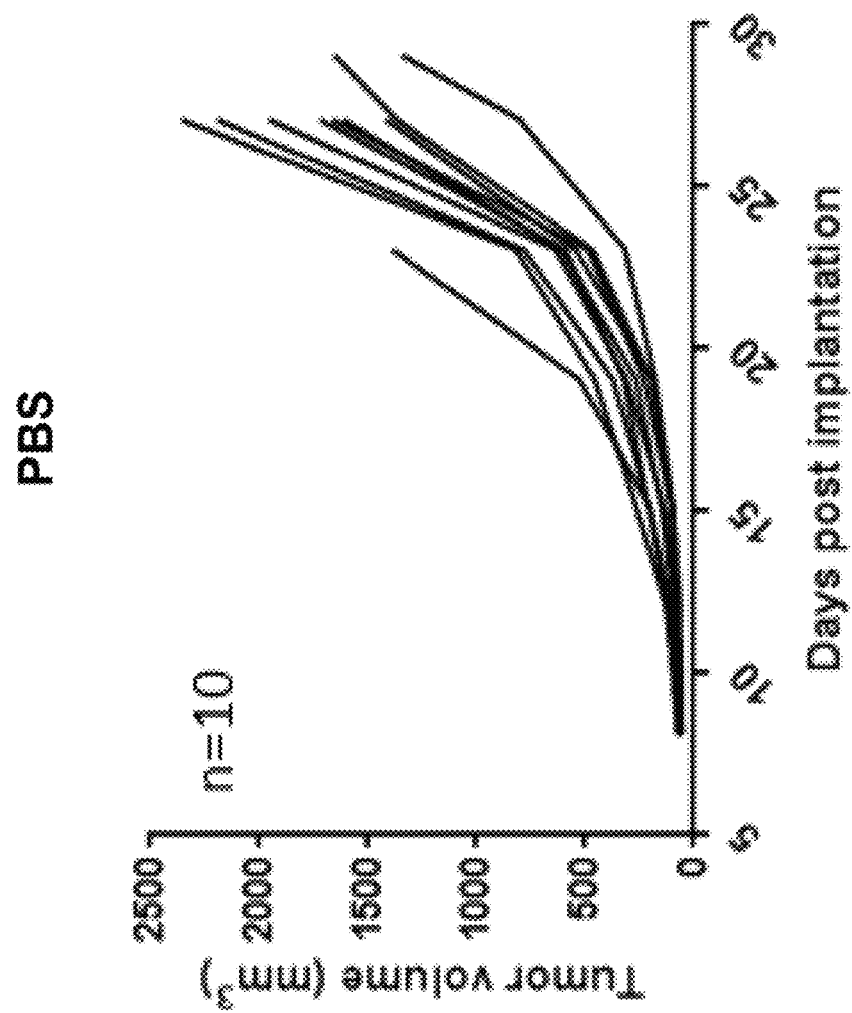
FIGS. 7A-F are graphs showing the tumor volumes over time for each indicated treatment group using the C57BL/6 MC38 colon mouse model. Each line in the graphs represents one animal. "mpk": mg/kg. "Ab1 Isotype Ctrl": anti-HEL hIgG4. αPD1: x-anti-mPD-1 Mab.
Figure 7B:
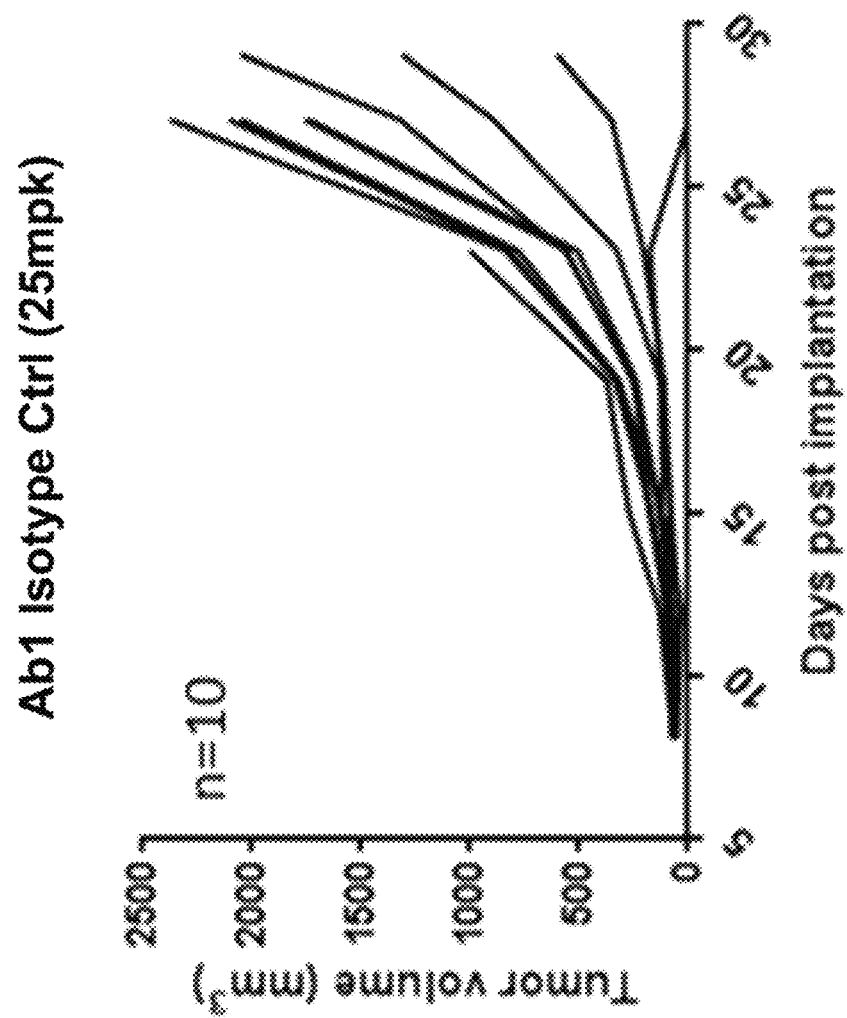
Figure 7C:
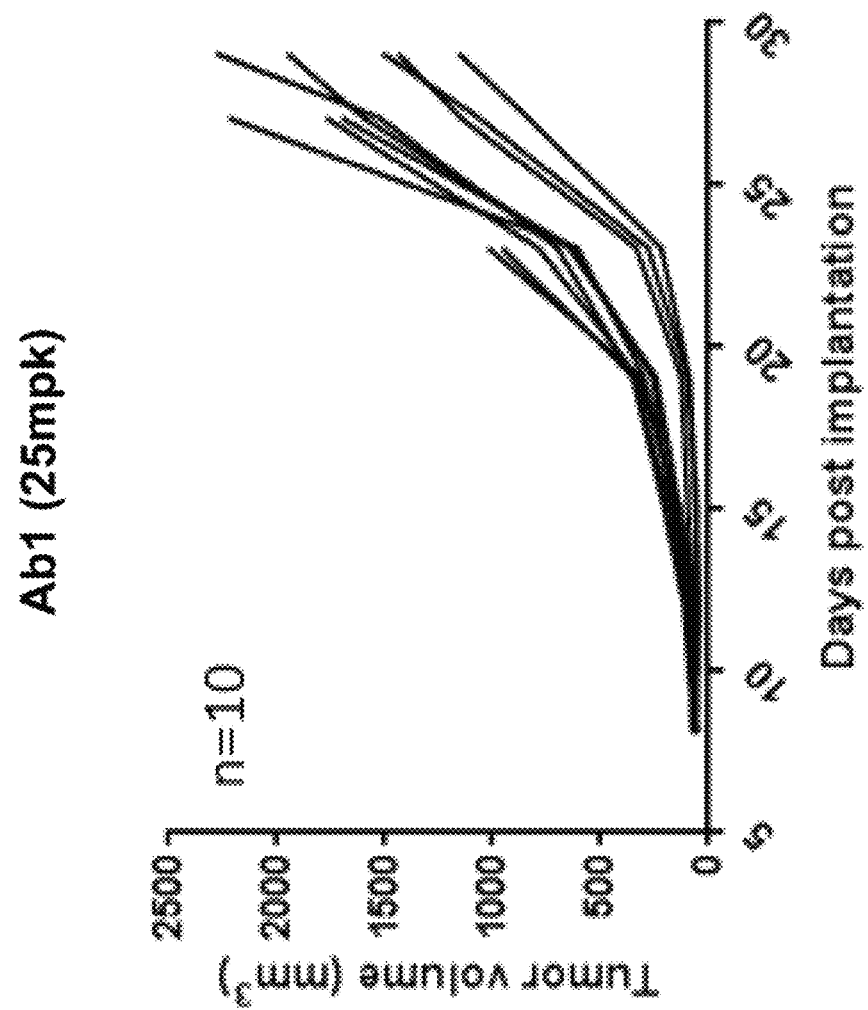
Figure 7D:
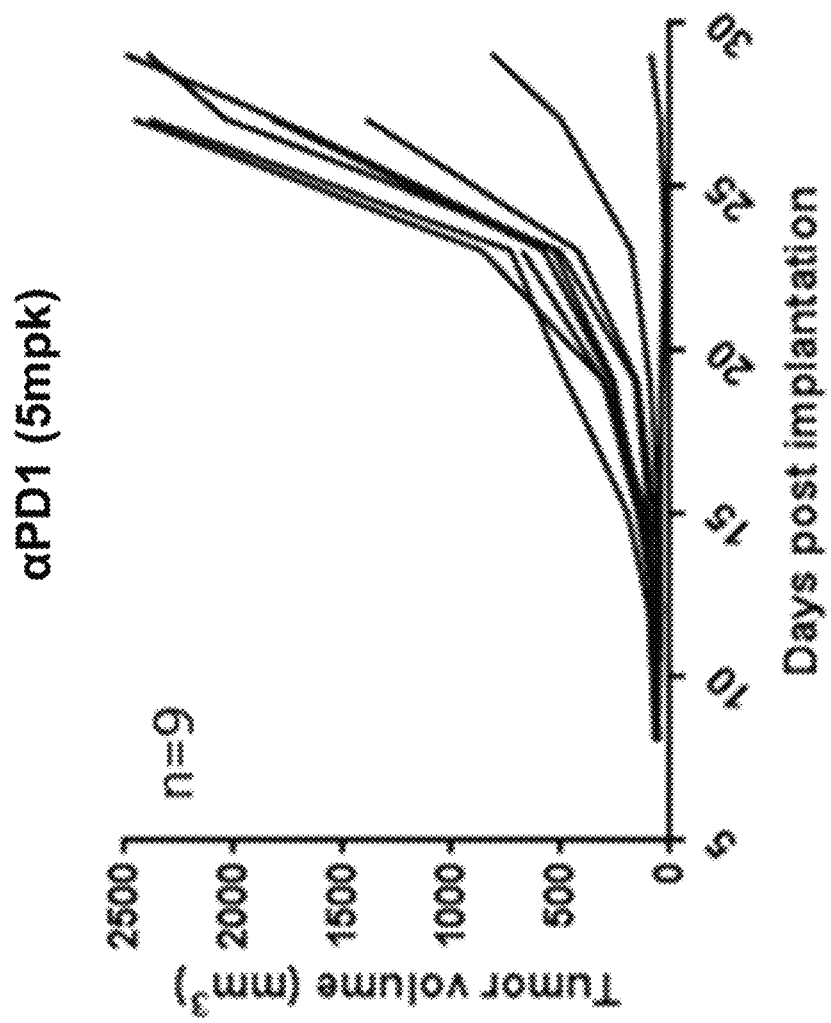
Figure 7E:
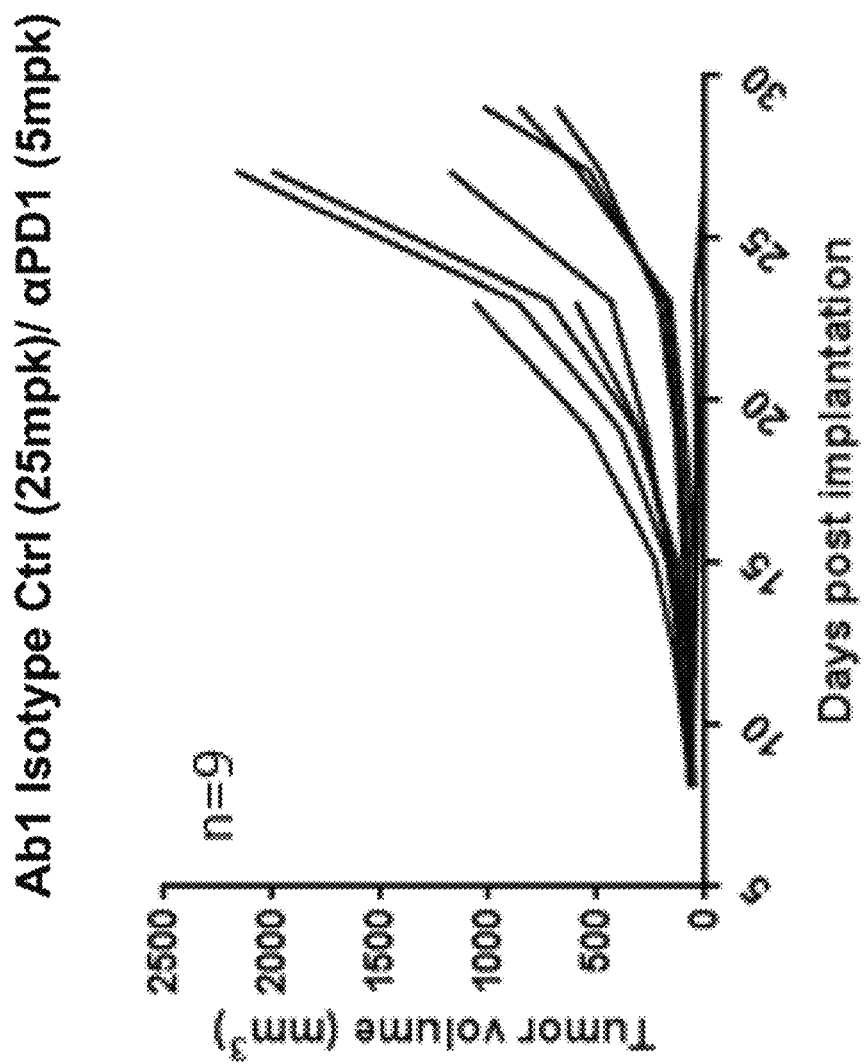
Figure 7F:
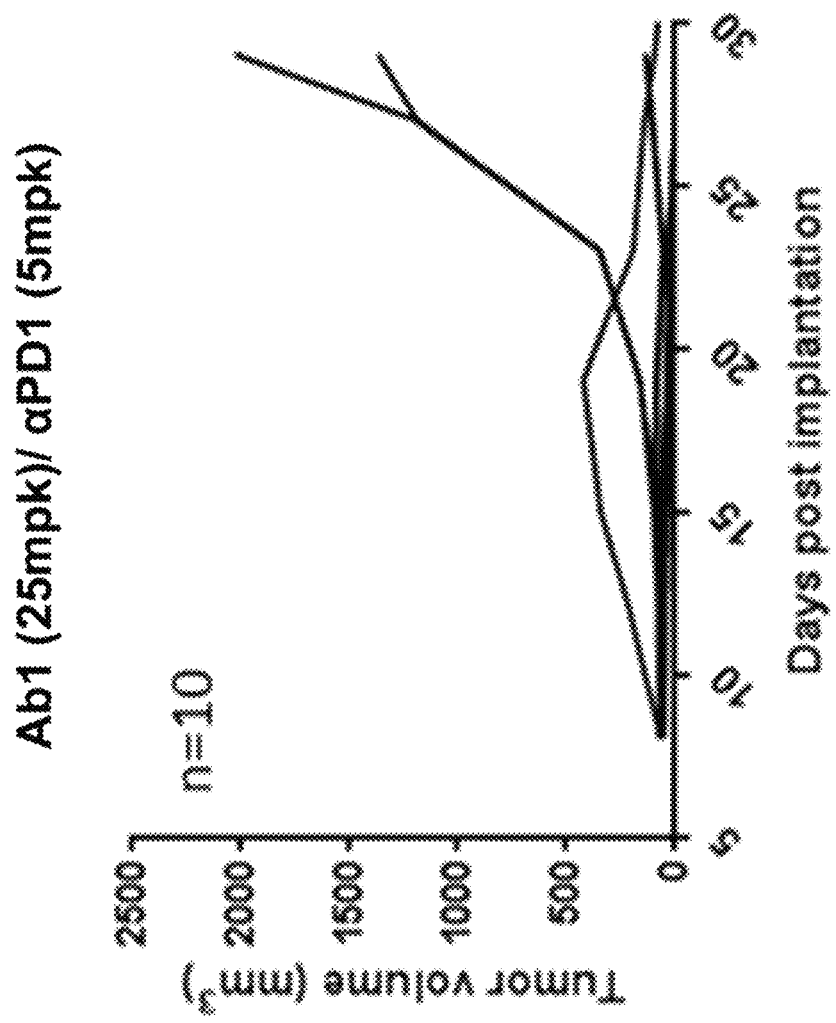

As heterogeneity of variances was observed between groups, the compound symmetric (CS) covariance structure with group=option was chosen for the ANOVA type model (SAS Institute Inc. (2008) SAS/STAT 9.2 User's Guide by Cary N C). In FIGS. 5 and 6, the medians and Median Absolute Deviation (MAD) of each group are represented for each day of measurement. In Table 4-6 below, the medians and Normalized MAD (nMAD=1.4826*MAD) of each group are reported for each day of measurement. All statistical analyses were performed using SAS version v9.2 software. A probability less than 5% ($p<0.05$) was considered as significant.

Efficacy Results

Treatment of tumor-bearing C57BL/6 mice with Ab1, the anti-PD-1 Mab, or a combination of the two was also well tolerated and non-toxic as indicated by the general health and activity of the animals and the lack of significant changes in body weight. As single agents, Ab1 at 25 mg/kg Q3D and the anti-PD-1 Mab at 5 mg/kg Q3D caused body weight loss values at nadir of only 3.4% (day 9) and 2.1% (day 9), respectively. The combination of Ab1 (25 mg/kg Q3D) and the anti-PD-1 Mab (5 mg/kg Q3D) was also well tolerated, showing body weight loss values at nadir of 1.3% (day 9) (Table 4).

As single agents, Ab1 (25 mg/kg Q3D) and the anti-PD-1 Mab (5 mg/kg Q3D) showed no perturbation on tumor growth as compared to animals treated with Ab1 isotype control (anti-HEL hIgG$_4$). The $\Delta T/\Delta C$ ratio at day 27 of treatment was 93% and 109%, respectively (Table 4). The combination of the anti-PD-1 Mab and anti-HEL hIgG$_4$ demonstrated minimal anti-tumor activity with a $\Delta T/\Delta C$ of 31% at day 27 of treatment (not statistically different than control group) and complete regressions observed in only 2 of 10 mice. However, the combination of the anti-PD-1 Mab and Ab1 demonstrated superior anti-tumor activity from day 15 to day 27, with $-1$ $\Delta T/\Delta C$ at day 27 of treatment (statistically different than control group) and complete regressions observed in 6 of 10 mice (Table 4).

TABLE 4

Activity of Ab1 and X-anti-mPD-1 Mab in C57BL/6 MC38 Cancer Model

| Agent | $\Delta W$* (day of nadir) | $\Delta T/\Delta C$ % (Day 27) | Median % of regression (Day 27) | p value** (Day 27) | Regressions (Day 27) PR | CR |
|---|---|---|---|---|---|---|
| Vehicle | −1.8 (D 9) | 100 | — | — | 0/10 | 0/10 |
| Anti-HEL hIgG$_4$ (25 mg/kg) | — | 104 | — | 0.7914 | 1/10 | 1/10 |
| Ab1 (25 mg/kg) | −3.4 (D 9) | 93 | — | 0.9953 | 0/10 | 0/10 |
| x-anti-mPD-1 (5 mg/kg) | −2.1 (D 9) | 109 | — | 0.5435 | 2/10 | 1/10 |
| Ab1 (25 mg/kg) + x-anti-mPD-1 (5 mg/kg) | −1.3 (D 9) | −1 | 24.5 | <0.0001 | 6/10 | 6/10 |
| Anti-HEL hIgG$_4$ (25 mg/kg) + x-anti-mPD-1 (5 mg/kg) | −3.0 (D 9) | 31 | — | 0.4020 | 2/10 | 2/10 |

*$\Delta W$ denotes average body weight change in % per group at nadir.
**The p-values were obtained with a contrast analysis to compare each treated group versus control using Bonferroni-Holm adjustment for multiplicity after a two-way ANOVA-Type with repeated measures on tumor volume changes from baseline. A probability less than 5% ($p < 0.05$) was considered significant.

Tables 5 and 6 and FIGS. 5-7 present additional data showing the activity of the antibodies alone or in combination on tumor volumes in the mouse model.

TABLE 5

Comparison of the Treated Groups to the Control group
Tumor volume changes from baseline mm$^3$: Median (nMAD), n, and p-value*

| Treatment Group | Global | Day 12 | Day 15 | Day 19 | Day 23 | Day 27 |
|---|---|---|---|---|---|---|
| Vehicle | — | 26.0 (20.02) n = 10 | 71.5 (53.37) n = 10 | 220.5 (117.87) n = 10 | 528.0 (157.16) n = 10 | 1610.0 (413.65) n = 9 |
| Anti-HEL hIgG$_4$ (25 mg/kg) | 0.9629 | 17.0 (17.79) n = 10 0.5197 | 65.5 (51.89) n = 10 1.0000 | 182.5 (113.42) n = 10 0.8858 | 491.5 (358.05) n = 10 1.0000 | 1675.0 (621.21) n = 9 0.7914 |

TABLE 5-continued

Comparison of the Treated Groups to the Control group
Tumor volume changes from baseline mm$^3$: Median (nMAD), n, and p-value*

| Treatment Group | Global | Day 12 | Day 15 | Day 19 | Day 23 | Day 27 |
|---|---|---|---|---|---|---|
| Ab1 (25 mg/kg) | — | 17.0 | 79.0 | 218.0 | 567.0 | 1496.5 |
|  | 0.9629 | (15.57) | (43.74) | (83.03) | (344.70) | (472.21) |
|  |  | n = 10 | n = 10 | n = 10 | n = 10 | n = 8 |
|  |  | 0.4754 | 1.0000 | 0.8858 | 1.0000 | 0.9953 |
| X-anti-mPD1 Mab | — | -2.0 | 38.5 | 147.5 | 458.0 | 1748.0 |
| (5 mg/kg) | 0.2439 | (21.50) | (68.20) | (149.74) | (280.21) | (851.01) |
|  |  | n = 10 | n = 10 | n = 10 | n = 10 | n = 9 |
|  |  | 0.0224 | 0.1235 | 0.2259 | 0.2228 | 0.5435 |
| Ab1 | — | -3.5 | 20.0 | -0.5 | -17.0 | -9.0 |
| (25 mg/kg) + | 0.0007 | (10.38) | (20.02) | (69.68) | (51.15) | (86.73) |
| x-anti-mPD-1 Mab |  | n = 10 | n = 10 | n = 10 | n = 10 | n = 10 |
| (5 mg/kg) |  | 0.0743 | 0.0121 | <.0001 | <.0001 | <.0001 |
| Anti-HEL hIgG$_4$ | — | 19.0 | 61.5 | 145.0 | 266.0 | 503.0 |
| (25 mg/kg) + | 0.2531 | (37.81) | (65.98) | (160.12) | (398.82) | (841.38) |
| x-anti-m-PD-1 |  | n = 10 | n = 10 | n = 10 | n = 10 | n = 8 |
| (5 mg/kg) |  | 0.5197 | 0.2848 | 0.2259 | 0.1979 | 0.4020 |

*The p-values were obtained with a contrast analysis versus control at each day with Bonferroni-Holm adjustment for multiplicity after a two-way Anova-Type on tumor volume changes from baseline.

TABLE 6

Ab1 and X-anti-mPD-1 Mab as Single Agents vs. Combination
Tumor volume changes from baseline mm$^3$:
Median (nMAD), n and p-value*

| Treatment Group | Global | Day 12 | Day 15 | Day 19 | Day 23 | Day 27 |
|---|---|---|---|---|---|---|
| Ab1 | — | -3.5 | 20.0 | -0.5 | -17.0 | -9.0 |
| (25 mg/kg) + |  | (10.38) | (20.02) | (69.68) | (51.15) | (86.73) |
| x-anti-mPD-1 Mab |  | n = 10 | n = 10 | n = 10 | n = 10 | n = 10 |
| (5 mg/kg) |  |  |  |  |  |  |
| X-anti-mPD-1 | — | -2.0 | 38.5 | 147.5 | 458.0 | 1748.0 |
| (5 mg/kg) | 0.0405 | (21.50) | (68.20) | (149.74) | (280.21) | (851.01) |
|  |  | n = 10 | n = 10 | n = 1 | n = 10 | n = 9 |
|  |  | 1.0000 | 0.7631 | 0.0276 | 0.0004 | 0.0024 |
| Ab1 | — | 17.0 | 79.0 | 218.0 | 567.0 | 1496.5 |
| (25 mg/kg) | 0.0017 | (15.57) | (43.74) | (83.03) | (344.70) | (472.21) |
|  |  | n = 10 | n = 10 | n = 10 | n = 10 | n = 8 |
|  |  | 1.0000 | 0.0694 | 0.0007 | <.0001 | <.0001 |
| Anti-HEL hIgG$_4$ | — | 19.0 | 61.5 | 145.0 | 266.0 | 503.0 |
| (25 mg/kg) + |  | (37.81) | (65.98) | (160.12) | (398.82) | (841.38) |
| x-anti-mPD-1 Mab |  | n = 10 | n = 10 | n = 10 | n = 10 | n = 8 |
| (5 mg/kg) |  |  |  |  |  |  |
| X-anti-mPD-1 Mab | — | -2.0 | 38.5 | 147.5 | 458.0 | 1748.0 |
| (5 mg/kg) | 0.8680 | (21.50) | (68.20) | (149.74) | (280.21) | (851.01) |
|  |  | n = 10 | n = 10 | n = 10 | n = 10 | n = 9 |
|  |  | 0.2024 | 0.7631 | 0.9476 | 0.8576 | 0.8491 |
| Anti-HEL hIgG$_4$ | — | 17.0 | 65.5 | 182.5 | 491.5 | 1675.0 |
| (25 mg/kg) | 0.5691 | (17.79) | (51.89) | (113.42) | (358.05) | (621.21) |
|  |  | n = 10 | n = 10 | n = 10 | n = 10 | n = 9 |
|  |  | 1.0000 | 0.5743 | 0.4761 | 0.2357 | 0.8491 |

*The p-values were obtained with a contrast analysis to compare the combinations of Ab1, anti-HEL hIgG4 and x-anti-mPD-1 versus each single agent at the dose involved in the combination at each day with Bonferroni-Holm adjustment for multiplicity after a two-way Anova-Type on tumor volume changes from baseline.

The data in the tables and the figures show that the combination of Ab1 at 25 mg/kg Q3D and x-anti-mPD-1 Mab at 5 mg/kg Q3D had greater antitumor effect than either antibody at those doses. This difference was statistically significant, with the p values on days 19, 23, and 27 being 0.0007, <0.0001, and <0.0001, respectively, when comparing the combination to Ab1 as a single agent. This difference was also statistically significant, with the p values on days 19, 23, and 27 being 0.0276, 0.0004, and 0.0024 when comparing the combination to x-anti-m PD-1 Mab as a single agent (Table 6). For the combination group of anti-HEL hIgG$_4$ at 25 mg/kg Q3D and x-anti-mPD-1 Mab at 5 mg/kg Q3D, the treatment effect on tumor volume changes from baseline was not significantly different from the effect of either agent alone at any day of measurement.

In summary, the combination of Ab1 at 25 mg/kg Q3D and anti-m PD-1 Mab at 5 mg/kg Q3D had a significantly greater antitumor effect than either agent used alone from day 15 to day 27.

In another study, we evaluated the antitumor activity of the combination of Ab1 at a dose of 1, 10, or 25 mg/kg and mouse PD-1 antibody at a dose of 5 mg/kg against subcutaneous MC38 mouse colon cancer model in C57BL/6J mice. Exponentially growing MC38 colon adenocarcinoma cells (NCI, Frederick, Md.) were cultured in RPMI-1640 supplemented with 10% FBS in a humidified 5% CO$_2$ incubator and then implanted subcutaneously ($1\times10^6$ cells) into the flank of female C57/Bl6J mice (Jackson Laboratory, Bar Harbor, Me.). Once tumors reached an average size of 50-75 mm³, the mice were pooled and randomly distributed to control and treatment groups (10 mice per group). Tumor-bearing mice were then treated intraperitoneally with PBS, an IgG4 isotype control antibody (25 mg/kg). or Ab1 (1, 10, and 25 mg/kg) three times per week until each animal had received a total of 6 to 7 doses. Tumors were measured with digital calipers 2 times per week and tumor volumes calculated (mm³=L×W×H) and graphed using GraphPad Prism. Mice were euthanized with $CO_2$ at the termination of the study, if tumors grew to >2000 mm³, or if the tumors exhibited ulceration >20% of the tumor surface.

As single agents, Ab1 at a dose of 25 mg/kg Q3D and mouse α-PD-1 antibody at a dose of 5 mg/kg demonstrated partial activity with ⅔ and ⅘ complete regression, respectively, in MC38 tumor bearing mice. The combination of Ab1 at 1, 10, or 25 mg/kg Q3D and mouse α-PD-1 antibodies at 5 mg/kg Q3D was therapeutically active. On day 24 post implantation, when comparing tumor volume changes from baseline, the effect of the combination of Ab1 at all tested doses and mouse α-PD-1 antibodies at 5 mg/kg Q3D was greater than the effect of each single agent with ⅝, ⅚ and ⅞ complete regression for 1, 10, and 25 mg/kg of Ab1, respectively. Table 6A provides a summary of the results.

TABLE 6A

Antitumor Effects of Ab1 + Anti-mPD-1 mAb Combinations

| Group | Treatment | Total Number of Mice | Number of Complete Response/Regression (Complete Response/Regression Rate) |
|---|---|---|---|
| 1. | PBS | 8 | 0 (0%) |
| 2. | 25 mg/kg isotype control antibody for Ab1 + 5 mg/kg isotype control antibody for anti-mPD-1 Mab | 8 | 0 (0%) |
| 3. | 25 mg/kg Ab1 + 5 mg/kg isotype control antibody for anti-mPD-1 Mab | 8 | 2 (25%) |
| 4. | 25 mg/kg isotype control antibody for Ab1 + 5 mg/kg x-anti-mPD-1 Mab | 8 | 4 (50%) |
| 5. | 1 mg/kg Ab1 + 5 mg/kg x-anti-mPD-1 Mab | 8 | 5 (62.5%) |
| 6. | 10 mg/kg Ab1 + 5 mg/kg x-anti-mPD-1 Mab | 8 | 6 (75%) |
| 7. | 25 mg/kg Ab1 + 5 mg/kg x-anti-mPD-1 Mab | 8 | 7 (87.5%) |

In summary, these preclinical data demonstrate that the combination of PD-1 inhibition with TGF-β inhibition is able to inhibit tumor growth to a greater degree than just checkpoint inhibitor blockade alone.

Example 6: Intratumoral TGF-β1 Levels

Intratumoral TGF-β1 levels were studied in a LoVo colorectal cancer subcutaneous xenograft-transplanted BALB/c mouse model. The mice were injected with either Ab1 or isotype control Mab at 10, 25, or 50 mg/kg intravenously every 3 days for a total of eight IV administrations, beginning when the tumor volume was less than 100 mm³.

Tumor samples, which were stored at −80° C. in 2 ml plastic tubes with 2.8 mm ceramic balls (MoBio 13114-50), were thawed at room temperature. One milliliter (ml) of cold Meso Scale Diagnostic (MSD) Tris Lysis buffer (R60TX-2) supplemented with 1× Halt™ Protease and Phosphatase Inhibitor Cocktail (Thermo 78440) was added to the tissue, which was then homogenized using Precellys® 24 Dual homogenizer (Bertin Instruments) in two cycles at 6500 rpm, 20 s each, at 4° C. The lysates were cleared by centrifugation for 10 min at 20,000×g in an Eppendorf 5417C centrifuge at 4° C. The supernatants were transferred into clean chilled Eppendorf tubes and further cleared by centrifugation for another 20 min as described above. After that, the supernatants were transferred into a plastic 96-weel storage block, snap frozen in liquid nitrogen, and stored at −80° C.

The next day the samples were thawed at room temperature and placed on ice. Protein concentration in the lysates was measured using a Bicinchoninic Acid (BCA) Protein Assay kit (Thermo 23225) according to the manufacturer's instructions. Lysates were normalized to a protein concentration of approximately 8 mg/ml by using MSD Tris Lysis buffer with protease and phosphatase inhibitors (see above), and aliquoted in plastic microtubes.

TGF-β1 concentration in normalized tumor lysates was measured according to the manufacturer's instructions using a human TGF-β1 kit (MSD, K151IUC-2) employing electrochemiluminescence assay. Recombinant mouse TGF-β1 (R&D Systems, Cat. #7666-MB-005) serially diluted in MSD Lysis Buffer was used as a calibrator. Samples were loaded on the plate in duplicates. Electrochemiluminescence signal was measured using MESO SECTOR S 600 plate reader (MSD), and the TGF-β1 concentration in the samples was quantified using MSD Discovery Workbench software v4.0 based on the standard curve.

Mean concentration for sample duplicates was calculated by the software. Concentration values determined by the software as "Below Fit Curve Range" or "Below Detection Range" were substituted with zero values. In order to calculate TGF-β1 concentration per mg of total protein, concentration measured in the assay (pg/ml) was divided by protein concentration (mg/ml) in the samples.

Figure 8:
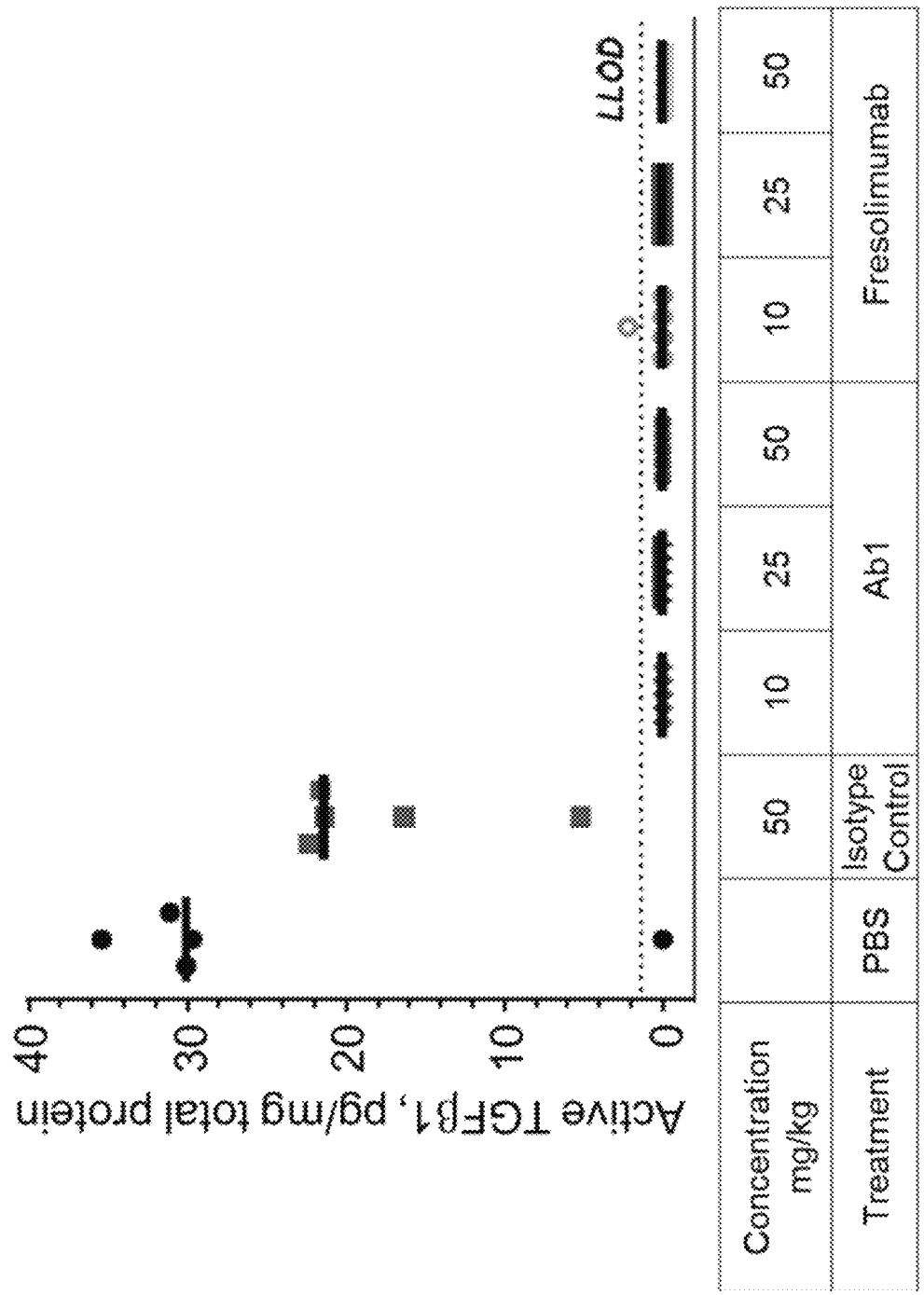
FIG. 8 is a graph showing the effects of Ab1 on active TGF-β1 concentration in LoVo tumor lysates.

The results showed that the intratumoral TGF-β1 levels in mice injected with isotype control had a median of 21.4 pg/mg total protein, the corresponding levels in mice injected with Ab1 was undetectable (FIG. 8).

To demonstrate the relevance of the above findings in humans, we tested ten human colorectal tumor samples and ten human melanoma tumor samples for their intratumoral TGF-β1 levels as described above using the above-described method. For the human CRC samples, TGF-β1 levels ranged from about 7 to 25 pg/mg. For the human melanoma samples, TGF-β1 levels ranged from about 1 pg/mg to as high as 43 pg/mg. These data further support the use of anti-TGF-β1 therapeutics such as Ab1 in treating tumors, alone or in conjunction with other immune checkpoint inhibitors such as anti-PD-1 antibodies.

Example 7: Pharmacokinetic Studies of Ab1

This Example describes the studies that characterized Ab1's pharmacokinetic (PK) profile and compared it to that of fresolimumab. In one study, five groups of cannulated Sprague-Dawley rats were given a single dose of Ab1 or fresolimumab at 5 mg/kg intravenously. Each group had five females and five males. Blood from the rats were collected at 0.25, 6, 24, 48, 72, 144,192, and 240 hours post-dosing. Ab1 and fresolimumab serum concentrations were determined by ELISA. Comparability was determined if the 90% confidence intervals for the AUC ratio (of test material to reference) was within the range of 80% to 125%.

Figure 9A:
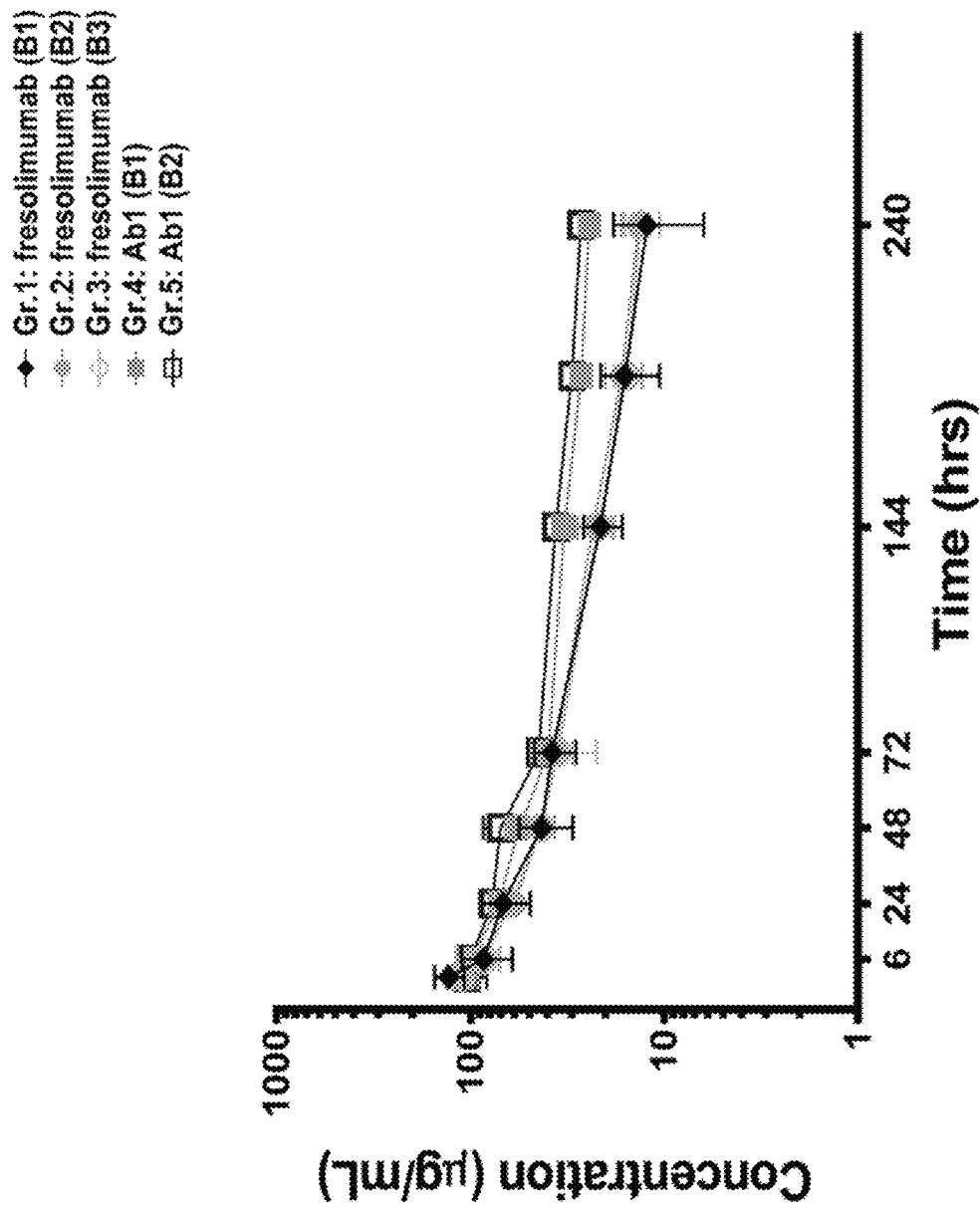
FIG. 9A is a graph showing the serum concentration of Ab1 and fresolimumab over time in five groups of rats given a single dose of either antibody at 5 mg/kg. Groups (Gr.) 1-3 were given three different batches (B1, B2, and B3) of fresolimumab. Groups 4 and 5 were given two different batches (B1 and B2) of Ab1.
Figure 9B:
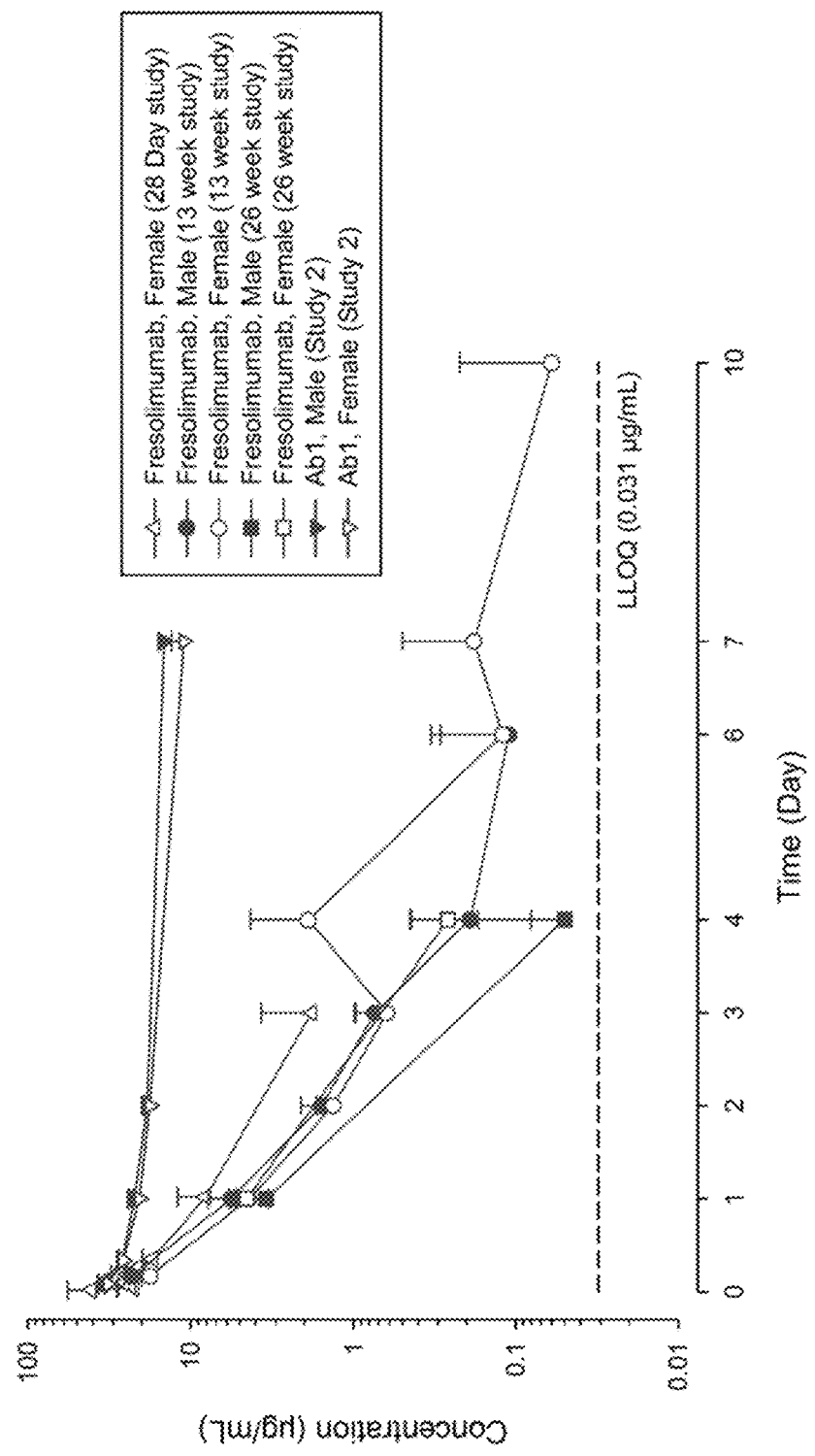
FIG. 9B is a graph showing the serum concentration of Ab1 and fresolimumab over time in monkeys given a single dose of either antibody at 1 mg/kg.
Figure 9C:
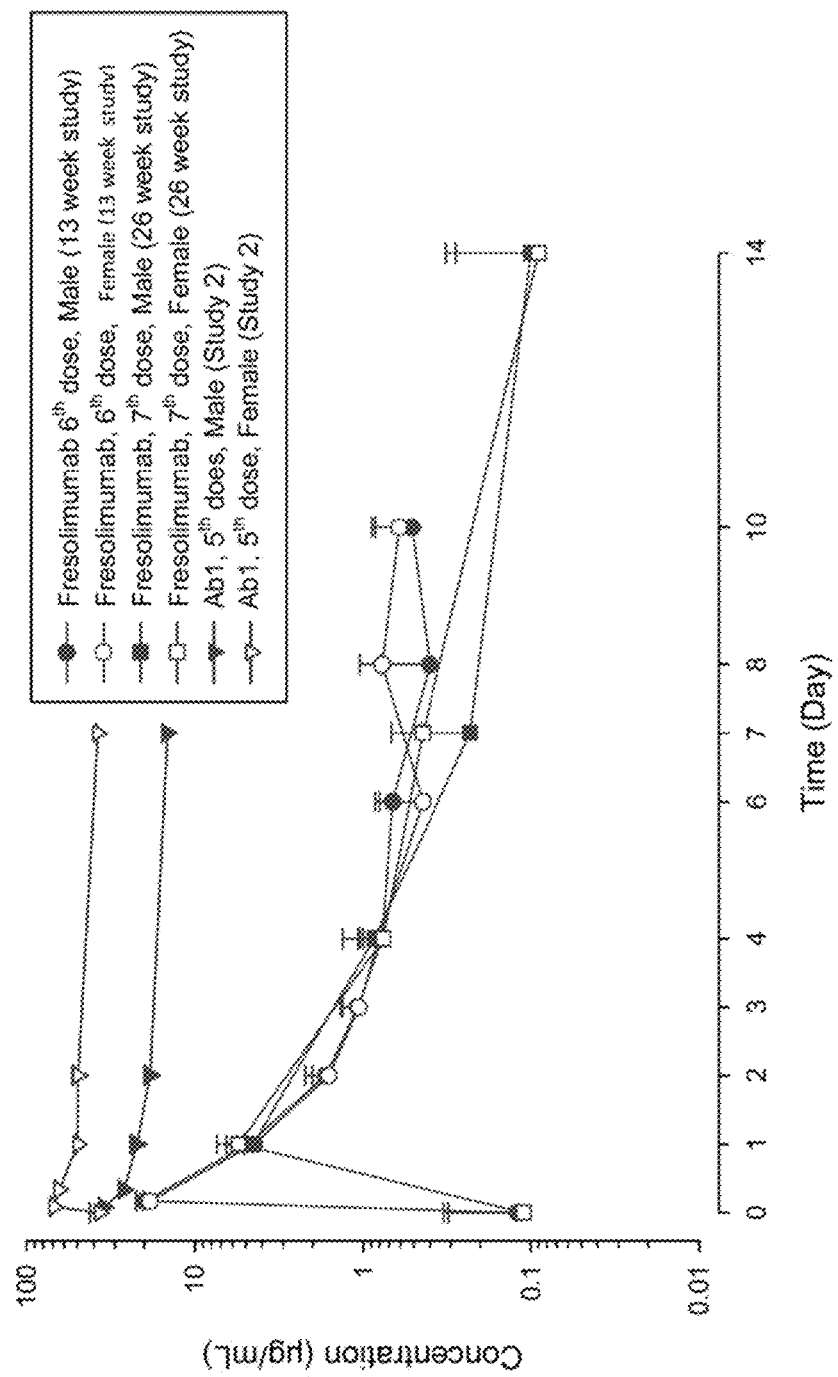
FIG. 9C is a graph showing the serum concentration of Ab1 and fresolimumab over time in monkeys given five weekly doses of Ab1 at 1 mg/kg per dose or biweekly doses of fresolimumab at 1 mg/kg per dose for the indicated duration of studies.
Figure 9D:
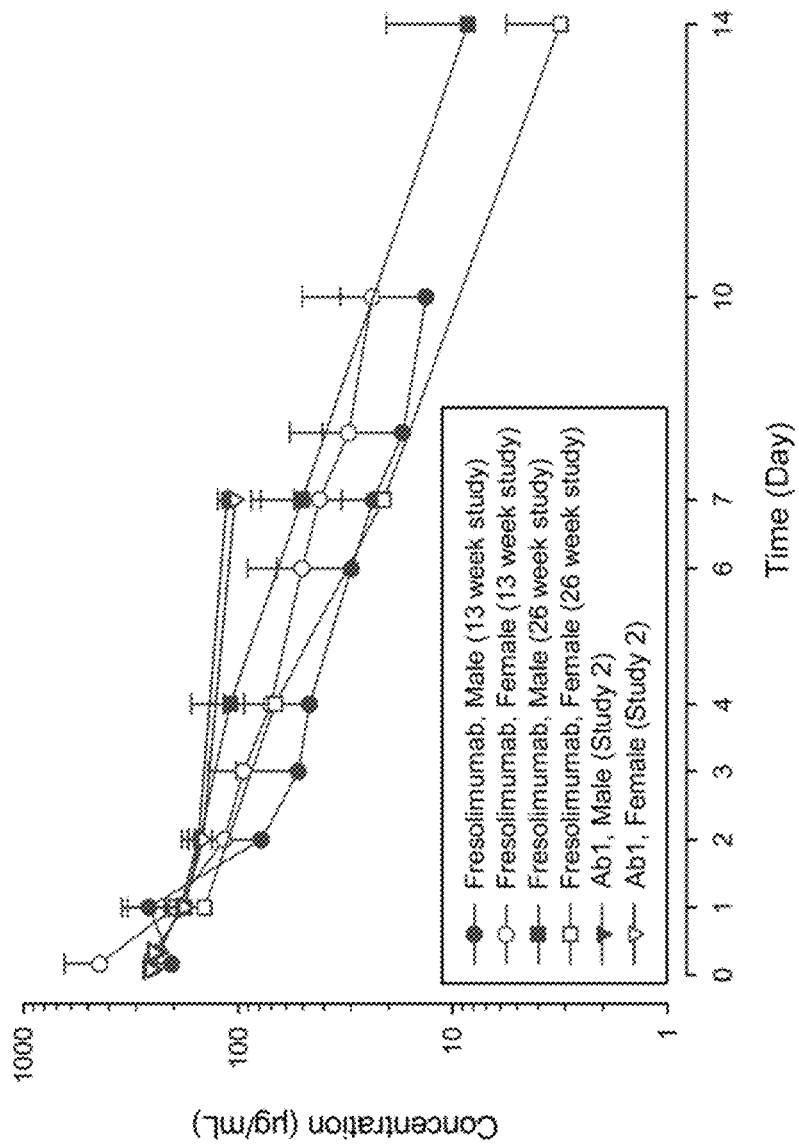
FIG. 9D is a graph showing the serum concentration of Ab1 and fresolimumab over time in monkeys given a single dose of either antibody at 10 mg/kg.
Figure 9E:
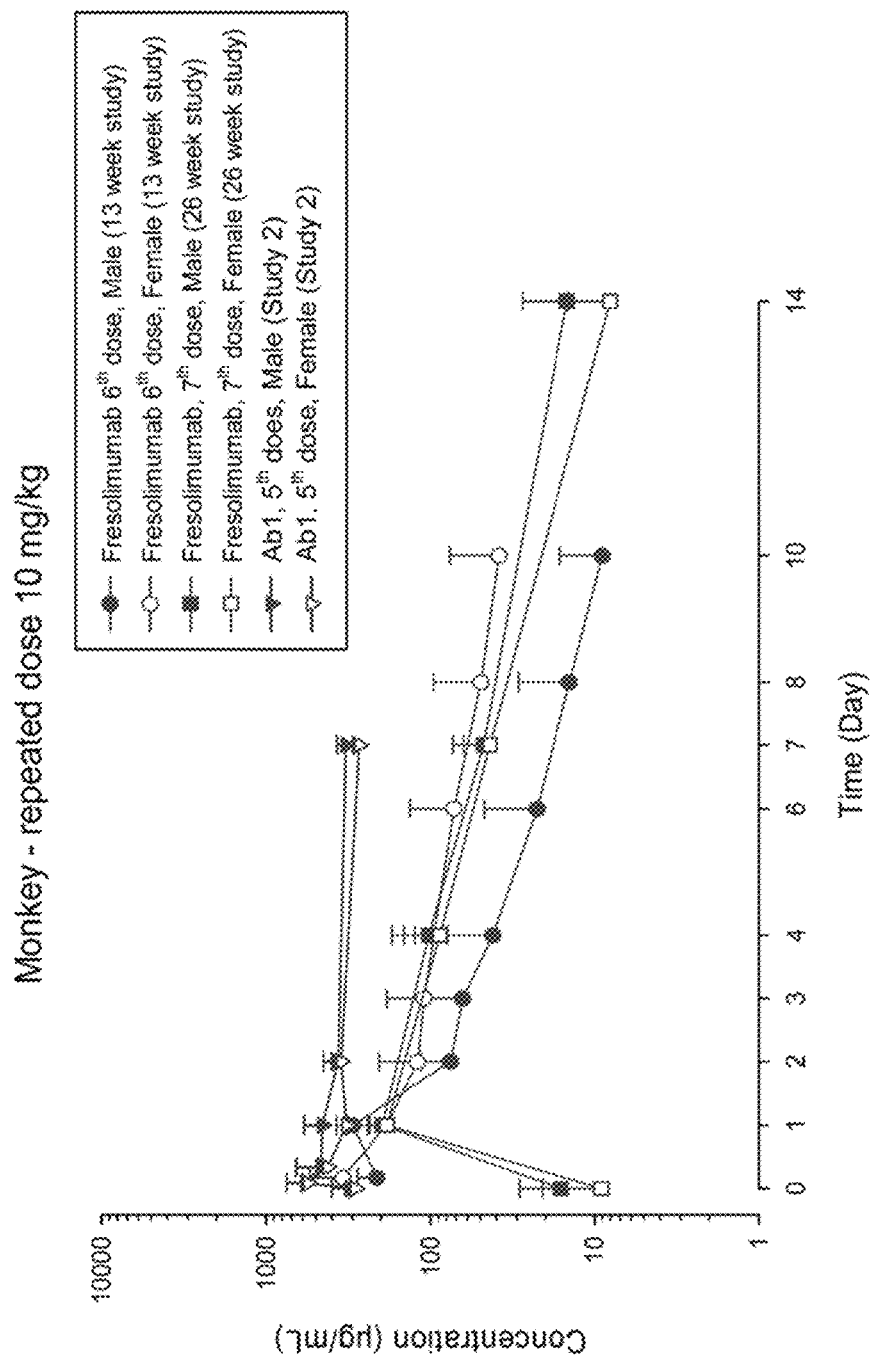
FIG. 9E is a graph showing the serum concentration of Ab1 and fresolimumab over time in monkeys given five weekly doses of Ab1 at 10 mg/kg per dose or biweekly doses of fresolimumab at 10 mg/kg per dose for the indicated duration of studies.

The antibody serum concentrations over time from the five groups of rats are shown in FIG. 9A. PK parameters from groups 2, 4, and 5 (see the legend of FIG. 9A) are shown in Table 7 below. This study showed that Ab1 had linear PK behavior, with a much longer half-life (average $T_{1/2}$ of 7.1 days vs. 4.3 days) and a lower elimination rate (CL of 0.30 ml/hr/kg vs. 0.51 ml/hr/kg) than fresolimumab. The data showed that Ab1 had 1.7-folder higher exposure in rats than fresolimumab.

TABLE 7

PK Comparison Between Fresolimumab and Ab1

| PK Parameters | Fresolimumab (batch 2) | Ab1 (batch 1) | Ab1 (batch 2) |
|---|---|---|---|
| $t_{1/2}$ (hr) | 103.21 ± 12.98 | 181.83 ± 80.92* | 158.38 ± 66.73 |
| Cmax (µg/mL) | 114.56 ± 16.42 | 116.60 ± 16.78 | 109.72 ± 18.49 |
| Vz (mL/kg) | 75.22 ± 15.21 | 78.35 ± 26.33 | 63.47 ± 10.65 |
| CL (ml/hr/kg) | 0.51 ± 0.10 | 0.31 ± 0.04* | 0.30 ± 0.05* |
| $AUC_{last}$ (hr * µg/mL) | 8046 ± 1210 | 10007 ± 1180* | 11223 ± 1035* |
| $AUC_{0-INF}$ (hr * µg/mL) | 10107 ± 1613 | 16322 ± 2523* | 17553 ± 4130* |

*The group means ± SD is statistical different from the "fresolimumab (B2)" group (Group 2 in FIG. 9A).

An additional PK study on Ab1 (Study 2) was conducted in groups of cynomolgus monkeys. Each group had five females and five males, and was given by intravenous infusion a single dose of Ab1 at 1 mg/kg (FIG. 9B) or 10 mg/kg (FIG. 9D), or five weekly doses of Ab1 at 1 mg/kg (FIG. 9C) or 10 mg/kg (FIG. 9E) per dose. The serum concentrations over time of Ab1 in the monkeys are shown in FIGS. 9B-E. The serum concentrations over time of fresoliumamb given to monkeys at single or repeated Q2W (biweekly) doses in previous studies are also shown in the figures for comparison. These data showed that Ab1 also had linear PK behavior in monkeys and displayed higher exposure after both single and repeated dosings than did fresolimumab at both 1 mg/kg and 10 mg/kg per dose. At the single dosing of 10 mg/kg, Ab1 had a half-life of 13 days, whereas fresolimumab had a half-life of 4.5 days; Ab1 had a CL of about 0.40 ml/hr/kg, whereas fresolimumab had a CL of 0.66 ml/hr/kg. Like the rat study, the monkey study also showed Ab1 had about 1.7-folder higher exposure than fresolimumab.

The above described studies demonstrate that Ab1 has a statistically significant longer half-life, a longer clearance time, and higher biological exposure in vivo than fresolimumab.

Further, a study in Ab12 tumor bearing Balb/C mice showed that Ab1 had similar PK profiles whether it was administered intravenously or intraperitoneally.

Using allometric scaling on a two-compartment model, we predicted the following PK parameters in a man of 70 kg based on the monkey data (Table 8):

TABLE 8

Allometric Modeling of PK Parameters

| PK Parameters | Ab1 in Monkeys | Ab1 in Humans |
|---|---|---|
| $T_{1/2}$ (day) | 13.1 | 20.9 |
| CL (ml/hr/kg) | 0.392 | 5.7 |
| V1 (central compartment) (L) | 0.104 | 2.43 |
| Q (ml/hr) | 3.18 | 46 |
| V2 (peripheral compartment) (L) | 0.0693 | 1.62 |

The predicted PK parameters of Ab1 are also more favorable than those of fresolimumab in humans. For example, fresolimumab, with a CL of 12.3 ml/hr/kg in humans, has a faster clearance rate than Ab1.

Example 8: Toxicology Studies of Ab1

Toxicology studies of Ab1 were conducted in rats and cynomolgus monkeys. Safety pharmacology endpoints were evaluated in the repeat-dose GLP (good laboratory practice) weekly for 5 weeks. At doses up to 10 mg/kg/dose (concentration of 2 mg/ml) in monkeys and up to 30 mg/kg/dose (concentration of 6 mg/ml) in rats, no Ab1-related histopathologic findings were seen at the injection sites. No Ab1-related effects were noted in this study at any dose level tested at neurological examinations, on body temperature, respiration rate, blood pressure and ECG parameters.

The NOAEL (no observed adverse effect level) for rats was found to be 3 mg/kg/dose in weekly repeat dosing for 5 weeks, and STD10 (a severely toxic dose that causes death or irreversible severe toxicity in 10% of animals) was found to be between 3 and 10 mg/kg/dose for rats. Toxicity included heart valve proliferation characterized by multiple thickened nodules; and abnormal lung conditions such as mixed cell alveolar exudate, mixed cell perivascular infiltrates, hypertrophy of the muscular arteries, hemorrhage, and/or increased lung weight.

The NOAEL and HNSTD (i.e., the highest nonseverely toxic dose above which lethality, life-threatening toxicities, or irreversible toxicities occur) doses for monkeys in weekly repeat dosing for 5 weeks were found to be 10 mg/kg/dose (cf fresolimumab, whose NOAEL in monkeys was shown to be 1 mg/kg when administered biweekly for 7 or 13 doses, or Q3D for 4 weeks). See also the data shown in Table 9 below.

TABLE 9

Summary of Toxicology Studies in Rats and Monkeys

| Toxicology Parameters | Rats | Monkeys |
|---|---|---|
| LD (Lethal Dose) | 50 mg/kg/dose[1] | >10 mg/kg/dose |
| HNLD (Highest Non-Lethal dose) | 30 mg/kg/dose | 10 mg/kg/dose |
| STD10 | 3-10 mg/kg/dose | NA |
| HNSTD | NA | 10 mg/kg/dose |
| NOAEL | <3 mg/kg/dose | 10 mg/kg/dose |
| Main target organs (histopathology) | Heart, lungs, bones, teeth | None identified |

[1]based on exploratory study
NA: Not applicable

Based on the above toxicology data, it is expected that Ab1 can be administered to human patients safely at a dosage level of about 0.05 mg/kg to 0.5 mg/kg weekly or less frequently, e.g., biweekly.

Example 9: In Vivo Efficacy of Anti-TGF-β Monotherapy

In this study, we investigated the effect of 1D11, a mouse $IgG_1$ anti-bovine TGF-β antibody that cross-reacts with human and mouse TGF-β1, 2, and 3, on a metastatic syngeneic tumor model. In this model, B16-F10 mouse melanoma cells were introduced into the footpad of the C57BL/6 mice by IV and formed metastases in the draining lymph node of the mice. While treatment with control antibody, 13C4, had no effect, treatment with 50 mg/kg 1D11 three times a week beginning one day after tumor inoculation completely abrogated metastases.

To investigate the role of the immune response, mice deficient in the β2-microglobulin gene and therefore lacking CD8$^+$ cytotoxic T cell responses were implanted with B16-F10 in the footpad and treated as before. In contrast to the results seen in immune competent mice, 1D11 had no effect on the number of metastases in the draining lymph node in these mice. These results suggest that the mechanism of action of TGF-β inhibition relies on adaptive cellular immunity.

Example 10: TGF-β Signatures in Cancers

Previous studies have shown that melanoma patients who failed to respond to anti-PD-1 therapy have a transcription signature IPRES (Hugo et al., Cell (2016) 165:35-44). To investigate the mechanism of innate resistance to anti-PD-1 monotherapy, we studied the transcription signatures of nonresponders vs. responders. We found that comparisons of these profiles using Gene Set Enrichment Analyses to a database with more than 1M profiles revealed a strong correlation between anti-PD-1 response and activation of TGF-β signaling in tumors. These data suggest that at baseline in melanoma, TGF-β is associated with innate resistance to anti-PD-1 monotherapy.

Further, we found not only that there was a correlation between anti-PD-1 response and activation of TGF-β signaling, but also that the correlation was strong (R=0.59, p-value by t-test <9E-4). Therefore, we arrived at our gateway indication 1: TGF-β mediated immune suppression in melanoma (e.g., metastatic melanoma) may contribute to innate resistance. Moreover, we found that TGF-β induced gene expression changes were quenchable by 1D11 treatment, confirming the specificity of TGF-β activation signature. These results provide support for the benefits of using anti-TGF-β and anti-PD-1 therapeutics in combination to treat cancer patients who do not respond to anti-PD-1 monotherapy.

Analysis of this correlation across other tumor types beyond melanoma revealed that mesenchymal tumors (e.g., CRC, HCC, head and neck squamous cell carcinoma, and ovarian cancer) also were enriched for both TGF-β activation and predicted anti-PD-1 resistance. This finding was consistent with the role of TGF-β signaling in EMT. Therefore, we arrived at our gateway indication 2: Mesenchymal tumors, especially those with immune infiltration, may benefit from anti-TGF-β and anti-PD-1 combination therapy. Machine learning methods were used to identify from over 30 EMT marker genes a smaller number of genes, for example, ACTA2, VIM, MGP, ZEB2, and ZWINT, that could be used to select mesenchymal tumors. ACTA2 and VIM, for example, were found to be transportable across tumor types. Accordingly, the TGF-β activation transcriptional signature and genes within the signature may serve as useful biomarkers for cancer patient selection at baseline for anti-TGF-β and anti-PD-1 antibody combination therapy.

To study biomarkers in tumor microenvironment, the immune contexture of patient tumors was evaluated using MultiOmyx, a multiplex IHC assay, on CRC and melanoma. Multiplexing was conducted with 12 biomarkers (jointly describing 22 immune cell types) on single FFPE section from each tumor sample. The studies included a range of inflammation to evaluate how well the analytics assess each tumor type and correlate to possible treatment effects. Statistical methods were developed to assess differences at the cell population level, including replicate concordance, volcano plots for analyses of variance, and correlation matrices. The MultiOmyx assay demonstrated excellent technical reproducibility and precision, a favorable dynamic range, inflammation status differences in select immune cells and regions of interest, and included both positive and negative correlations between cell populations.

Example 11: Changes in TGF-β1, MIP-2 and KC/GRO in MC38 Tumors Following Treatment with Ab1 with or without Anti-PD1

In order to demonstrate neutralization of TGF-β, the ability of Ab1 (with or without anti-PD-1) to impact the expression of cytokines in tumors was evaluated.

MC38 tumor-bearing mice were treated with a single dose of either PBS or anti-PD-1 alone (5 mg/kg), or increasing doses of Ab1 (10, 25 or 50 mg/kg, i.p.) in combination with anti-PD-1 (5 mg/kg) when the volume of the tumors was from 61 to 110 mm$^3$. Tumors were collected 1 hour, 6 hours, 10 hours, 24 hours, 72 hours, and 168 hours after the treatment, snap frozen in 2 ml plastic tubes with 2.8 mm ceramic balls (Precyllys KT3961-1007.2), and stored at −80° C. To prepare lysates, tumors were thawed at room temperature. One mL of cold Meso Scale Diagnostics (MSD) Tris Lysis buffer (R60TX-2) supplemented with 1× Halt™ protease and phosphatase inhibitor cocktail (Thermo 78440) was added to the tissue, which was then homogenized using Precellys®24 Dual homogenizer (Bertin Instruments) in 2 cycles at 6,500 rpm, 20 s each, at 4° C. Lysates were cleared by centrifugation for 10 min at 20,000×g in an Eppendorf 5417C centrifuge at 4° C. Supernatants were transferred into clean chilled Eppendorf tubes and further cleared by centrifugation for another 30 min as described above. Supernatants were transferred into a plastic 96-weel storage block and placed on ice. Protein concentration in the lysates was measured using Bicinchoninic Acid (BCA) protein assay kit (Thermo 23225) according to the manufacturer's instructions. Lysates were normalized to approximately 5 mg/ml protein concentration using MSD Tris Lysis buffer with protease and phosphatase inhibitors (see above), aliquoted in plastic microtubes, snap frozen in liquid nitrogen, and stored at −80° C.

Concentrations of active TGFβ-1 in tumor lysates were measured using Human TGFβ-1 Kit (MSD, K151IUC-2) employing electrochemiluminescence assay. Recombinant mouse TGFβ-1 (R&D Systems 7666-MB-005) serially diluted in MSD Lysis Buffer was used as calibrator. Normalized tumor lysates prepared as described above were thawed, and the assay was performed according to the manufacturer's instructions. The acid treatment of the samples was not done in order to quantitate only the active form of TGFβ-1 present in tumors rather than the total TGFβ-1, which includes TGFβ-1 in complex with Latency Associated Peptide. Samples were loaded on the plate in duplicates. Electrochemiluminescence signal was measured using MESO SECTOR S 600 plate reader (MSD), and the TGFβ-1 concentration in the samples was quantified using MSD Discovery Workbench software v. 4.0 based on the standard curve.

Figure 10A:
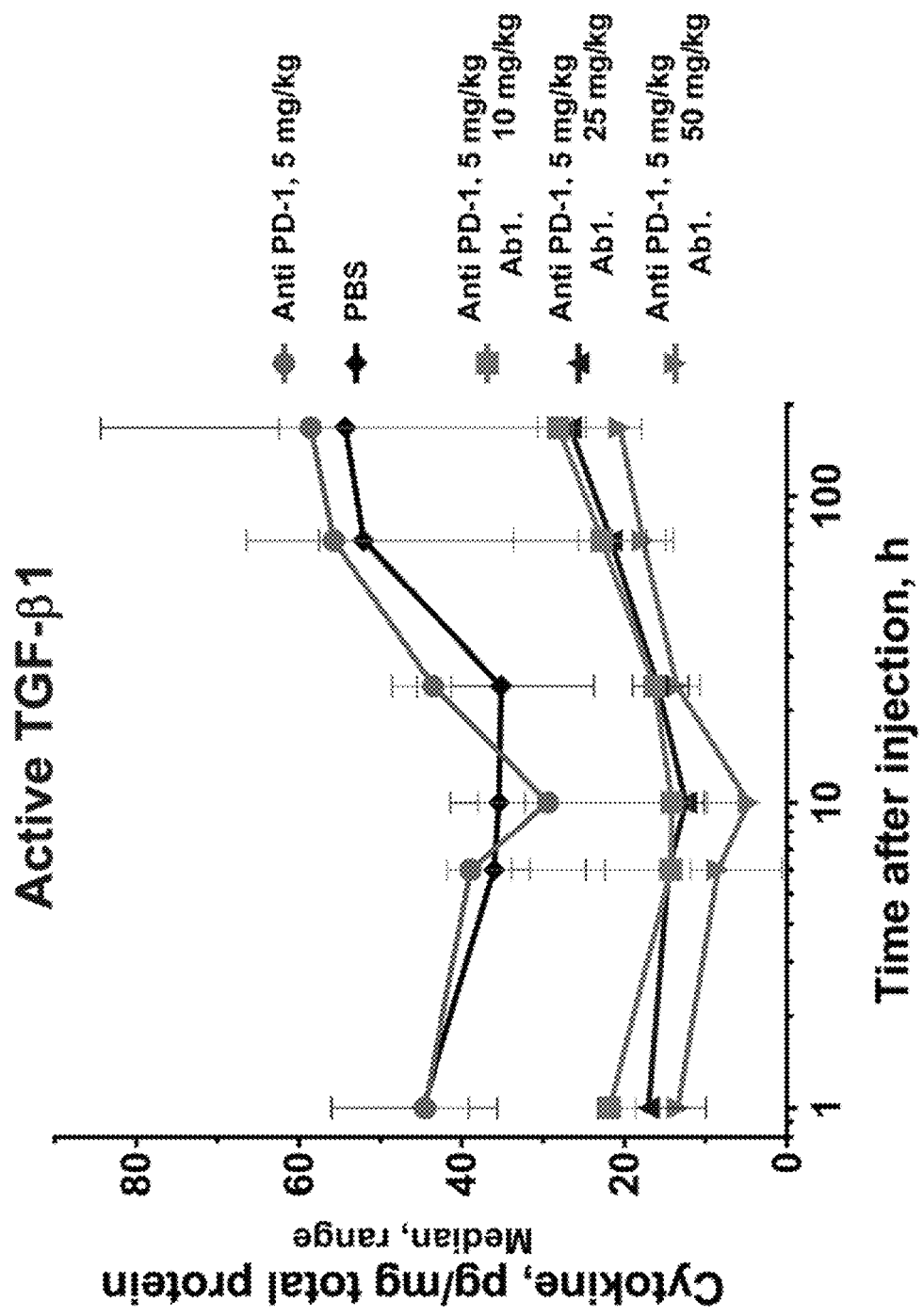
FIG. 10A is a graph showing changes in the levels of TGF-β1 in MC38 tumors following treatment with Ab1 (+/− anti-PD1).

Compared to animals treated with either PBS or anti-PD-1 alone, animals treated with Ab1 at all dosing levels (10, 25, or 50 mg/kg) together with anti-PD-1 (5 mg/kg) were shown to have decreased levels of active TGF-β1 in the tumors, demonstrating the engagement of Ab1 with its target in vivo (FIG. 10A). Decreased levels of active TGF-β1 were observed within one hour and persisted for at least 168 hours.

Figure 10B:
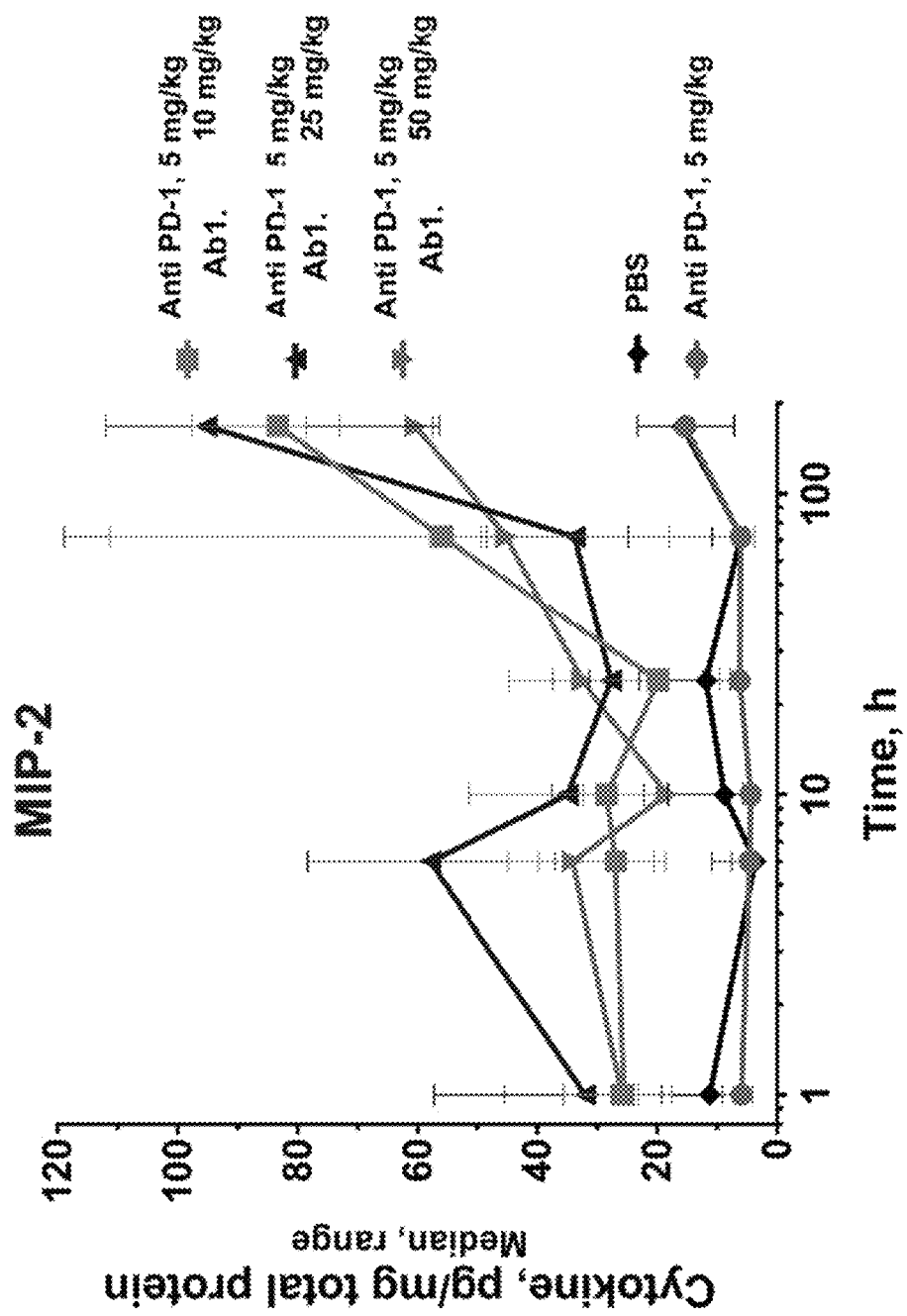
FIG. 10B is a graph showing changes in the levels of MIP-2 in MC38 tumors following treatment with Ab1 (+/− anti-PD1).
Figure 10C:
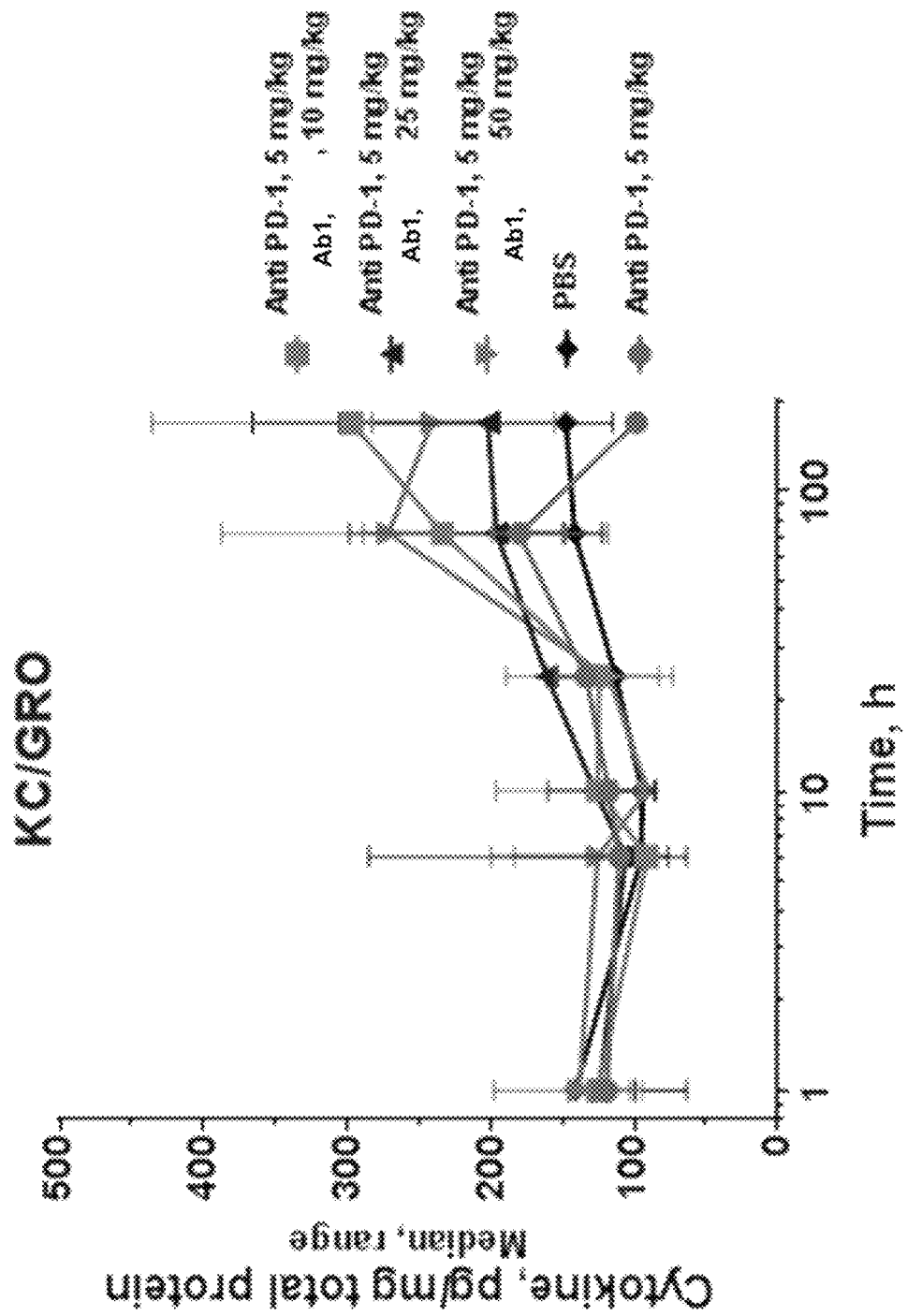
FIG. 10C is a graph showing changes in the levels of KC/GRO in MC38 tumors following treatment with Ab1 (+/− anti-PD1).

MIP-2 (CXCL2) and KC/GRO (CXCL1) are chemotactic chemokines for granulocytes including neutrophils. The levels of MIP-2 and KC/GRO were also evaluated in these same samples. Following the treatment of Ab1 together with anti-PD-1, the intratumoral levels of MIP-2 were shown to increase by at least 4-fold in animals treated with Ab1 together with anti-PD-1, compared to those in animals treated with either PBS or anti-PD-1 alone; and the elevation of MIP-2 levels was shown to persist for at least 168 hours (FIG. 10B). Similarly, the levels of KC/GRO were shown to increase, though at later time points of 72 and 168 hours as compared to those of MIP-2 (FIG. 10C). Thus, the Ab1 and anti-PD-1 mAb combination induced a decrease in the levels of active TGF-β1 earlier than the increase in the levels of MIP-2 and KC/GRO. These results demonstrate that Ab1 can decrease the levels of, and inhibit, TGF-β within the tumor microenvironment. Additionally, the observed increases in MIP-2 and KC/GRO levels indicate that they are cytokines impacted by neutralization of TGF-β and can thus serve as potential biomarkers in patients treated with Ab1.

Example 12: Restoration of NK Cell Clustering by Ab1 Treatment

TGF-β is known to impact the immune system by inhibiting the activities of different immune cell types. TGF-β has been reported to inhibit natural killer (NK) cell activity and NK cell-mediated ADCC (Trotta et al., Journal of immunology (2008) 181:3784-3792). NK cells have recently been reported to form dense clusters as a mechanism to enhance their activity and activation via localization of IL-2 within these densely packed clusters (Kim et al., Scientific Reports (2017) 7:40623). Purified human NK cells cultured in vitro in the presence of IL2 are shown to form these densely packed clusters.

In the present study, we evaluated the effects of TGF-β in the absence or presence of Ab1 on NK cell "clustering." NK cells were freshly isolated from the blood of healthy donors by negative selection with the NK cell RosetteSep reagent according to the manufacturer's protocols (Stem Cell Technologies). NK cells were cultured at $1.2 \times 10^5$ cells/well in IL-2 (100 IU/mL) supplemented Myelocult (Stem Cell Technologies) in round bottom assay plates (Costar). TGF-β1 was added to a final concentration of 0.1, 1 or 10 ng/mL in the presence of either an irrelevant IgG4 or Ab1 at 100 µg/mL, as indicated. The cells were cultured for 72 hours and NK cell clustering was visualized by capturing images on a Nikon microscope.

The addition of increasing doses of TGF-β1 was shown to inhibit NK cell clustering. When Ab1, but not an IgG4 control antibody, was added to the NK cell cultures, the NK cell clusters were shown to develop. This result demonstrates that TGF-β neutralization impacts NK cell activation, leading to increased activity and proliferation of NK cells to support the anti-tumor response of the immune system.

Example 13: Reversion of TGF-β-Mediated Suppression of IFN-γ Production in Proliferating CD8+T Cells by Ab1 Treatment In addition to the innate immune systems, TGF-β has been reported to inhibit the activity of CD8+ T cells (Flavell et al., Nature Reviews Immunology (2010) 10:554-567). To explore the role of TGF-β and Ab1 on CD8+ T cell activity, a MLR (mixed lymphocyte reaction) assay system was established in which purified human CD3+ cells were mixed with BLCL cells. CD8+ cell proliferation and IFN-γ production were first assessed in the presence of TGF-β. Specifically, CD3+ cells were isolated using EasySep T Cell enrichment kit (StemCell Technologies) from PBMCs fractionated from normal healthy donors following Ficoll gradient isolation. The CD3+ cells were then labeled with CellTrace Violet according to the manufacturer's protocol (Thermo-Fisher). An MLR assay was performed by mixing the labeled CD3+ cells ($2 \times 10^5$ cells) with irradiated BLCL cells (Astarte Bio) ($2 \times 10^4$ cells; 2 min) in RPMI supplemented with 10% FBS. TGF-β1, IgG4 control antibody and/or Ab1 were added to the cultures, as indicated, and the cultures were incubated at 37° C. with 5% $CO_2$ for 4 days. The cells were next stimulated for 4 hours in the presence of PMA cell stimulation cocktail (eBioscience) and protein transporter inhibitor cocktail (eBioscience). Live cells were discriminated by staining with Zombie NIR viability dye (BioLegend) on ice and washed with FACs buffer. Cells were fixed with True-Nuclear buffer (BioLegend), washed, pelleted and resuspended in FACs buffer. Cells were prepared for flow cytometry by staining with BV650 Anti-huCD4, PERCP/Cy5.5 anti-huCD8, FITC anti-huCD3, and PE anti-huIFNγ (BioLegend). Flow Cytometry was run on a BD Canto and results analyzed in FlowJo software and gating on live cells, singlets, and CD3+ cells. The percentage of IFNγ+CD8+ T cells was quantitated by gating on the CD8+ cells that had proliferated based upon diminished CellTrace Violet staining and were positive for IFN-γ staining. FMOs were run as controls for all antibody staining.

Figure 11A:
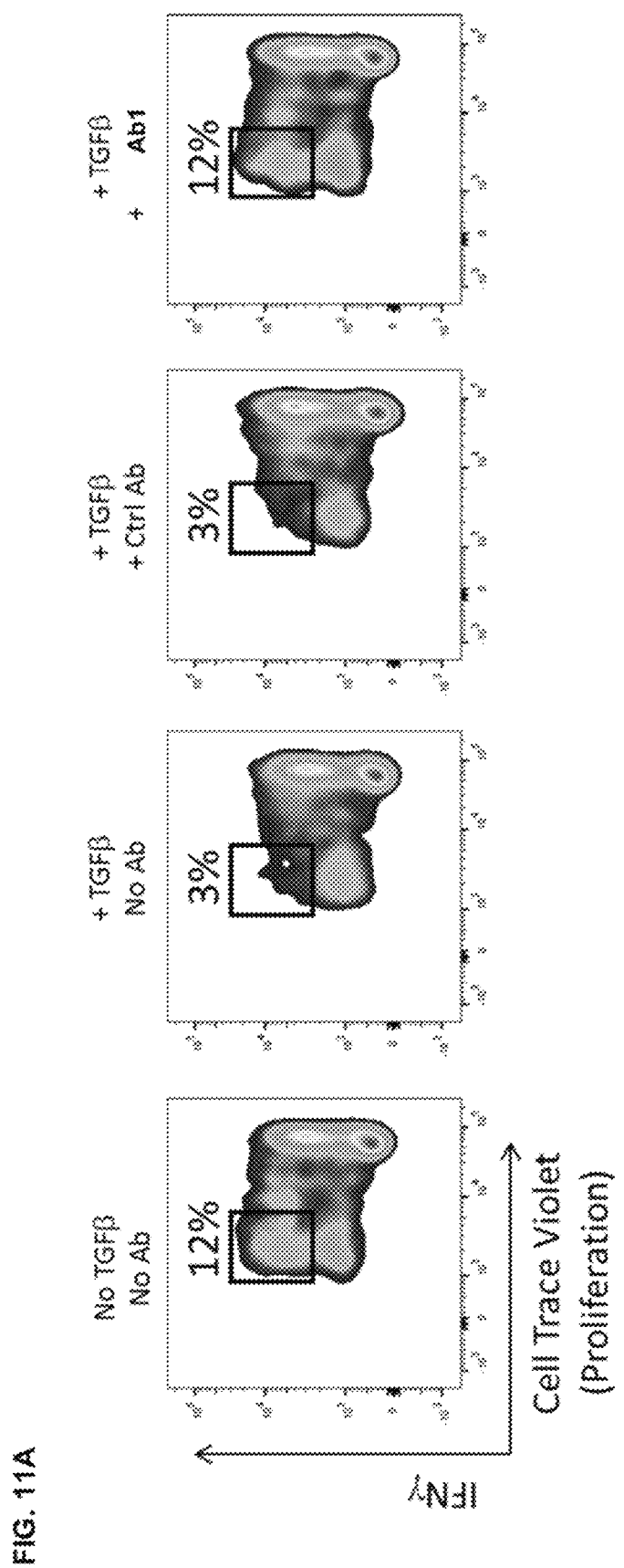
FIG. 11A are graphs quantifying CellTrace Violet staining and IFN-γ staining of CD8$^{pos}$ cells.
Figure 11B:
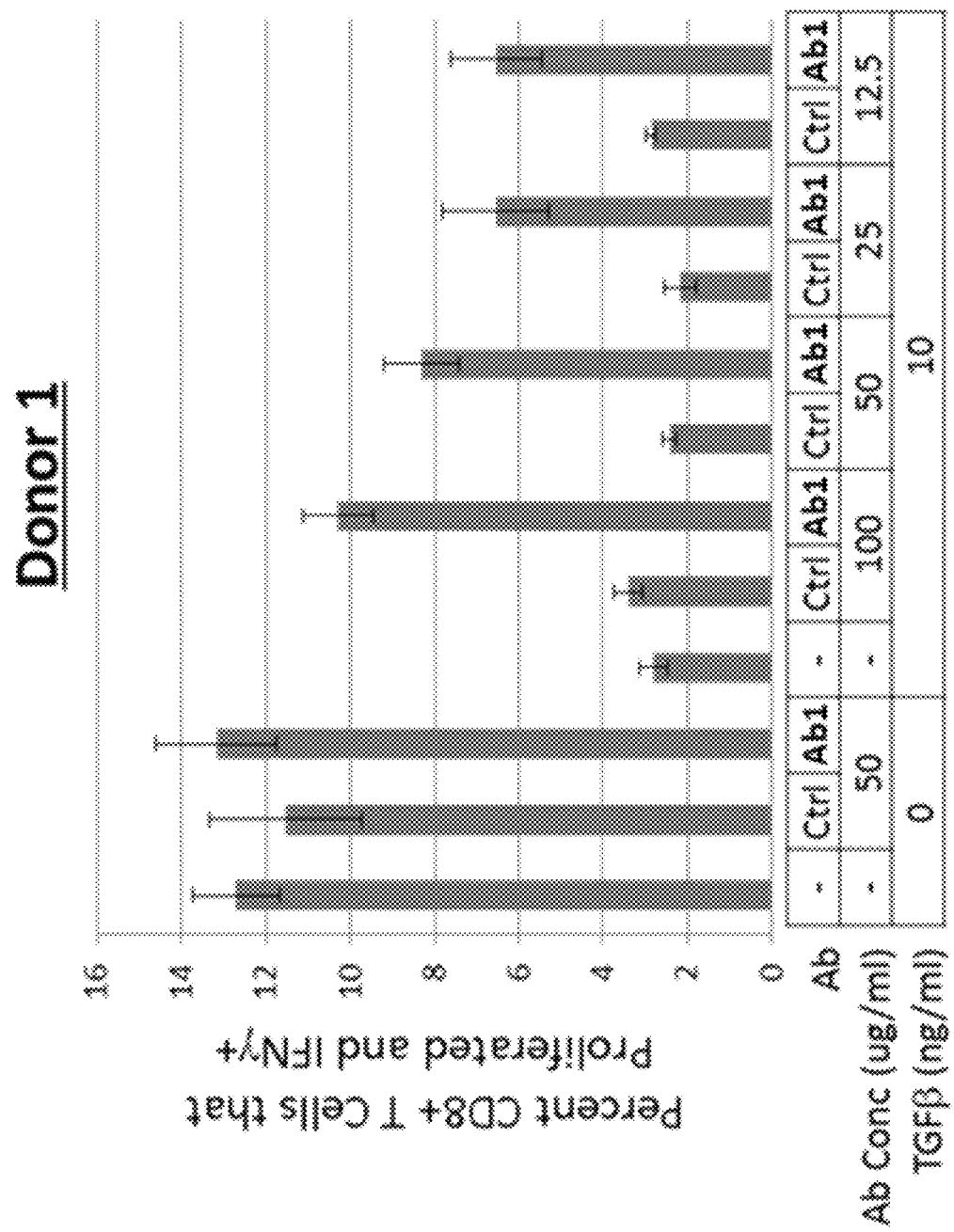
FIG. 11B is a graph showing that Ab1 restored both proliferation and IFN-γ production in TGFβ-treated CD8$^+$ T Cells.

Inclusion of TGF-β in the MLR assay was shown to decrease the percentage of CD8+ T cells that were positive for IFN-γ by approximately 4 fold (FIG. 11A). Inclusion of Ab1 or a control Ab had no effect on the development of these IFNγ+ proliferating CD8+ cells in the absence of TGF-β (FIG. 11B). However, inclusion of Ab1, but not the control antibody, was able to restore the proliferation of the IFNγ+CD8+ cells in a dose-dependent manner. These results demonstrate that TGF-β neutralization is able to impact the adaptive immune system by blocking the immunosuppressive effects of TGF-β on the proliferation of effector CD8+ cells that express IFN-γ. These IFNγ+CD8+ T cells have been suggested to play an important role in anti-tumor immunity (Ikeda et al., Cytokine Growth Factor Rev (2002) 13:95-109).

Example 14: Responses of Syngeneic Mouse Models to Anti-TGF-β Therapy

In this study, we investigated which syngeneic mouse models could be used to predict response to the treatment with the anti-TGF-β antibody Ab1 and anti-PD-1. To stratify the mouse models, we evaluated CD8+ T cell infiltration into the tumors in the mice and TGF-β pathway activation. CD8+ T cell infiltration was assayed based upon a CD8+ T cell signature from data acquired from RNASeq. Seventeen distinct mouse syngeneic models with tumor cells arising from several indications (as shown below x axis in FIGS. 12A and 12B) were transcriptionally profiled using whole-transcriptome RNAseq. This "compendium" of syngeneic models was built on common background strain C57/BL6, with 5 to 7 biological replicates used per model. Following Illumina 2000 sequencing, gene expression profiles expressed in transcripts per million (TPM) were generated by standard processing of raw sequence reads, using the STAR aligner and Cufflinks transcript abundance estimators. The resulting multi-sample data matrix was finally quantile normalized.

Figure 12A:
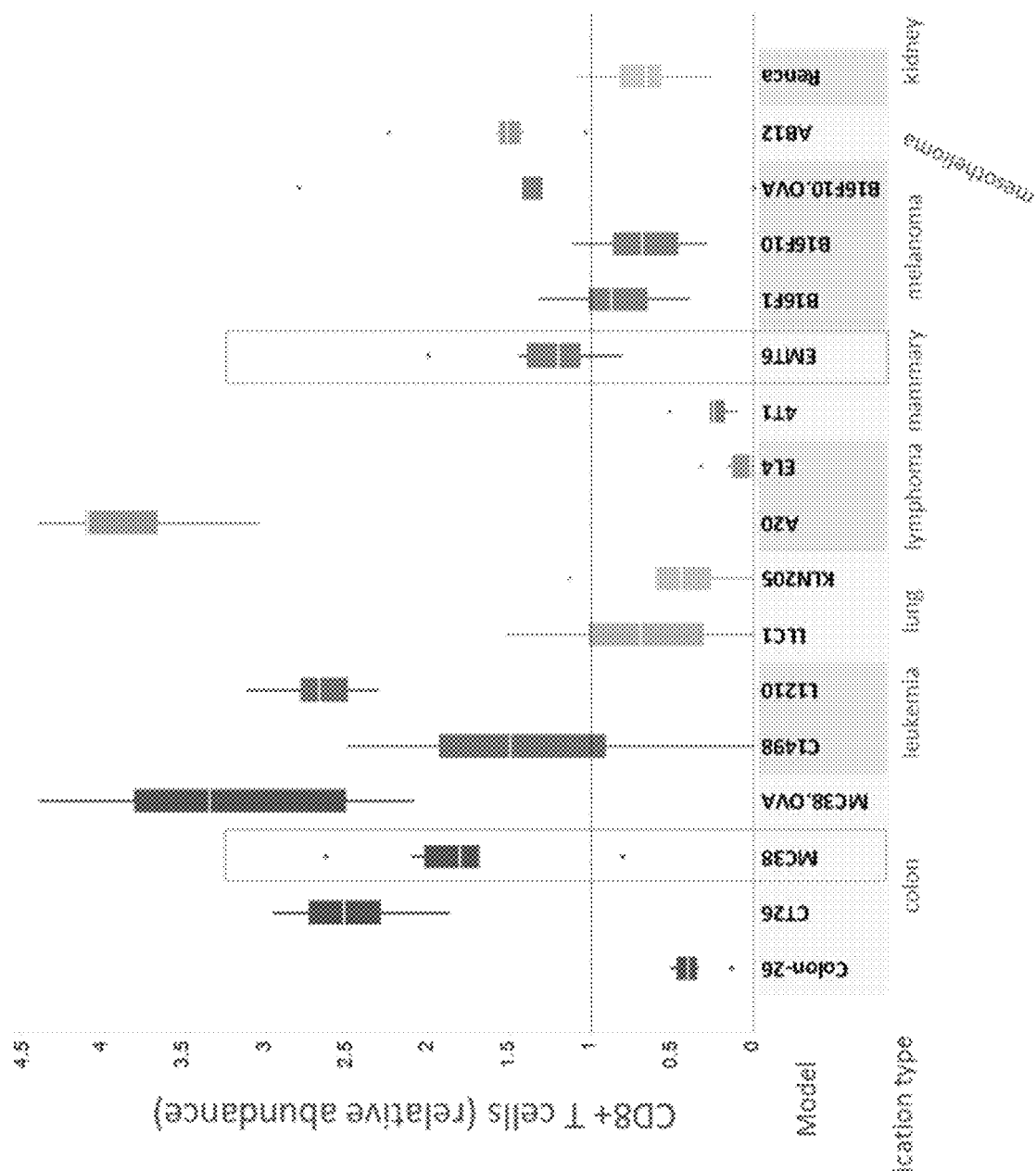
FIG. 12A is a graph showing relative abundance of CD8$^+$ T cells (log 2-transformed) across the compendium of syngeneic mouse tumor models for colon cancer, leukemia, lung cancer, lymphoma, breast cancer, melanoma, mesothelioma and renal cancer.

FIG. 12A shows the relative abundance of CD8⁺ T cells (log 2-transformed) across the compendium. Relative CD8⁺ T cell abundance was estimated using the unique marker gene CD8B, which has been shown to be a highly specific indicator of presence of CD8 T cells (Becht et al., Curr Opin Immunol (2016) 39:7-13; and Becht et al., Genome Biol (2016) 17:218). Each box plot summarizes the range of values across the biological replicates. The MC38 model showed about 2-fold more CD8⁺ T cell infiltration than the EMT6 model (left and right boxes, respectively). The A20 and EL4 lymphoma models displayed overall highest and lowest levels of CD8⁺ T cell infiltration, respectively, with negligible CD8⁺ T cells in EL4.

The MC38, MC38.ova, CT26, and L1210 murine cell lines exhibited the highest levels of the CD8 gene signature. Additionally, the EMT-6 breast cancer cell line was shown to have T cell infiltration close to baseline, which is consistent with recent reports that EMT6 tumors have an immune-excluded phenotype (S. Mariathasan et al. 2017, ESMO Immuno-Oncology Congress, Geneva, Geneva Switzerland).

Figure 12B:
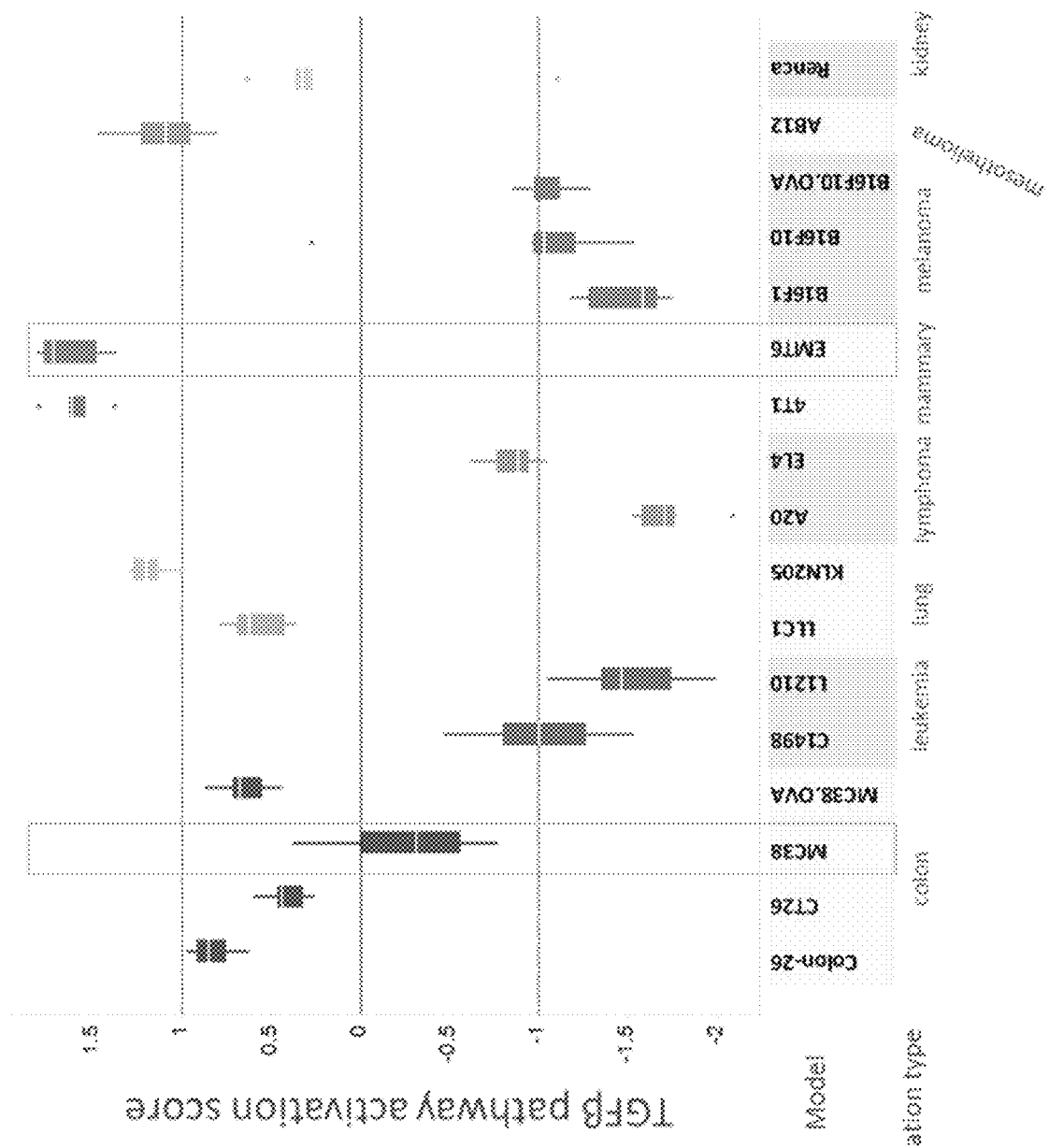
FIG. 12B is a graph showing TGFβ pathway activation across the compendium syngeneic mouse tumor models for colon cancer, leukemia, lung cancer, lymphoma, breast cancer, melanoma, mesothelioma and renal cancer.

FIG. 12B shows TGF-β pathway activation across the compendium. A 170-gene transcriptional signature of TGFβ pathway activation, derived from in vitro stimulation of MCF7 cells by TGF-β and validated by comparison with several other TGF-β signatures, was used to assign a pathway activation score to each profile in the compendium. Scores were computed using "regulated gene set enrichment analysis" (rGSEA, Theilhaber et al. 2014), and expressed as log 2 enrichments of signature genes against the gene background. While the MC38 models displayed average activation, the EMT6 model displayed very high TGF-β pathway activation (left and right boxes, respectively).

Example 15: Effects of Ab1 and Anti-PD1 Antibody Combination on Mouse Breast Cancer Model In this study, we investigated the therapeutic effects of Ab1 with or without anti-PD-1. Exponentially growing EMT-6 breast cells (CRL-2755, ATCC) were cultured in RPMI-1640 supplemented with 10% FBS in a humidified 5% $CO_2$ incubator and then implanted subcutaneously (0.5× $10^6$ cells/mouse) into the flank of female BALB/c mice (Shanghai Lingchang Bio-Technology Co. Ltd, Shanghai, China). Once tumors reached an average size of 68-116 $mm^3$, the mice were pooled and randomly distributed to control and treatment groups (10 mice per group). Tumor-bearing mice were then treated intraperitoneally with PBS, Ab1 (10 and 25 mg/kg) three times per week for each animal for a total of 6 doses. Tumors were measured with digital calipers 2 times per week and tumor volumes calculated ($mm^3$=L×W×H) and graphed using GraphPad Prism. Mice were euthanized with $CO_2$ at the termination of the study, if tumors grew to >3000 $mm^3$ or if the tumors exhibited ulceration >20% of the tumor surface.

As single agents, Ab1 at a dose of 10 or 25 mg/kg Q3D and mouse α-PD-1 antibody at a dose of 5 mg/kg demonstrated partial activity with 1/10, 2/10 and 2/10 complete regression, respectively, in EMT-6 tumor-bearing mice. The combination of Ab1 at a dose of 10 or 25 mg/kg Q3D and mouse α-PD-1 antibodies at 5 mg/kg Q3D was therapeutically active. On day 31 post implantation, when comparing tumor volume changes from baseline, the effect of the combination of Ab1 at all tested doses with mouse α-PD-1 antibody at 5 mg/kg Q3D was greater than the effect of each single agent, with 7/10 and 4/10 complete regression for 10, and 25 mg/kg of Ab1, respectively. Table 10 is a summary of the results.

TABLE 10

Effects of Ab1/anti-mPD-1 Combination on EMT-6 Mouse Model

| Group | Treatment | Total No. of Mice | No. of Complete Response (Complete Response Rate) |
|---|---|---|---|
| 1. | PBS | 10 | 0 (0%) |
| 2. | 5 mg/kg x-anti-mPD-1 Mab | 10 | 2 (20%) |
| 3. | 10 mg/kg Ab1 | 10 | 1 (10%) |
| 4. | 25 mg/kg Ab1 | 10 | 2 (20%) |
| 5. | 10 mg/kg Ab1 + 5 mg/kg x-anti-mPD-1 Mab | 10 | 7 (70%) |
| 6. | 25 mg/kg Ab1 + 5 mg/kg x-anti-mPD-1 Mab | 10 | 4 (40%) |

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Further, unless otherwise required by context, singular terms shall include pluralities and plural terms shall include the singular. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Throughout this specification and embodiments, the words "have" and "comprise," or variations such as "has," "having," "comprises," or "comprising," will be understood to imply the inclusion of a stated integer or group of integers but not the exclusion of any other integer or group of integers.

Sequences described herein are listed below.

```
                       LISTING OF SEQUENCES

SEQ ID NO: 1 (Ab1 heavy chain)
QVQLVQSGAE VKKPGSSVKV SCKASGYTFS SNVISWVRQA PGQGLEWMGG VIPIVDIANY
AQRFKGRVTI TADESTSTTY MELSSLRSED TAVYYCASTL GLVLDAMDYW GQGTLVTVSS
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
```

LISTING OF SEQUENCES

```
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK

SEQ ID NO: 2 (Ab1 light chain)
ETVLTQSPGT LSLSPGERAT LSCRASQSLG SSYLAWYQQK PGQAPRLLIY GASSRAPGIP
DRFSGSGSGT DFTLTISRLE PEDFAVYYCQ QYADSPITFG QGTRLEIKRT VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC SEQ ID NO: 3 (fresolimumab heavy chain, including leader sequence-
residues 1-19)
MGWSCIILFL VATATGVHSQ VQLVQSGAEV KKPGSSVKVS CKASGYTFSS NVISWVRQAP
GQGLEWMGGV IPIVDIANYA QRFKGRVTIT ADESTSTTYM ELSSLRSEDT AVYYCASTLG
LVLDAMDYWG QGTLVTVSSA STKGPSVFPL APCSRSTSES TAALGCLVKD YFPEPVTVSW
NSGALTSGVH TFPAVLQSSG LYSLSSVVTV PSSSLGTKTY TCNVDHKPSN TKVDKRVESK
YGPPCPSCPA PEFLGGPSVF LFPPKPKDTL MISRTPEVTC VVVDVSQEDP EVQFNWYVDG
VEVHNAKTKP REEQFNSTYR VVSVLTVLHQ DWLNGKEYKC KVSNKGLPSS IEKTISKAKG
QPREPQVYTL PPSQEEMTKN QVSLTCLVKG FYPSDIAVEW ESNGQPENNY KTTPPVLDSD
GSFFLYSRLT VDKSRWQEGN VFSCSVMHEA LHNHYTQKSL SLSLGK SEQ ID NO: 4 (fresolimumab light chain, including leader sequence-
residues 1-19)
MGWSCIILFL VATATGVHSE TVLTQSPGTL SLSPGERATL SCRASQSLGS SYLAWYQQKP
GQAPRLLIYG ASSRAPGIPD RFSGSGSGTD FTLTISRLEP EDFAVYYCQQ YADSPITFGQ
GTRLEIKRTV AAPSVFIFPP SDEQLKSGTA SVVCLLNNFY PREAKVQWKV DNALQSGNSQ
ESVTEQDSKD STYSLSSTLT LSKADYEKHK VYACEVTHQG LSSPVTKSFN RGEC SEQ ID NO: 5 (anti-PD-1 Mab heavy chain)
EVQLLESGGV LVQPGGSLRL SCAASGFTFS NFGMTWVRQA PGKGLEWVSG ISGGGRDTYF
ADSVKGRFTI SRDNSKNTLY LQMNSLKGED TAVYYCVKWG NIYFDYWGQG TLVTVSSAST
KGPSVFPLAP CSRSTSESTA ALGCLVKDYF PEPVTVSWNS GALTSGVHTF PAVLQSSGLY
SLSSVVTVPS SSLGTKTYTC NVDHKPSNTK VDKRVESKYG PPCPPCPAPE FLGGPSVFLF
PPKPKDTLMI SRTPEVTCVV VDVSQEDPEV QFNWYVDGVE VHNAKTKPRE EQFNSTYRVV
SVLTVLHQDW LNGKEYKCKV SNKGLPSSIE KTISKAKGQP REPQVYTLPP SQEEMTKNQV
SLTCLVKGFY PSDIAVEWES NGQPENNYKT TPPVLDSDGS FFLYSRLTVD KSRWQEGNVF
SCSVMHEALH NHYTQKSLSL SLGK SEQ ID NO: 6 (anti-PD-1 Mab light chain)
DIQMTQSPSS LSASVGDSIT ITCRASLSIN TFLNWYQQKP GKAPNLLIYA ASSLHGGVPS
RFSGSGSGTD FTLTIRTLQP EDFATYYCQQ SSNTPFGP GTVVDFRRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC SEQ ID NO: 7 (x-anti-mPD-1 Mab heavy chain)
EVQLQESGPG LVKPSQSLSL TCSVTGYSIT SSYRWNWIRK FPGNRLEWMG YINSAGISNY
NPSLKRRISI TRDTSKNQFF LQVNSVTTED AATYYCARSD NMGTTPFTYW GQGTLVTVSS
AKTTPPSVYP LAPGSAAQTN SMVTLGCLVK GYFPEPVTVT WNSGSLSSGV HTFPAVLQSD
LYTLSSSVTV PSSTWPSETV TCNVAHPASS TKVDKKIVPR DCGCKPCICT VPEVSSVFIF
PPKPKDVLTI TLTPKVTCVV VDISKDDPEV QFSWFVDDVE VHTAQTQPRE EQFNSTFRSV
SELPIMHQDW LNGKEFKCRV NSAAFPAPIE KTISKTKGRP KAPQVYTIPP PKEQMAKDKV
SLTCMITDFF PEDITVEWQW NGQPAENYKN TQPIMDTDGS YFVYSKLNVQ KSNWEAGNTF
TCSVLHEGLH NHHTEKSLSH SPG SEQ ID NO: 8 (x-anti-mPD-1 Mab light chain)
DIVMTQGTLP NPVPSGESVS ITCRSSKSLL YSDGKTYLNW YLQRPGQSPQ LLIYWMSTRA
SGVSDRFSGS GSGTDFTLKI SGVEAEDVGI YYCQQGLEFP TFGGGTKLEL KRADAAPTVS
IFPPSTEQLA TGGASVVCLM NNFYPRDISV KWKIDGTERR DGVLDSVTDQ DSKDSTYSMS
STLSLTKADY ESHNLYTCEV VHKTSSSPVV KSFNRNEC SEQ ID NO: 9 (1D11 heavy chain)
HVQLQQSGPE LVRPGASVKL SCKASGYIFI TYWMNWVKQR PGQGLEWIGQ IFPASGSTNY
NEMFEGKATL TVDTSSSTAY MQLSSLTSED SAVYYCARGD GNYALDAMDY WGQGTSVTVS
SAKTTPPSVY PLAPGSAAQT NSMVTLGCLV KGYFPEPVTV TWNSGSLSSG VHTFPAVLQS
DLYTLSSSVT VPSSTWPSQT VTCNVAHPAS STKVDKKIVP RDCGCKPCIC TVPEVSSVFI
FPPKPKDVLT ITLTPKVTCV VVDISKDDPE VQFSWFVDDV EVHTAQTKPR EEQFNSTFRS
VSELPIMHQD WLNGKEFKCR VNSAAFPAPI EKTISKTKGR PKAPQVYTIP PPKEQMAKDK
VSLTCMITDF FPEDITVEWQ WNGQPAENYK NTQPIMDTDG SYFVYSKLNV QKSNWEAGNT
FTCSVLHEGL HNHHTEKSLS HSPGK SEQ ID NO: 10 (1D11 light chain)
NIVLTQSPAS LAVSLGQRAT ISCRASESVD SYGNSFMHWY QQKSGQPPKL LIYLASNLES
GVPARFSGSG SRTDFTLTID PVEADDAATY YCQQNNEDPL TFGAGTKLEL KRADAAPTVS
IFPPSSEQLT SGGASVVCFL NNFYPKDINV KWKIDGSERQ NGVLNSWTDQ DSKDSTYSMS
STLTLTKDEY ERHNSYTCEA THKTSTSPIV KSFNRNEC
```

What is claimed is:

1. A method of inhibiting TGF-β signal transduction in a patient in need thereof, comprising administering to the patient a therapeutic amount of an isolated monoclonal antibody, wherein the antibody binds to human TGF-β1, TGF-β2, and TGF-β3 and comprises the heavy chain complementarity-determining regions (CDR) 1-3 in SEQ ID NO:1 and the light chain CDR1-3 in SEQ ID NO:2, and wherein the antibody comprises a human IgG$_4$ constant region having a proline at position 228 (EU numbering).

2. The method of claim 1, wherein the patient has cancer.

3. The method of claim 2, wherein the cancer is selected from the group consisting of melanoma, lung cancer, cutaneous squamous cell carcinoma, colorectal cancer, breast cancer, ovarian cancer, head and neck cancer, hepatocellular carcinoma, urothelial cancer, and renal cell carcinoma.

4. The method of claim 2, wherein the cancer is characterized by overexpression of one or more of smooth muscle α2 actin (ACTA2), vimentin (VIM), matrix Gla protein (MGP), and ZW10 interacting kinetochore protein (ZWINT).

5. The method of claim 2, wherein the cancer is a mesenchymal tumor.

6. The method of claim 2, wherein the antibody alleviates an immunosuppressive tumor microenvironment in a cancer tissue in the patient.

7. The method of claim 1, wherein the antibody comprises a heavy chain variable domain (V$_H$) amino acid sequence corresponding to residues 1-120 of SEQ ID NO:1 and a light chain variable domain (V$_L$) amino acid sequence corresponding to residues 1-108 of SEQ ID NO:2.

8. The method of claim 7, wherein the antibody comprises a heavy chain amino acid sequence set forth in SEQ ID NO:1 and a light chain amino acid sequence set forth in SEQ ID NO:2.

9. A method of treating cancer or increasing an immune response in a patient in need thereof, comprising administering to the patient (1) a therapeutically effective amount of an isolated monoclonal antibody, and (2) a therapeutically effective amount of an inhibitor of an immune checkpoint protein, wherein the antibody binds to human TGF-β1, TGF-β2, and TGF-β3 and comprises the heavy chain complementarity-determining regions (CDR) 1-3 in SEQ ID NO:1 and the light chain CDR1-3 in SEQ ID NO:2, and wherein the antibody comprises a human IgG$_4$ constant region having a proline at position 228 (EU numbering).

10. The method of claim 9, wherein the immune checkpoint protein is PD-1, PD-L1, or PD-L2.

11. The method of claim 10, wherein the inhibitor of the immune checkpoint protein is an anti-PD-1 antibody.

12. The method of claim 11, wherein the anti-PD-1 antibody comprises:
   a) the heavy chain CDR1-3 in SEQ ID NO:5 and the light chain CDR1-3 in SEQ ID NO:6;
   b) a V$_H$ amino acid sequence corresponding to residues 1-117 of SEQ ID NO:5 and a V$_L$ amino acid sequence corresponding to residues 1-107 of SEQ ID NO:6; or c) a heavy chain amino acid sequence set forth in SEQ ID NO:5 and a light chain amino acid sequence set forth in SEQ ID NO:6.

13. The method of claim 12, wherein the anti-TGF-β antibody comprises a heavy chain amino acid sequence set forth in SEQ ID NO:1 and a light chain amino acid sequence set forth in SEQ ID NO:2.

14. The method of claim 9, wherein the cancer is refractory to anti-PD-1 or anti-PD-L1 antibody treatment.

15. The method of claim 9, wherein the cancer is advanced or metastatic melanoma, or cutaneous squamous cell carcinoma.

16. The method of claim 9, wherein the cancer is a mesenchymal subtype of a solid tumor.

17. The method of claim 9, wherein the cancer is characterized by overexpression of one or more of smooth muscle α2 actin (ACTA2), vimentin (VIM), matrix Gla protein (MGP), and ZW10 interacting kinetochore protein (ZWINT).

18. The method of claim 9, wherein the cancer is selected from the group consisting of melanoma, lung cancer, cutaneous squamous cell carcinoma, colorectal cancer, breast cancer, ovarian cancer, head and neck cancer, hepatocellular carcinoma, urothelial cancer, and renal cell carcinoma.

19. The method of claim 9, wherein the antibody comprises a heavy chain variable domain ($V_H$) amino acid sequence corresponding to residues 1-120 of SEQ ID NO:1 and a light chain variable domain ($V_L$) amino acid sequence corresponding to residues 1-108 of SEQ ID NO:2.

20. The method of claim 19, wherein the antibody comprises a heavy chain amino acid sequence set forth in SEQ ID NO:1 and a light chain amino acid sequence set forth in SEQ ID NO:2.

21. A method of treating cancer in a patient in need thereof, comprising administering to the patient (1) a therapeutically effective amount of an isolated monoclonal antibody, and (2) a therapeutically effective amount of an antibody to PD-1 or PD-L1, wherein the isolated monoclonal antibody comprises a heavy chain amino acid sequence set forth in SEQ ID NO:1 and a light chain amino acid sequence set forth in SEQ ID NO:2.

22. The method of claim 21, wherein the cancer is refractory to anti-PD-1 or anti-PD-L1 antibody treatment.

23. The method of claim 21, wherein the antibody to PD-1 or PD-L1 is an antibody to PD-1 comprising a heavy chain amino acid sequence set forth in SEQ ID NO:5 and a light chain amino acid sequence set forth in SEQ ID NO:6.

24. The method of claim 21, wherein the cancer is advanced or metastatic melanoma, or cutaneous squamous cell carcinoma.

25. The method of claim 21, wherein the cancer is a mesenchymal subtype of a solid tumor.

26. The method of claim 21, wherein the cancer is colorectal cancer.

27. The method of claim 21, wherein the cancer is urothelial cancer.

28. The method of claim 21, wherein the cancer is non-small cell lung cancer.

29. The method of claim 21, wherein the cancer is hepatocellular carcinoma.

30. The method of claim 21, wherein the cancer is ovarian cancer.

31. The method of claim 21, wherein the cancer is cervical cancer.

32. The method of claim 21, wherein the cancer is pancreatic cancer.

33. The method of claim 21, wherein the cancer is prostate cancer.

* * * * *

SEQUENCE LISTING

<160> NUMBER OF SEQ ID NOS: 10

<210> SEQ ID NO 1
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 2
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 3

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Ser Ser Asn Val Ile Ser Trp Val Arg Gln Ala Pro Gly Gln Gly Leu
    50                  55                  60

Glu Trp Met Gly Gly Val Ile Pro Ile Val Asp Ile Ala Asn Tyr Ala
65                  70                  75                  80

Gln Arg Phe Lys Gly Arg Val Thr Ile Thr Ala Asp Glu Ser Thr Ser
                85                  90                  95

Thr Thr Tyr Met Glu Leu Ser Ser Leu Arg Ser Glu Asp Thr Ala Val
            100                 105                 110

Tyr Tyr Cys Ala Ser Thr Leu Gly Leu Val Leu Asp Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415
```

```
Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 4
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Cys Ile Ile Leu Phe Leu Val Ala Thr Ala Thr Gly
1               5                   10                  15

Val His Ser Glu Thr Val Leu Thr Gln Ser Pro Gly Thr Leu Ser Leu
            20                  25                  30

Ser Pro Gly Glu Arg Ala Thr Leu Ser Cys Arg Ala Ser Gln Ser Leu
        35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Pro Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Ala
            100                 105                 110

Asp Ser Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 5
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 5

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

```
Met Gly Tyr Ile Asn Ser Ala Gly Ile Ser Asn Tyr Asn Pro Ser Leu
 50                  55                  60

Lys Arg Arg Ile Ser Ile Thr Arg Asp Thr Ser Lys Asn Gln Phe Phe
 65                  70                  75                  80

Leu Gln Val Asn Ser Val Thr Thr Glu Asp Ala Ala Thr Tyr Tyr Cys
                 85                  90                  95

Ala Arg Ser Asp Asn Met Gly Thr Thr Pro Phe Thr Tyr Trp Gly Gln
            100                 105                 110

Gly Thr Leu Val Thr Val Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
    275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
    355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly
    435                 440

<210> SEQ ID NO 8
<211> LENGTH: 218
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 8

```
Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Gly Thr Lys Leu Glu Leu Lys Arg
            100                 105                 110

Ala Asp Ala Ala Pro Thr Val Ser Ile Phe Pro Pro Ser Thr Glu Gln
        115                 120                 125

Leu Ala Thr Gly Gly Ala Ser Val Val Cys Leu Met Asn Asn Phe Tyr
    130                 135                 140

Pro Arg Asp Ile Ser Val Lys Trp Lys Ile Asp Gly Thr Glu Arg Arg
145                 150                 155                 160

Asp Gly Val Leu Asp Ser Val Thr Asp Gln Asp Ser Lys Asp Ser Thr
                165                 170                 175

Tyr Ser Met Ser Ser Thr Leu Ser Leu Thr Lys Ala Asp Tyr Glu Ser
            180                 185                 190

His Asn Leu Tyr Thr Cys Glu Val Val His Lys Thr Ser Ser Ser Pro
        195                 200                 205

Val Val Lys Ser Phe Asn Arg Asn Glu Cys
    210                 215
```

<210> SEQ ID NO 9
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
His Val Gln Leu Gln Gln Ser Gly Pro Glu Leu Val Arg Pro Gly Ala
1               5                   10                  15

Ser Val Lys Leu Ser Cys Lys Ala Ser Gly Tyr Ile Phe Ile Thr Tyr
            20                  25                  30

Trp Met Asn Trp Val Lys Gln Arg Pro Gly Gln Gly Leu Glu Trp Ile
        35                  40                  45

Gly Gln Ile Phe Pro Ala Ser Gly Ser Thr Asn Tyr Asn Glu Met Phe
    50                  55                  60

Glu Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

Ala Arg Gly Asp Gly Asn Tyr Ala Leu Asp Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Pro
            180                 185                 190

Ser Ser Thr Trp Pro Ser Gln Thr Val Thr Cys Asn Val Ala His Pro
            195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Lys
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 10
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 10

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```